(12) United States Patent
Morell et al.

(10) Patent No.: US 7,038,020 B1
(45) Date of Patent: May 2, 2006

(54) POLYPEPTIDES CAPABLE OF FORMING ANTIGEN BINDING STRUCTURES WITH SPECIFICITY FOR THE RHESUS D ANTIGENS, THE DNA ENCODING THEM AND THE PROCESS FOR THEIR PREPARATION AND USE

(75) Inventors: Andreas Morell, Bolligen (CH); Martin Imboden, Toffen (CH); Beda Stadler, Bern (CH); Sylvia Miescher, Bern (CH); Monique Vogel, Lausanne (CH); Hanspeter Amstutz, Bolligen (CH)

(73) Assignee: ZLB Behring AG, Bern (CH)

( * ) Notice: Subject to any disclaimer, the term of this patent is extended or adjusted under 35 U.S.C. 154(b) by 0 days.

(21) Appl. No.: 09/147,443

(22) PCT Filed: Jun. 20, 1997

(86) PCT No.: PCT/EP97/03253

§ 371 (c)(1),
(2), (4) Date: Jan. 21, 1999

(87) PCT Pub. No.: WO97/49809

PCT Pub. Date: Dec. 31, 1997

(30) Foreign Application Priority Data

Jun. 24, 1996 (EP) .................................. 96810421

(51) Int. Cl.
*C07K 16/28* (2006.01)
*A61K 39/395* (2006.01)
*C07H 21/00* (2006.01)
*G01N 33/53* (2006.01)

(52) U.S. Cl. .............................. 530/388.1; 424/153.1; 536/23.53; 435/7.25

(58) Field of Classification Search ............. 530/387.1, 530/387.3, 388.1, 388.2, 388.7; 424/141.1, 424/153.1, 173.1; 536/23.53; 435/7.25
See application file for complete search history.

(56) References Cited

FOREIGN PATENT DOCUMENTS

WO WO91/07492 5/1991

OTHER PUBLICATIONS

Seigel (Annals N.Y. Acad. Sciences, (1995) 764:547-558.*
D. L. Siegel et al, Blood, "Expression and Characterization of Recombinant Anti-Rh(D) . . . ", vol. 83, pp. 2334-2344, 1994.
M. Dziegiel et al, J. Immunology Methods, vol. 182, "Phage display used for gene cloning . . . ", pp. 7-19, 1995.
J. D. Marks et al, Biotechnology, vol. 11, "Human Antibody Fragments Specific . . . ", pp. 1145-1149, 1993.
D. L. Siegel, Ann. New York Academy of Sciences, "Isolation of Human Anti-Red Blood . . . ", pp. 547-558, 1995.
Dziegiel et al. J. of Cellular Biochemistry, Feb. 26, 1994, Abstract # T513.
Barbas III et al., "Combinatorial Immunoglobulin Libraries on the Surface of Phage (Phabs); Rapid Selection of Antigen-specific Fabs," *Methods: A Comparison to Methods in Enzymology*, Apr. 1991, pp. 119-124, vol. 2, No. 2, Academic Press, Inc.
Chérif-Zahar et al., "Molecular cloning and protein structure of a human blood group Rh polypeptide," *Proc. Natl. Acad. Sci. USA*, Aug. 1990, pp. 6243-6247, vol. 87.
Crawford et al., "Production of Human monoclonal Antibody to Rhesus D Antigen," *The Lancet*, Feb. 19, 1983, pp. 386-388, vol. I, No. 8321.
Dziegiel et al., "Recombinant Antibody Against the Erythrocyte Antigen, Rhesus D," Abstract No. T513, *Journal of Cellular Biochemistry*, Feb. 26-Apr. 17, 1994, p. 212, Supplement 18D, Wiley-Liss.
Hughes-Jones, "Human Monoclonal Antibodies and Haemolytic Disease of the Newborn," *British Journal of Haematology*, Nov. 1988, pp. 263-265, vol. 70, No. 3, Blackwell Scientific Publications.

(Continued)

*Primary Examiner*—Christina Chan
*Assistant Examiner*—F. Pierre VanderVegt
(74) *Attorney, Agent, or Firm*—Foley & Lardner LLP

(57) ABSTRACT

Polypeptides capable of forming antigen binding structures specific for Rhesus D antigens include the sequences indicated in the FIGS. 1a to 16b. The obtained polypeptides, being Fab fragments, MAY be used directly as an active ingredient in pharmaceutical and diagnostic compositions. The Fab and their DNA sequences can also be used for the preparation of complete recombinant Anti-Rhesus D antibodies. Useful in pharmaceutical and diagnostic compostions.

12 Claims, 34 Drawing Sheets

OTHER PUBLICATIONS

Issitt, "Genetics of the Rh blood group system: some current concepts," *Medical Laboratory Sciences,* 1988, pp. 395-404, vol. 45, Blackwell Scientific Publications.

Kozbor et al., "The production of monoclonal antibodies from human lymphocytes," *Immnology Today,* 1983, pp. 72-79, 1983, vol. 4, No. 3, Elsevier Science Publishers B.V.

Le Van Kim et al., "Molecular cloning and primary structure of the human blood group RhD polypeptide," *Proc. Natl. Acad. Sci. USA,* Nov. 1992, pp. 10925-10929, vol. 89.

Mouro et al., "Rearrangements of the Blood Group RhD Gene Associated with the $D^{VI}$ Category Phenotype," *Blood,* Feb. 15, 1994, pp. 1129-1135, vol. 83, No. 4, The American Society of Hematology.

Paradis et al., "Protective Effect of the membrane Skeleton on the Immunologic Reactivity of the Human Red Cell $Rh_o$ (D) Antigen," *The Journal of Immunology,* Jul. 1, 1986, pp. 240-244, vol. 137, No. 1, The American Association of Immunologies.

Persson et al., "Generation of diverse high-affinity human monoclonal antibodies by repertoire cloning," *Proc. Natl. Acad. Sci. USA,* Mar. 1991, pp. 2432-2436, vol. 88.

Race et al. (Eds.), *Blood Groups in Man,* 1975, Table Of Contents Only, Blackwell Scientific Publications.

Selinger, "Immunoprophylaxis for rhesus disease —expensive but worth it?" *British Journal of Obstetrics and Gynaecology,* Jun. 1991, pp. 509-512, vol. 98, No. 6, Blackwell Scientific Publications.

Siegel et al., "Isolation of Human Anti-Red Blood Cell Antibodies by Repertoire Cloning," *Annals New York Academy of Sciences,* Sep. 29, 1995, pp. 547-558, vol. 764, New York Academy of Sciences, USA.

Tippett et al., "The Rh Antigen D: Partial D Antigens and Associated Low Incidence Antigens," *Vox Sanguinis,* Feb. 1996, pp. 123-131, vol. 70, S. Karger AG, Basel.

Vogel et al., "Human anti-IgE antibodies by repertoire cloning," *Eur. J. Immunol.,* May 1994, pp. 1200-1207, vol. 24, VCH Verlagsgesellschaft mbH, Weinheim.

Williamson et al., "Human monoclonal antibodies against a plethora of viral pathogens from single combinatorial libraries," *Proc. Natl. Acad. Sci. USA,* May 1993, pp. 4141-4145, vol. 90.

Zebedee et al., "Human combinatorial antibody libraries to hepatitis B surface antigen," *Proc. Natl. Acad. Sci. USA,* Apr. 1992, pp. 3175-3179, vol. 89.

* cited by examiner

Fig. 1a

LD1-40-VH sequence

```
                9                18               27               36               45               54
5' CAG GTG AAA CTG CTC GAG TCT GGG GGA GGC GTG GTC CAG CCT GGG AGG TCC CTG
   --- --- --- --- --- --- --- --- --- --- --- --- --- --- --- --- --- ---
    Q   V   K   L   L   E   S   G   G   G   V   V   Q   P   G   R   S   L 63               72               81               90               99              108
   AGA CTC TCC TGT ATA GCG TCT GGA TTC ACC CTC AGG AAT TAT GCC ATG CAC TGG
   --- --- --- --- --- --- --- --- --- --- --- --- --- --- --- --- --- ---
    R   L   S   C   I   A   S   G   F   T   L   R   N   Y   A   M   H   W
                                                          ←——— CDR1 ———→

117              126              135              144              153              162
   GTC CGC CAG GCT CCA GGC AAG GGG CTG GAG TGG GTG GCA GGT ATA TGG TTT GAT
   --- --- --- --- --- --- --- --- --- --- --- --- --- --- --- --- --- ---
    V   R   Q   A   P   G   K   G   L   E   W   V   A   G   I   W   F   D
                                                          ←——— CDR2

171              180              189              198              207              216
   GGA AGT AAC AAA AAC TAT GCA GAC TCC GTG AAG GGC CGA TTC ACC ATC TCC AGA
   --- --- --- --- --- --- --- --- --- --- --- --- --- --- --- --- --- ---
    G   S   N   K   N   Y   A   D   S   V   K   G   R   F   T   I   S   R
                    ————————— CDR2 —————————→
              225              234              243              252              261              270
   GAC AAT TCC AAG AAC ACG CTG TAT CTG CAA CTG AAC AGC CTG AGA GAC GAG GAC
   --- --- --- --- --- --- --- --- --- --- --- --- --- --- --- --- --- ---
    D   N   S   K   N   T   L   Y   L   Q   L   N   S   L   R   D   E   D 279              288              297              306              315              324
   ACG GCT GTG TAT TAT TGT GCG AGA GAG CGA GCA GCA CGT GGT ATT TCT AGG TTC
   --- --- --- --- --- --- --- --- --- --- --- --- --- --- --- --- --- ---
    T   A   V   Y   Y   C   A   R   E   R   A   A   R   G   I   S   R   F
                                      ←——————————— CDR3
              333              342              351              360              369
   TAT TAC TAC ATG GAC GTC TGG GGC AAA GGG ACC ACG GTC ACC GTC TCC CCA  3'
   --- --- --- --- --- --- --- --- --- --- --- --- --- --- --- --- ---
    Y   Y   Y   M   D   V   W   G   K   G   T   T   V   T   V   S   P
   ——————— CDR3 ———————→
```

Fig. 1b

LD1-40-VL sequence

```
           9              18              27              36              45              54
5' GTG ATG ACC CAG TCT CCA TCC TCC CTG TCT GCA TCT GTA GGC GAC AGA GTC ACC
   --- --- --- --- --- --- --- --- --- --- --- --- --- --- --- --- --- ---
    V   M   T   Q   S   P   S   S   L   S   A   S   V   G   D   R   V   T 63             72              81              90              99             108
   ATC ACT TGC CGG GCA AGT CAG AGC ATT AGG AGC CAT TTG AAT TGG TAT CAG CAG
   --- --- --- --- --- --- --- --- --- --- --- --- --- --- --- --- --- ---
    I   T   C   R   A   S   Q   S   I   R   S   H   L   N   W   Y   Q   Q
                       ←―――――――――――――― CDR1 ――――――――――――→

117            126             135             144             153             162
   AAA CCA GGG AAA GCC CCT AAG TTG CTG ATC TAT GGT GCG TCC ACT TTG CAA AGT
   --- --- --- --- --- --- --- --- --- --- --- --- --- --- --- --- --- ---
    K   P   G   K   A   P   K   L   L   I   Y   G   A   S   T   L   Q   S
                                                       ←――――― CDR2 ―――――→

171            180             189             198             207             216
   GGC GTC CCA TCA AGG TTC AGT GGC AGT GGC TCT GGG GCA GTT TTC ACT CTC ACC
   --- --- --- --- --- --- --- --- --- --- --- --- --- --- --- --- --- ---
    G   V   P   S   R   F   S   G   S   G   S   G   A   V   F   T   L   T 225            234             243             252             261             270
   ATC GCC AGT CTA CAA CCT GAA GAT TTT GCA ACT TAC TAC TGT CAA GAG AGT TAC
   --- --- --- --- --- --- --- --- --- --- --- --- --- --- --- --- --- ---
    I   A   S   L   Q   P   E   D   F   A   T   Y   Y   C   Q   E   S   Y
                                                                    ←―――――

279            288             297             306             315
   AGT AAT CCT CTA ATC ACC TTC GGC CAA GGG ACA CGA CTG GAG ACT AAA 3'
   --- --- --- --- --- --- --- --- --- --- --- --- --- --- ---
    S   N   P   L   I   T   F   G   Q   G   T   R   L   E   T   K
    ―――――― CDR3 ――――――→
```

Fig. 2a

LD1-52-VH sequence

```
           9              18             27             36             45             54
5'  CAG GTG AAA CTG CTC GAG TCT GGG GGA GGC GTG GTC CAG CCG GGG GGG TCC CTG
    --- --- --- --- --- --- --- --- --- --- --- --- --- --- --- --- --- ---
     Q   V   K   L   L   E   S   G   G   G   V   V   Q   P   G   G   S   L 63             72             81             90             99            108
    AGA CTC TCC TGT GAA GCG TCT GGA TTC GCC CTC AGA AGT TCT GGC ATG CAC TGG
    --- --- --- --- --- --- --- --- --- --- --- --- --- --- --- --- --- ---
     R   L   S   C   E   A   S   G   F   A   L   R   S   S   G   M   H   W
                                                              ←——— CDR1 ———→
                 117            126            135            144            153            162
    GTC CGC CAG GCT CCT GGC AAG GGG CTG GAG TGG GTG GCA CTT ATA TGG TTT GAT
    --- --- --- --- --- --- --- --- --- --- --- --- --- --- --- --- --- ---
     V   R   Q   A   P   G   K   G   L   E   W   V   A   L   I   W   F   D
                                                                  ←——— CDR2 ———
                 171            180            189            198            207            216
    GGA AGT ATC AGA TCG TAT GCA GAA TCC GTG AAG GGC CGA TTC ACC ATC TCC AGA
    --- --- --- --- --- --- --- --- --- --- --- --- --- --- --- --- --- ---
     G   S   I   R   S   Y   A   E   S   V   K   G   R   F   T   I   S   R
    ————————————————— CDR2 ———————————————→
                 225            234            243            252            261            270
    GAC ACT TCC AAG AAC ACC CTA TAT CTC CAA ATG CGC AGT CTG AGT GCC GAC GAC
    --- --- --- --- --- --- --- --- --- --- --- --- --- --- --- --- --- ---
     D   T   S   K   N   T   L   Y   L   Q   M   R   S   L   S   A   D   D 279            288            297            306            315            324
    ACG GCT GTG TAT TAC TGT GCG AGA GAC AAG GCG GTT CGG GGA ATT AGC AGG TAC
    --- --- --- --- --- --- --- --- --- --- --- --- --- --- --- --- --- ---
     T   A   V   Y   Y   C   A   R   D   K   A   V   R   G   I   S   R   Y
                                     ←——————————— CDR3 ———
                 333            342            351            360            369
    AAC TAT TAC ATG GAC GTC TGG GGC AAA GGG ACC ACG GTC ACC GTC TCC TCA  3'
    --- --- --- --- --- --- --- --- --- --- --- --- --- --- --- --- ---
     N   Y   Y   M   D   V   W   G   K   G   T   T   V   T   V   S   S
    ————— CDR3 ———————→
```

Fig. 2b

LD1-52-VL sequence

```
          9              18              27              36              45              54
5' GTG ATG ACC CAG TCT CCA TCC TCC CTG TCT GCA TCT GTA GGA GAC AGA GTC ACC
   --- --- --- --- --- --- --- --- --- --- --- --- --- --- --- --- --- ---
    V   M   T   Q   S   P   S   S   L   S   A   S   V   G   D   R   V   T 63              72              81              90              99             108
   ATC ACT TGC CGG GCA AGT CAG AAC ATT ATC CGC TAT TTA AAT TGG TAT CAG CAG
   --- --- --- --- --- --- --- --- --- --- --- --- --- --- --- --- --- ---
    I   T   C   R   A   S   Q   N   I   I   R   Y   L   N   W   Y   Q   Q
                    ←─────────────── CDR1 ───────────────→
             117             126             135             144             153             162
   AAG CCA GGG AAA GCC CCT AGG CTC CTG ATC TAT GGT GCG TCC ACT TTG CAA AGT
   --- --- --- --- --- --- --- --- --- --- --- --- --- --- --- --- --- ---
    K   P   G   K   A   P   R   L   L   I   Y   G   A   S   T   L   Q   S
                                                    ←─────────── CDR2 ───────────→
             171             180             189             198             207             216
   GGG GTC CCA TCA AGG TTC AGT GGC AGT GGA TCT GGG ACA GAT TTC ACT CTC ACC
   --- --- --- --- --- --- --- --- --- --- --- --- --- --- --- --- --- ---
    G   V   P   S   R   F   S   G   S   G   S   G   T   D   F   T   L   T 225             234             243             252             261             270
   ATC AGT AGT CTG CAA CCT GAA GAT TTT GCA ACT TAC TAC TGT CAA CAG AGT TAC
   --- --- --- --- --- --- --- --- --- --- --- --- --- --- --- --- --- ---
    I   S   S   L   Q   P   E   D   F   A   T   Y   Y   C   Q   Q   S   Y
                                                                ←───────
             279             288             297             306             315
   CGT ACC CCT CCA TTC ACT TTC GGC CCT GGG ACC AAA GTG GAG ATC AAA   3'
   --- --- --- --- --- --- --- --- --- --- --- --- --- --- ---
    R   T   P   P   F   T   F   G   P   G   T   K   V   E   I   K
   ─────── CDR3 ───────→
```

Fig. 3a

LD1-84-VH sequence

```
            9              18              27              36              45              54
5'  CAG GTG AAA CTG CTC GAG TCT GGG GGA GGC GTG GTC CAG CCG GGG GGG TCC CTG
     Q   V   K   L   L   E   S   G   G   G   V   V   Q   P   G   G   S   L 63              72              81              90              99             108
    AGA CTC TCC TGT GAA GCG TCT GGA TTC ACC CTC AGA AGT TCT GGC ATG CAC TGG
     R   L   S   C   E   A   S   G   F   T   L   R   S   S   G   M   H   W
                                                            ←———— CDR1 ————→
               117             126             135             144             153             162
    GTC CGC CAG GCT CCT GGC AAG GGG CTG GAG TGG GTG GCA CTT ATA TGG TTT GAT
     V   R   Q   A   P   G   K   G   L   E   W   V   A   L   I   W   F   D
                                                              ←———— CDR2 ————
               171             180             189             198             207             216
    GGA AGT ATC AGA TCG TAT GCA GAA TCC GTG AAG GGC CGA TTC ACC ATC TCC AGA
     G   S   I   R   S   Y   A   E   S   V   K   G   R   F   T   I   S   R
    ———————————————— CDR2 ————————————————→
               225             234             243             252             261             270
    GAC ACT TCC AAG AAC ACC CTA TAT CTC CAA ATG CGC AGT CTG AGT GCC GAC GAC
     D   T   S   K   N   T   L   Y   L   Q   M   R   S   L   S   A   D   D 279             288             297             306             315             324
    ACG GCT GTG TAT TAC TGT GCG AGA GAC AAG GCG GTT CGG GGA ATT AGC AGG TAC
     T   A   V   Y   Y   C   A   R   D   K   A   V   R   G   I   S   R   Y
                                                ←———————————————— CDR3 ————
               333             342             351             360             369
    AAC TAT TAC ATG GAC GTC TGG GGC AAA GGG ACC ACG GTC ACC GTC TCC TCA  3'
     N   Y   Y   M   D   V   W   G   K   G   T   T   V   T   V   S   S
    ———————— CDR3 ————————→
```

Fig. 3b

LD1-84-VL sequence

```
              9             18             27             36             45             54
5'  GTG ATG ACC CAG TCT CCA TCC TCC CTG TCT GCA TCT ATA GGA GAC AGA GTC ACC
    --- --- --- --- --- --- --- --- --- --- --- --- --- --- --- --- --- ---
     V   M   T   Q   S   P   S   S   L   S   A   S   I   G   D   R   V   T 63             72             81             90             99            108
    ATC ACC TGC CGG GCA AGT CAG AGT ATC ATC AGG TAT TTG AAT TGG TAT CAG CAC
    --- --- --- --- --- --- --- --- --- --- --- --- --- --- --- --- --- ---
     I   T   C   R   A   S   Q   S   I   I   R   Y   L   N   W   Y   Q   H
                                 ←─────────── CDR1 ───────────→

117            126            135            144            153            162
    AAA CCA GGA AAA GCC CCT AAA CTC CTC ATC TTT GCT GCA TCG AAT TTG CAA ACT
    --- --- --- --- --- --- --- --- --- --- --- --- --- --- --- --- --- ---
     K   P   G   K   A   P   K   L   L   I   F   A   A   S   N   L   Q   T
                                                 ←─────────── CDR2 ───────────→

171            180            189            198            207            216
    GGG GTC CCA TCC AGG TTC AGT GGC AGT GGA TCT GGG ACA GAT TTC ACT CTC ACC
    --- --- --- --- --- --- --- --- --- --- --- --- --- --- --- --- --- ---
     G   V   P   S   R   F   S   G   S   G   S   G   T   D   F   T   L   T 225            234            243            252            261            270
    ATC AGT GAC CTG CAG CCT GAG GAT TTC GCA ACT TAC TAC TGT CAA CAG AGT TAC
    --- --- --- --- --- --- --- --- --- --- --- --- --- --- --- --- --- ---
     I   S   D   L   Q   P   E   D   F   A   T   Y   Y   C   Q   Q   S   Y
                                                                 ←───────────

279            288            297            306            315
    AGT AGG CCG TTC ACT TTT GGC CGG GGG ACC AGC CTG GAC ATC AAA  3'
    --- --- --- --- --- --- --- --- --- --- --- --- --- --- ---
     S   R   P   F   T   F   G   R   G   T   S   L   D   I   K
    ─────── CDR3 ───────→
```

Fig. 4a

LD1-110-VH sequence

```
              9              18              27              36              45              54
5'  CAG GTG AAA CTG CTC GAG TCT GGG GGA GGC GTG GTC CAG CCT GGG AGG TCC CTG
    --- --- --- --- --- --- --- --- --- --- --- --- --- --- --- --- --- ---
     Q   V   K   L   L   E   S   G   G   G   V   V   Q   P   G   R   S   L 63              72              81              90              99             108
    AGA CTC TCC TGT ATA GCG TCT GGA TTC ACC CTC AGG AAT TAT GCC ATG CAC TGG
    --- --- --- --- --- --- --- --- --- --- --- --- --- --- --- --- --- ---
     R   L   S   C   I   A   S   G   F   T   L   R   N   Y   A   M   H   W
                                                        ←——— CDR1 ———→
           117             126             135             144             153             162
    GTC CGC CAG GCT CCA GGC AAG GGG CTG GAG TGG GTG GCA GGT ATA TGG TTT GAT
    --- --- --- --- --- --- --- --- --- --- --- --- --- --- --- --- --- ---
     V   R   Q   A   P   G   K   G   L   E   W   V   A   G   I   W   F   D
                                                              ←——— CDR2 ———
           171             180             189             198             207             216
    GGA AGC AAC AAA AAC TAT GCA GAC TCC GTG AAG GGC CGA TTC ACC ATC TCC AGA
    --- --- --- --- --- --- --- --- --- --- --- --- --- --- --- --- --- ---
     G   S   N   K   N   Y   A   D   S   V   K   G   R   F   T   I   S   R
    ———————————————— CDR2 ————————————————→
           225             234             243             252             261             270
    GAC AAC TCC AAG AAC ACT CTG TTT CTG CAC ATG AAC AGC CTG AGA GCC GAG GAC
    --- --- --- --- --- --- --- --- --- --- --- --- --- --- --- --- --- ---
     D   N   S   K   N   T   L   F   L   H   M   N   S   L   R   A   E   D 279             288             297             306             315             324
    ACG GCT ACA TAT TAC TGT GCG AGA GAG AGG GCG ATT CGG GGA ATC AGT AGA TAC
    --- --- --- --- --- --- --- --- --- --- --- --- --- --- --- --- --- ---
     T   A   T   Y   Y   C   A   R   E   R   A   I   R   G   I   S   R   Y
                                                ←——————— CDR3 ———————
           333             342             351             360             369
    AAT TAC TAC ATG GAC GTC TGG GGC AAG GGG ACC ACG GTC ACC GTC TCC TCA  3'
    --- --- --- --- --- --- --- --- --- --- --- --- --- --- --- --- ---
     N   Y   Y   M   D   V   W   G   K   G   T   T   V   T   V   S   S
    ——————— CDR3 ———————→
```

Fig. 4b

LD1-110-VL sequence

```
         9              18              27              36              45              54
5' GTG ATG ACC CAG TCT CCA TCC TCC CTG TCT GCA TCT GTA GGA GAC AGA GTC ACC
   --- --- --- --- --- --- --- --- --- --- --- --- --- --- --- --- --- ---
    V   M   T   Q   S   P   S   S   L   S   A   S   V   G   D   R   V   T 63              72              81              90              99             108
   ATC ACT TGC CGG GCA AGT CAG AGC ATT CGA AGC TCT TTA AAT TGG TAT CAG CAG
   --- --- --- --- --- --- --- --- --- --- --- --- --- --- --- --- --- ---
    I   T   C   R   A   S   Q   S   I   R   S   S   L   N   W   Y   Q   Q
                       ←——————————————— CDR1 ———————————————→

117             126             135             144             153             162
   AAA CCA GGG AAA GCC CCT AAA GTC CTG ATC TAT GCT GCA TCC AGT TTG CAA AGT
   --- --- --- --- --- --- --- --- --- --- --- --- --- --- --- --- --- ---
    K   P   G   K   A   P   K   V   L   I   Y   A   A   S   S   L   Q   S
                                               ←——————————— CDR2 ———————————→

171             180             189             198             207             216
   GGG GTC CCA TCC AGG TTC AGT GGC AGA GGA TCT GGG ACA GAT TTC ACT CTC ACC
   --- --- --- --- --- --- --- --- --- --- --- --- --- --- --- --- --- ---
    G   V   P   S   R   F   S   G   R   G   S   G   T   D   F   T   L   T 225             234             243             252             261             270
   ATC AGC AGT CTG CAG CCT GAA GAT TTT GCG ACT TAT TAT TGT CAA CAG AGT TCC
   --- --- --- --- --- --- --- --- --- --- --- --- --- --- --- --- --- ---
    I   S   S   L   Q   P   E   D   F   A   T   Y   Y   C   Q   Q   S   S
                                                               ←———————————

279             288             297             306             315
   AGT TCC TCG TGG ACG TTC GGC CAA GGG ACC AAG GTG GAA ATC AAA 3'
   --- --- --- --- --- --- --- --- --- --- --- --- --- --- ---
    S   S   S   W   T   F   G   Q   G   T   K   V   E   I   K
   ——————— CDR3 ———————→
```

Fig. 5a

LD1-117-VH sequence

```
         9              18             27             36             45             54
5' CAG GTG AAA CTG CTC GAG TCA GGA GGA GGC GTG GTC CAG CCT GGG AAG TCC CTG
   --- --- --- --- --- --- --- --- --- --- --- --- --- --- --- --- --- ---
    Q   V   K   L   L   E   S   G   G   G   V   V   Q   P   G   K   S   L 63             72             81             90             99            108
   AGA CTT TCC TGT GCA GCG TCT GGA TTC AGT TTC AAT AGC CAT GGC ATG CAC TGG
   --- --- --- --- --- --- --- --- --- --- --- --- --- --- --- --- --- ---
    R   L   S   C   A   A   S   G   F   S   F   N   S   H   G   M   H   W
                                                     ←——— CDR1 ———→

117            126            135            144            153            162
   GTC CGC CAG GCT CCA GGC AAG GGG CTG GAG TGG GTG GCA TTT ATA TGG TTT GAT
   --- --- --- --- --- --- --- --- --- --- --- --- --- --- --- --- --- ---
    V   R   Q   A   P   G   K   G   L   E   W   V   A   F   I   W   F   D
                                                         ←——— CDR2 ———

171            180            189            198            207            216
   GGC AGT AAT AAA TAC TAT GCA GAC TCC GTG AAG GGC CGA TTC ACC ATC ACC AGA
   --- --- --- --- --- --- --- --- --- --- --- --- --- --- --- --- --- ---
    G   S   N   K   Y   Y   A   D   S   V   K   G   R   F   T   I   T   R
   ——————————————— CDR2 ———————————————→

225            234            243            252            261            270
   GAC AAC TCC AAG AAC ACG CTG TAT CTG CAA ATG AAC AGC CTG AGA GCC GAG GAC
   --- --- --- --- --- --- --- --- --- --- --- --- --- --- --- --- --- ---
    D   N   S   K   N   T   L   Y   L   Q   M   N   S   L   R   A   E   D 279            288            297            306            315            324
   ACG GCT GTC TAT TAC TGT GCG AGA GAG ACC TCA GTA AGG CTA GGG TAT AGC CGC
   --- --- --- --- --- --- --- --- --- --- --- --- --- --- --- --- --- ---
    T   A   V   Y   Y   C   A   R   E   T   S   V   R   L   G   Y   S   R
                                                         ←——— CDR3 ———

333            342            351            360            369            378
   TAC AAT TAC TAC ATG GAC GTC TGG GGC AAA GGG ACC ACG GTC ACC ATC TCG TCA  3'
   --- --- --- --- --- --- --- --- --- --- --- --- --- --- --- --- --- ---
    Y   N   Y   Y   M   D   V   W   G   K   G   T   T   V   T   I   S   S
   ——————————— CDR3 ———————————→
```

Fig. 5b

LD1-117-VL sequence

```
             9              18               27               36               45              54
5' GTG ATG ACC CAG TCT CCA TCC TCC CTG TCT GCA TCT GTA GGA GAC AGA GTC ACC
   --- --- --- --- --- --- --- --- --- --- --- --- --- --- --- --- --- ---
    V   M   T   Q   S   P   S   S   L   S   A   S   V   G   D   R   V   T 63              72               81               90               99             108
   ATC ACT TGC CGG GCA AGT CAG AGC ATT AGG AGC CAT TTG AAT TGG TAT CAG CAG
   --- --- --- --- --- --- --- --- --- --- --- --- --- --- --- --- --- ---
    I   T   C   R   A   S   Q   S   I   R   S   H   L   N   W   Y   Q   Q
               ←─────────────────── CDR1 ───────────────────→

117             126              135              144              153             162
   AAA CCA GGG AAA GCC CCT AAG CTC CTG ATC TAT GCT GCA TCC AGT TTG CAA GGT
   --- --- --- --- --- --- --- --- --- --- --- --- --- --- --- --- --- ---
    K   P   G   K   A   P   K   L   L   I   Y   A   A   S   S   L   Q   G
                                              ←──────── CDR2 ────────→

171             180              189              198              207             216
   GGG GTC CCA TCA AGG TTC AGT GGC AGT GGA TCT GGG ACA GAT TTC ACT CTC ACC
   --- --- --- --- --- --- --- --- --- --- --- --- --- --- --- --- --- ---
    G   V   P   S   R   F   S   G   S   G   S   G   T   D   F   T   L   T 225             234              243              252              261             270
   ATC AGC AGT CTG CAA CCT GAA GAT TTT GCA ACT TAT TAC TGT CAA CAG AGT TAC
   --- --- --- --- --- --- --- --- --- --- --- --- --- --- --- --- --- ---
    I   S   S   L   Q   P   E   D   F   A   T   Y   Y   C   Q   Q   S   Y
                                                                     ←────

279             288              297              306              315
   AGG GCC CCT CAG TGG ACG TTC GGC CAA GGG ACC AAG GTG GAA ATC AAA   3'
   --- --- --- --- --- --- --- --- --- --- --- --- --- --- ---
    R   A   P   Q   W   T   F   G   Q   G   T   K   V   E   I   K
   ─────── CDR3 ───────→
```

Fig. 6a

LD2-1-VH sequence

```
            9              18             27             36             45             54
5' CAG GTG AAA CTG CTC GAG TCT GGG GGA GGC GTG GTC CAG CCG GGG GGG TCC CTG
   --- --- --- --- --- --- --- --- --- --- --- --- --- --- --- --- --- ---
    Q   V   K   L   L   E   S   G   G   G   V   V   Q   P   G   G   S   L 63             72             81             90             99            108
   AGA CTC TCC TGT GTA GCG TCT GGA TTC ACC CTC AGG AGT TAT GGC ATG CAC TGG
   --- --- --- --- --- --- --- --- --- --- --- --- --- --- --- --- --- ---
    R   L   S   C   V   A   S   G   F   T   L   R   S   Y   G   M   H   W
                                                        ←——— CDR1 ———→

117            126            135            144            153            162
   GTC CGC CAG GCT CCA GGC AAG GGC CTG GAG TGG GTG GCT TTT ATA TGG TTT GAT
   --- --- --- --- --- --- --- --- --- --- --- --- --- --- --- --- --- ---
    V   R   Q   A   P   G   K   G   L   E   W   V   A   F   I   W   F   D
                                                            ←——— CDR2 ———

171            180            189            198            207            216
   GGA AGT AAT AAA GGA TAT GTA GAC TCC GTG AAG GGC CGA TTC ACC ATC TCC CGA
   --- --- --- --- --- --- --- --- --- --- --- --- --- --- --- --- --- ---
    G   S   N   K   G   Y   V   D   S   V   K   G   R   F   T   I   S   R
   ————————————— CDR2 —————————————→

225            234            243            252            261            270
   GAC AAT TCC AAG AAC ATG GTC TAT CTG CAA ATG AAC AGC CTG AGA GCC GAT GAC
   --- --- --- --- --- --- --- --- --- --- --- --- --- --- --- --- --- ---
    D   N   S   K   N   M   V   Y   L   Q   M   N   S   L   R   A   D   D 279            288            297            306            315            324
   ACG GCT GTA TAT TAT TGT GCG AGA GAG AAG GCG CTT CGG GGA ATC AGC AGA TAC
   --- --- --- --- --- --- --- --- --- --- --- --- --- --- --- --- --- ---
    T   A   V   Y   Y   C   A   R   E   K   A   L   R   G   I   S   R   Y
                                        ←——————————— CDR3 ———————————

333            342            351            360            369
   AAC TAT TAC CTG GAC GTC TGG GGC AAG GGG ACC ACG GTC ACC GTC TCC TCA 3'
   --- --- --- --- --- --- --- --- --- --- --- --- --- --- --- --- ---
    N   Y   Y   L   D   V   W   G   K   G   T   T   V   T   V   S   S
   ————— CDR3————→
```

Fig. 6b

LD2-1-VL sequence

```
          9              18              27              36              45              54
5' GTG GTG ACT CAG CCA CCC TCA GCG TCT GGG ACC CCC GGA CAG AGG GTC ACC ATC
   --- --- --- --- --- --- --- --- --- --- --- --- --- --- --- --- --- ---
    V   V   T   Q   P   P   S   A   S   G   T   P   G   Q   R   V   T   I 63              72              81              90              99             108
   TCT TGT TCT GGA AGC AAC TCC ATC CTT GGA AGT AAG TAT GTA TAC TGG TAC CAG
   --- --- --- --- --- --- --- --- --- --- --- --- --- --- --- --- --- ---
    S   C   S   G   S   N   S   I   L   G   S   K   Y   V   Y   W   Y   Q
               ←————————————————— CDR1 —————————————————→
         117             126             135             144             153             162
   AAA CTC CCA GGA ACG GCC CCC AAA CTC CTC ATC TAT AAG AAT GAT CAG CGG CCC
   --- --- --- --- --- --- --- --- --- --- --- --- --- --- --- --- --- ---
    K   L   P   G   T   A   P   K   L   L   I   Y   K   N   D   Q   R   P
                                                    ←————— CDR2 —————
         171             180             189             198             207             216
   TCA GGG GTC TCT GAC CGA TTC TCT GGC TCC AAG TCT GGC ACC TCG GCC TCC CTG
   --- --- --- --- --- --- --- --- --- --- --- --- --- --- --- --- --- ---
    S   G   V   S   D   R   F   S   G   S   K   S   G   T   S   A   S   L
   —→
         225             234             243             252             261             270
   GCC ATC AGT GGG CTC CGG TCC GAG GAT GAG GCT GAC TAT TAC TGT GCA CCA TGG
   --- --- --- --- --- --- --- --- --- --- --- --- --- --- --- --- --- ---
    A   I   S   G   L   R   S   E   D   E   A   D   Y   Y   C   A   P   W
                                                                    ←—————
         279             288             297             306             315             324
   GAT GCC AAC CTG GGT GGC CCG GTG TTC GGC GGA GGG ACC AAG CTG ACC GTC CTA
   --- --- --- --- --- --- --- --- --- --- --- --- --- --- --- --- --- ---
    D   A   N   L   G   G   P   V   F   G   G   G   T   K   L   T   V   L
   ————————————— CDR3 —————————————→
         333
   AGT CAG CCC  3'
   --- --- ---
    S   Q   P
```

Fig. 7a

LD2-4-VH sequence

```
               9              18              27              36              45              54
5' CAG GTG AAA CTG CTC GAG TCG GGG GGA GGC GTG GTC CAG CCG GGG GGG TCC CTG
   --- --- --- --- --- --- --- --- --- --- --- --- --- --- --- --- --- ---
    Q   V   K   L   L   E   S   G   G   G   V   V   Q   P   G   G   S   L 63              72              81              90              99             108
   AGA CTC TCC TGT GAA GCG TCT GGA TTC ACC CTC AGA AGT TCT GGC ATG CAC TGG
   --- --- --- --- --- --- --- --- --- --- --- --- --- --- --- --- --- ---
    R   L   S   C   E   A   S   G   F   T   L   R   S   S   G   M   H   W
                                                         ←——— CDR1 ———→

117             126             135             144             153             162
   GTC CGC CAG GCT CCT GGC AAG GGG CTG GAG TGG GTG GCA CTT ATA TGG TTT GAT
   --- --- --- --- --- --- --- --- --- --- --- --- --- --- --- --- --- ---
    V   R   Q   A   P   G   K   G   L   E   W   V   A   L   I   W   F   D
                                                             ←——— CDR2 ———

171             180             189             198             207             216
   GGA AGT ATC AGA TCG TAT GCA GAA TCC GTG AAG GGC CGA TTC ACC ATC TCC AGA
   --- --- --- --- --- --- --- --- --- --- --- --- --- --- --- --- --- ---
    G   S   I   R   S   Y   A   E   S   V   K   G   R   F   T   I   S   R
   ——————————————————— CDR2 ———————————————————→

225             234             243             252             261             270
   GAC ACT TCC AAG AAC ACC CTA TAT CTC CAA ATG CGC AGT CTG AGT GCC GAC GAC
   --- --- --- --- --- --- --- --- --- --- --- --- --- --- --- --- --- ---
    D   T   S   K   N   T   L   Y   L   Q   M   R   S   L   S   A   D   D 279             288             297             306             315             324
   ACG GCT GTG TAT TAC TGT GCG AGA GAC AAG GCG GTT CGG GGA ATT AGC AGG TAC
   --- --- --- --- --- --- --- --- --- --- --- --- --- --- --- --- --- ---
    T   A   V   Y   Y   C   A   R   D   K   A   V   R   G   I   S   R   Y
                                        ←——————————— CDR3 ———————————

333             342             351             360             369
   AAC TAT TAC ATG GAC GTC TGG GGC AAA GGG ACC ACG GTC ACC GTC TCC TCA 3'
   --- --- --- --- --- --- --- --- --- --- --- --- --- --- --- ---
    N   Y   Y   M   D   V   W   G   K   G   T   T   V   T   V   S   S
   ——————— CDR3 ———————→
```

Fig. 7b

LD2-4-VL sequence

```
              9              18              27              36              45              54
5' GTG ATG ACC CAG TCT CCA TCC TCC CTG TCT GCA TCT GTA GGA GAC AGA GTC ACC
   --- --- --- --- --- --- --- --- --- --- --- --- --- --- --- --- --- ---
    V   M   T   Q   S   P   S   S   L   S   A   S   V   G   D   R   V   T 63              72              81              90              99             108
   ATC ACT TGC CGG ACA AGT CAG ACC ATT AGC AGA AAT TTA AAT TGG TAT CAG CAG
   --- --- --- --- --- --- --- --- --- --- --- --- --- --- --- --- --- ---
    I   T   C   R   T   S   Q   T   I   S   R   N   L   N   W   Y   Q   Q
               ←───────────── CDR1 ─────────────→
            117             126             135             144             153             162
   AAA CCA GGG AAA GCC CCT AAG CTC CTG ATC TAT GCT ACA TCC AGT TTG CAA AGT
   --- --- --- --- --- --- --- --- --- --- --- --- --- --- --- --- --- ---
    K   P   G   K   A   P   K   L   L   I   Y   A   T   S   S   L   Q   S
                                              ←───────── CDR2 ─────────→
            171             180             189             198             207             216
   GGG GTC CCA TCA AGG TTC AGT GGC AGT GGA TCT GGG ACA GAT TTC ACT CTC ACC
   --- --- --- --- --- --- --- --- --- --- --- --- --- --- --- --- --- ---
    G   V   P   S   R   F   S   G   S   G   S   G   T   D   F   T   L   T 225             234             243             252             261             270
   ATC AAT AGT CTA CAA CCT GAA GAT TTT GCA ACT TAC TAC TGT CAA CAG AGT TAC
   --- --- --- --- --- --- --- --- --- --- --- --- --- --- --- --- --- ---
    I   N   S   L   Q   P   E   D   F   A   T   Y   Y   C   Q   Q   S   Y
                                                              ←─────────
            279             288             297             306             315
   ACT ACC CCT TCG TTC GGC CAA GGG ACC AAG GTG GAA ATC AAA  3'
   --- --- --- --- --- --- --- --- --- --- --- --- --- ---
    T   T   P   S   F   G   Q   G   T   K   V   E   I   K
   ──── CDR3 ────→
```

Fig. 8a

LD2-5-VH sequence

```
           9              18             27             36             45             54
5' CAG GTG AAA CTG CTC GAG TCT GGG GGA GGC TTG GTC CAG CCG GGG GGG TCC CTG
   --- --- --- --- --- --- --- --- --- --- --- --- --- --- --- --- --- ---
    Q   V   K   L   L   E   S   G   G   G   L   V   Q   P   G   G   S   L 63             72             81             90             99            108
   AGA CTC TCC TGT GTA GCG TCT GGA TTC ACC TTC AGG AGT TAT GGC ATG CAC TGG
   --- --- --- --- --- --- --- --- --- --- --- --- --- --- --- --- --- ---
    R   L   S   C   V   A   S   G   F   T   F   R   S   Y   G   M   H   W
                                                         ←——————— CDR1 ———————→
                 117            126            135            144            153            162
   GTC CGC CAG GCT CCA GGC AAG GGC CTG GAG TGG GTG GCT TTT ATA TGG TTT GAT
   --- --- --- --- --- --- --- --- --- --- --- --- --- --- --- --- --- ---
    V   R   Q   A   P   G   K   G   L   E   W   V   A   F   I   W   F   D
                                                                 ←——————— CDR2
                 171            180            189            198            207            216
   GGA AGT AAT AAA GGA TAT GTA GAC TCC GTG AAG GGC CGA TTC ACC ATC TCC CGA
   --- --- --- --- --- --- --- --- --- --- --- --- --- --- --- --- --- ---
    G   S   N   K   G   Y   V   D   S   V   K   G   R   F   T   I   S   R
   ——————————————— CDR2 ———————————————→
                 225            234            243            252            261            270
   GAC AAT TCC AAG AAC ATG CTC TAT CTG CAA ATG AAT AGC CTG AGA GCC GAG GAC
   --- --- --- --- --- --- --- --- --- --- --- --- --- --- --- --- --- ---
    D   N   S   K   N   M   L   Y   L   Q   M   N   S   L   R   A   E   D 279            288            297            306            315            324
   ACG GCT GTA TAT TAT TGT GCG AGA GAG AAG GCG CTT CGG GGA ATC AGT AGA TAC
   --- --- --- --- --- --- --- --- --- --- --- --- --- --- --- --- --- ---
    T   A   V   Y   Y   C   A   R   E   K   A   L   R   G   I   S   R   Y
                                        ←——————————— CDR3
                 333            342            351            360            369
   AAC TAT TAC CTG GAC GTC TGG GGC AAG GGG GCC ACG GTC ACC GTC TCC TCA   3'
   --- --- --- --- --- --- --- --- --- --- --- --- --- --- --- ---
    N   Y   Y   L   D   V   W   G   K   G   A   T   V   T   V   S   S
   ——————— CDR3 ———————→
```

Fig. 8b

LD2-5-VL sequence

```
            9              18             27             36             45              54
5' GTG ATG ACC CAG TCT CCA TCC TCC CTG TCT GCA TCT ATA GGC GAC AGA GTC ACC
   --- --- --- --- --- --- --- --- --- --- --- --- --- --- --- --- --- ---
    V   M   T   Q   S   P   S   S   L   S   A   S   I   G   D   R   V   T 63             72             81             90             99             108
   ATC ACT TGC CGG GCA AGT CAG AGC GTT ACC AGG TCT TTA AAT TGG TAT CAG CAG
   --- --- --- --- --- --- --- --- --- --- --- --- --- --- --- --- --- ---
    I   T   C   R   A   S   Q   S   V   T   R   S   L   N   W   Y   Q   Q
                    ←─────────────────── CDR1 ───────────────────→
           117            126            135            144            153            162
   AAA CCA GGG AAA GCC CCT AGG CTC CTA ATC TTT GCT GCG TCC ACT TTG CAA AGT
   --- --- --- --- --- --- --- --- --- --- --- --- --- --- --- --- --- ---
    K   P   G   K   A   P   R   L   L   I   F   A   A   S   T   L   Q   S
                                                    ←──────── CDR2 ────────→
           171            180            189            198            207            216
   GGG GTC CCA TCA AGG TTC AGT GGC AGT GGA TCT GGG ACA GAT TTC ACC CTC ACC
   --- --- --- --- --- --- --- --- --- --- --- --- --- --- --- --- --- ---
    G   V   P   S   R   F   S   G   S   G   S   G   T   D   F   T   L   T 225            234            243            252            261            270
   ATC AGC AGT CTG CAA CCT GAG GAT TTT GGA ACT TAC TAC TGT CAA CAG AAT TAC
   --- --- --- --- --- --- --- --- --- --- --- --- --- --- --- --- --- ---
    I   S   S   L   Q   P   E   D   F   G   T   Y   Y   C   Q   Q   N   Y
                                                                ←
           279            288            297            306            315
   AGG ACC CCT CAG TGG ACG TTC GGC CAA GGG ACC AAG GTA GAA ATC AAA    3'
   --- --- --- --- --- --- --- --- --- --- --- --- --- --- --- ---
    R   T   P   Q   W   T   F   G   Q   G   T   K   V   E   I   K
   ─────────── CDR3 ───────────→
```

Fig. 9a

LD2-10-VH sequence

```
              9              18              27              36              45              54
5' CAG GTG AAA CTG CTC GAG TCT GGG GGA GGC GTG GTC CAG CCG GGG GGG TCC CTG
   --- --- --- --- --- --- --- --- --- --- --- --- --- --- --- --- --- ---
    Q   V   K   L   L   E   S   G   G   G   V   V   Q   P   G   G   S   L 63              72              81              90              99             108
   AGA CTC TCC TGT GTA GCG TCT GGA TTC ACC CTC AGG AGT TAT GGC ATG CAC TGG
   --- --- --- --- --- --- --- --- --- --- --- --- --- --- --- --- --- ---
    R   L   S   C   V   A   S   G   F   T   L   R   S   Y   G   M   H   W
                                                       ←———— CDR1 ————→
             117             126             135             144             153             162
   GTC CGC CAG GCT CCA GGC AAG GGC CTG GAG TGG GTG GCT TTT ATA TGG TTT GAT
   --- --- --- --- --- --- --- --- --- --- --- --- --- --- --- --- --- ---
    V   R   Q   A   P   G   K   G   L   E   W   V   A   F   I   W   F   D
                                                           ←———— CDR2 ————
             171             180             189             198             207             216
   GGA AGT AAT AAA GGA TAT GTA GAC TCC GTG AAG GGC CGA TTC ACC ATC TCC CGA
   --- --- --- --- --- --- --- --- --- --- --- --- --- --- --- --- --- ---
    G   S   N   K   G   Y   V   D   S   V   K   G   R   F   T   I   S   R
   ————————————— CDR2 ——————————→
             225             234             243             252             261             270
   GAC AAT TCC AAG AAC ATG GTC TAT CTG CAA ATG AAC AGC CTG AGA GCC GAT GAC
   --- --- --- --- --- --- --- --- --- --- --- --- --- --- --- --- --- ---
    D   N   S   K   N   M   V   Y   L   Q   M   N   S   L   R   A   D   D 279             288             297             306             315             324
   ACG GCT GTA TAT TAT TAT TGT GCG AGA GAG AAG GCG CTT CGG GGA ATC AGC AGA
   --- --- --- --- --- --- --- --- --- --- --- --- --- --- --- --- --- ---
    T   A   V   Y   Y   Y   C   A   R   E   K   A   L   R   G   I   S   R
                                        ←———————— CDR3 —————————
             333             342             351             360             369             378
   TAC AAC TAT TAC CTG GAC GTC TGG GGC AAG GGG ACC ACG GTC ACC GTC TCC TCA  3'
   --- --- --- --- --- --- --- --- --- --- --- --- --- --- --- --- --- ---
    Y   N   Y   Y   L   D   V   W   G   K   G   T   T   V   T   V   S   S
   ———————————— CDR3 ———————————→
```

Fig. 9b

LD2-10-VL sequence

```
                9                 18                27                36                45                54
5'  GTG GTG ACT CAG GAG CCC TCA CTG ACT GTG TCC CCA GGA GGG ACA GTC ACT CTC
    --- --- --- --- --- --- --- --- --- --- --- --- --- --- --- --- --- ---
     V   V   T   Q   E   P   S   L   T   V   S   P   G   G   T   V   T   L 63                72                81                90                99               108
    ACC TGT GCT TCC AGC ACT GGG GCA GTC ACC AGG GGT TAC TAT CCA AAC TGG TTC
    --- --- --- --- --- --- --- --- --- --- --- --- --- --- --- --- --- ---
     T   C   A   S   S   T   G   A   V   T   R   G   Y   Y   P   N   W   F
                        ←——————————————————— CDR1 ———————————————————→
               117               126               135               144               153               162
    CAG CAG AAG CCT GGA CAA GCA CCC AGG GCA CTG ATT TAT AGT ACA AAC AAA AAA
    --- --- --- --- --- --- --- --- --- --- --- --- --- --- --- --- --- ---
     Q   Q   K   P   G   Q   A   P   R   A   L   I   Y   S   T   N   K   K
                                                                ←——————— CDR2 ———————
               171               180               189               198               207               216
    CAC TCC TGG ACC CCT GCC CGG TTC TCA GGC TCC CTC CTT GGG GGC AAA GCT GCC
    --- --- --- --- --- --- --- --- --- --- --- --- --- --- --- --- --- ---
     H   S   W   T   P   A   R   F   S   G   S   L   L   G   G   K   A   A
    ——————→
               225               234               243               252               261               270
    CTG ACA CTG TCA GGT GTG CAG CCT GAA GAC GAG GCT GAA TAT TAC TGC CTG CTC
    --- --- --- --- --- --- --- --- --- --- --- --- --- --- --- --- --- ---
     L   T   L   S   G   V   Q   P   E   D   E   A   E   Y   Y   C   L   L
                                                                            ←———
               279               288               297               306               315               324
    TAC TAT GGT GGT GCT CAA CTC GTA TTC GGC GGA GGG ACC AAG CTG ACC GTC CTA
    --- --- --- --- --- --- --- --- --- --- --- --- --- --- --- --- --- ---
     Y   Y   G   G   A   Q   L   V   F   G   G   G   T   K   L   T   V   L
    ————————————— CDR3 —————————————→
               333
    CGT CAG CCC   3'
    --- --- ---
     R   Q   P
```

Fig. 10a

LD2-11-VH sequence

```
              9           18          27          36          45          54
5' CAG GTG AAA CTG CTC GAG TCG GGG GGA GGC GTG GTC CAG CCG GGG GGG TCC CTG
   --- --- --- --- --- --- --- --- --- --- --- --- --- --- --- --- --- ---
    Q   V   K   L   L   E   S   G   G   G   V   V   Q   P   G   G   S   L 63          72          81          90          99         108
   AGA CTC TCC TGT GAA GCG TCT GGA TTC ACC CTC AGA AGT TCT GGC ATG CAC TGG
   --- --- --- --- --- --- --- --- --- --- --- --- --- --- --- --- --- ---
    R   L   S   C   E   A   S   G   F   T   L   R   S   S   G   M   H   W
                                                         ←——— CDR1 ———→

117         126         135         144         153         162
   GTC CGC CAG GCT CCT GGC AAG GGG CTG GAG TGG GTG GCA CTT ATA TGG TTT GAT
   --- --- --- --- --- --- --- --- --- --- --- --- --- --- --- --- --- ---
    V   R   Q   A   P   G   K   G   L   E   W   V   A   L   I   W   F   D
                                                             ←——— CDR2

171         180         189         198         207         216
   GGA AGT ATC AGA TCG TAT GCA GAA TCC GTG AAG GGC CGA TTC ACC ATC TCC AGA
   --- --- --- --- --- --- --- --- --- --- --- --- --- --- --- --- --- ---
    G   S   I   R   S   Y   A   E   S   V   K   G   R   F   T   I   S   R
   ————————————— CDR2 ——————————————→

225         234         243         252         261         270
   GAC ACT TCC AAG AAC ACC CTA TAT CTC CAA ATG CGC AGT CTG AGT GCC GAC GAC
   --- --- --- --- --- --- --- --- --- --- --- --- --- --- --- --- --- ---
    D   T   S   K   N   T   L   Y   L   Q   M   R   S   L   S   A   D   D 279         288         297         306         315         324
   ACG GCT GTG TAT TAC TGT GCG AGA GAC AAG GCG GTT CGG GGA ATT AGC AGG TAC
   --- --- --- --- --- --- --- --- --- --- --- --- --- --- --- --- --- ---
    T   A   V   Y   Y   C   A   R   D   K   A   V   R   G   I   S   R   Y
                                    ←——————— CDR3

333         342         351         360         369
   AAC TAT TAC ATG GAC GTC TGG GGC AAA GGG ACC ACG GTC ACC GTC TCC TCA  3'
   --- --- --- --- --- --- --- --- --- --- --- --- --- --- --- ---
    N   Y   Y   M   D   V   W   G   K   G   T   T   V   T   V   S   S
   ——————— CDR3 ———————→
```

Fig. 10b

LD2-11-VL sequence

```
              9            18            27            36            45            54
5' GTG TTG ACC CAG TCT CCA TCC TCC CTG TCT GCA TCT ATA CGA GAC AGA GTC ACC
   --- --- --- --- --- --- --- --- --- --- --- --- --- --- --- --- --- ---
    V   L   T   Q   S   P   S   S   L   S   A   S   I   R   D   R   V   T 63           72            81            90            99           108
   ATC ACT TGC CGG GCA AGT CAG AAC ATT GGC AGT TAT TTA AAT TGG TAT CAG CAC
   --- --- --- --- --- --- --- --- --- --- --- --- --- --- --- --- --- ---
    I   T   C   R   A   S   Q   N   I   G   S   Y   L   N   W   Y   Q   H
                    <---------------- CDR1 ---------------->
             117           126           135           144           153           162
   AAA CCA GGG ACA GCC CCT AAA CTC CTG ATC TAT GCT GTA TCC GCT TTG CAA AGT
   --- --- --- --- --- --- --- --- --- --- --- --- --- --- --- --- --- ---
    K   P   G   T   A   P   K   L   L   I   Y   A   V   S   A   L   Q   S
                                                    <------ CDR2 ------>
             171           180           189           198           207           216
   GGG GTC CCA TCG AGG TTC AGT GGC AGT AGA TCT GGG ACA GAT TTC ACT CTC ACC
   --- --- --- --- --- --- --- --- --- --- --- --- --- --- --- --- --- ---
    G   V   P   S   R   F   S   G   S   R   S   G   T   D   F   T   L   T 225           234           243           252           261           270
   ATC AGC AGT CTG CAA CCT GAA GAT TTT GCA ACT TAC TAC TGT CAA CAG AGT TAC
   --- --- --- --- --- --- --- --- --- --- --- --- --- --- --- --- --- ---
    I   S   S   L   Q   P   E   D   F   A   T   Y   Y   C   Q   Q   S   Y
                                                                <--------
             279           288           297           306           315
   AGT CCC CCG TAC ACT TTC GGC CAG GGG ACC AAC CTG CAG ATC AAA  3'
   --- --- --- --- --- --- --- --- --- --- --- --- --- ---
    S   P   P   Y   T   F   G   Q   G   T   N   L   Q   I   K
    ------ CDR3 ------>
```

Fig. 11a

LD2-14-VH sequence

```
              9              18              27              36              45              54
5' CAG GTG AAA CTG CTC GAG TCT GGG GGA GGC GTG GTC CAG CCG GGG GGG TCC CTG
   --- --- --- --- --- --- --- --- --- --- --- --- --- --- --- --- --- ---
    Q   V   K   L   L   E   S   G   G   G   V   V   Q   P   G   G   S   L 63              72              81              90              99             108
   AGA GTC GCC TGT GTA GCG TCT GGA TTC ACC TTC AGG AAT TTT GGC ATG CAC TGG
   --- --- --- --- --- --- --- --- --- --- --- --- --- --- --- --- --- ---
    R   V   A   C   V   A   S   G   F   T   F   R   N   F   G   M   H   W
                                                        ←——— CDR1 ———→

117             126             135             144             153             162
   GTC CGC CAG GCT CCA GGC AAG GGG CTG GAG TGG GTG GCT TTT ATT TGG TTT GAT
   --- --- --- --- --- --- --- --- --- --- --- --- --- --- --- --- --- ---
    V   R   Q   A   P   G   K   G   L   E   W   V   A   F   I   W   F   D
                                                        ←——— CDR2 ———

171             180             189             198             207             216
   GCA AGT AAT AAA GGA TAT GGA GAC TCC GTT AAG GGC CGA TTC ACC GTC TCC AGA
   --- --- --- --- --- --- --- --- --- --- --- --- --- --- --- --- --- ---
    A   S   N   K   G   Y   G   D   S   V   K   G   R   F   T   V   S   R
   ————————————————— CDR2 ——————————————————→

225             234             243             252             261             270
   GAC AAT TCC AAG AAC ACG CTC TAT CTG CAA ATG AAC GGC CTG AGA GCC GAA GAC
   --- --- --- --- --- --- --- --- --- --- --- --- --- --- --- --- --- ---
    D   N   S   K   N   T   L   Y   L   Q   M   N   G   L   R   A   E   D 279             288             297             306             315             324
   ACG GCT GTA TAT TAT TGT GCG AGA GAG AAG GCG GTT CGG GGA ATT AGT AGA TAC
   --- --- --- --- --- --- --- --- --- --- --- --- --- --- --- --- --- ---
    T   A   V   Y   Y   C   A   R   E   K   A   V   R   G   I   S   R   Y
                                     ←————————————— CDR3 —————————————

333             342             351             360             369
   AAC TAC TAC ATG GAC GTC TGG GGC AAG GGG ACC ACG GTC ACC GTC TCC TCA 3'
   --- --- --- --- --- --- --- --- --- --- --- --- --- --- --- ---
    N   Y   Y   M   D   V   W   G   K   G   T   T   V   T   V   S   S
   ————— CDR3 ————→
```

Fig. 11b

LD2-14-VL sequence

```
           9              18             27             36             45             54
5' GTG ATG ACC CAG TCT CCA TCC TCC CTG TCT GCA TCT GTG GGA GAC AGA GTC ACC
   --- --- --- --- --- --- --- --- --- --- --- --- --- --- --- --- --- ---
    V   M   T   Q   S   P   S   S   L   S   A   S   V   G   D   R   V   T 63             72             81             90             99            108
   ATC ACT TGC CGG GCA AGT CAG AGC ATT ATC AAC AAT TTA AAT TGG TAT CAG CAG
   --- --- --- --- --- --- --- --- --- --- --- --- --- --- --- --- --- ---
    I   T   C   R   A   S   Q   S   I   I   N   N   L   N   W   Y   Q   Q
                    <─────────────── CDR1 ───────────────>
             117            126            135            144            153            162
   AAA CCA GGC AAA GCC CCT GAA CTC CTG ATC TAT GCT GCA TCC AGT TTG CAA AGT
   --- --- --- --- --- --- --- --- --- --- --- --- --- --- --- --- --- ---
    K   P   G   K   A   P   E   L   L   I   Y   A   A   S   S   L   Q   S
                                                <────── CDR2 ──────>
             171            180            189            198            207            216
   GGG GTC CCT TCA AGG TTC CGT GGC AGT GGA TCT GGG AGA GAT TTC ACT CTC ACC
   --- --- --- --- --- --- --- --- --- --- --- --- --- --- --- --- --- ---
    G   V   P   S   R   F   R   G   S   G   S   G   R   D   F   T   L   T 225            234            243            252            261            270
   GTC ACC AGT CTG CAA CCT GAA GAT TTT GCA ACT TAC TAC TGT CAA CAG AGT TAC
   --- --- --- --- --- --- --- --- --- --- --- --- --- --- --- --- --- ---
    V   T   S   L   Q   P   E   D   F   A   T   Y   Y   C   Q   Q   S   Y
                                                                <────
             279            288            297            306            315
   AGT ACC CTG TGG ACG TTC GGC CAA GGG ACC AAG GTG GAA ATC AAA  3'
   --- --- --- --- --- --- --- --- --- --- --- --- --- ---
    S   T   L   W   T   F   G   Q   G   T   K   V   E   I   K
    ─────── CDR3 ───────>
```

Fig. 12a

LD2-17-VH sequence

```
             9              18              27              36              45              54
5'   CAG GTG AAA CTG CTC GAG TCT GGG GGA GGC GTG GTC CAG CCG GGG GGG TCC CTG
     --- --- --- --- --- --- --- --- --- --- --- --- --- --- --- --- --- ---
      Q   V   K   L   L   E   S   G   G   G   V   V   Q   P   G   G   S   L 63             72              81              90              99             108
     AGA CTC TCC TGT GTA GCG TCT GGA TTC ACC TTC AGG AGT TAT GGC ATG CAC TGG
     --- --- --- --- --- --- --- --- --- --- --- --- --- --- --- --- --- ---
      R   L   S   C   V   A   S   G   F   T   F   R   S   Y   G   M   H   W
                                                            ←——————  CDR1  ——————→

117            126             135             144             153             162
     GTC CGC CAG GCT CCA GGC AAG GGC CTG GAG TGG GTG GCT TTT ATA TGG TTT GAT
     --- --- --- --- --- --- --- --- --- --- --- --- --- --- --- --- --- ---
      V   R   Q   A   P   G   K   G   L   E   W   V   A   F   I   W   F   D
                                                                ←——————  CDR2  ——————

171            180             189             198             207             216
     GGA AGT AAT AAA GGA TAT GTA GAC TCC GTG AAG GGC CGA TTC ACC ATC TCC CGA
     --- --- --- --- --- --- --- --- --- --- --- --- --- --- --- --- --- ---
      G   S   N   K   G   Y   V   D   S   V   K   G   R   F   T   I   S   R
     ————————————————————— CDR2 —————————————————————→

225            234             243             252             261             270
     GAC AAT TCC AAG AAC ACG CTC TAT CTG CAA ATG AAG AGC CTG AGA GCC GAG GAC
     --- --- --- --- --- --- --- --- --- --- --- --- --- --- --- --- --- ---
      D   N   S   K   N   T   L   Y   L   Q   M   K   S   L   R   A   E   D 279            288             297             306             315             324
     ACG GCT GTA TAT TAT TGT GCG AGA GAG AAG GCG CTT CGG GGA ATC AGT AGA TAC
     --- --- --- --- --- --- --- --- --- --- --- --- --- --- --- --- --- ---
      T   A   V   Y   Y   C   A   R   E   K   A   L   R   G   I   S   R   Y
                                        ←——————  CDR3  ——————

333            342             351             360             369
     AAC TAT TAC CTG GAC GTC TGG GGC AAG GGG ACC ACG GTC ACC GTC TCC TCA   3'
     --- --- --- --- --- --- --- --- --- --- --- --- --- --- --- --- ---
      N   Y   Y   L   D   V   W   G   K   G   T   T   V   T   V   S   S
     ——————— CDR3 ———————→
```

Fig. 12b

LD2-17-VL sequence

```
           9              18             27             36             45             54
5' GTG ATG ACC CAG TCT CCA TTC TCC CTG TCT GCA TCT GTA GGA GAC AGA GTC ACC
   V   M   T   Q   S   P   F   S   L   S   A   S   V   G   D   R   V   T 63             72             81             90             99            108
   ATC ACT TGC CGG GCA AGT CAG AAC ATT AGG AGT TTT TTA AGT TGG TAT CAG CAG
   I   T   C   R   A   S   Q   N   I   R   S   F   L   S   W   Y   Q   Q
                          ←─────────────── CDR1 ───────────────→
           117            126            135            144            153            162
   AAA CCA GGG ACA GCC CCT AAG CTC CTG ATC TAT GCT GCA TCC AGG TTG CAA AGT
   K   P   G   T   A   P   K   L   L   I   Y   A   A   S   R   L   Q   S
                                                  ←─────────── CDR2 ───────────→
           171            180            189            198            207            216
   GGG GTC CCA TCA AGG TTC AGT GGC AGT GGG TCT GGG ACA GAT TTC ACT CTC ACC
   G   V   P   S   R   F   S   G   S   G   S   G   T   D   F   T   L   T 225            234            243            252            261            270
   ATC AGC ACT CTG CAA CCT GAA GAT TTT GCG ACT TAC TAC TGT CAA CAG AGT TAC
   I   S   T   L   Q   P   E   D   F   A   T   Y   Y   C   Q   Q   S   Y
                                                              ←──────────────
           279            288            297            306            315
   AGT GCC CCT TGG ACG TTC GGC CAA GGG ACC AAG CTG GAA ATC AAA  3'
   S   A   P   W   T   F   G   Q   G   T   K   L   E   I   K
   ──────── CDR3 ────────→
```

Fig. 13a

LD2-20-VH sequence

```
                9              18              27              36              45              54
5' CAG GTG AAA CTG CTC GAG TCT GGG GGA GGC GTG GTC CAG CCG GGG GGG TCC CTG
   --- --- --- --- --- --- --- --- --- --- --- --- --- --- --- --- --- ---
    Q   V   K   L   L   E   S   G   G   G   V   V   Q   P   G   G   S   L 63              72              81              90              99             108
   AGA CTC TCC TGT GTA GCG TCT GGA TTC ACC TCC AGG AGT TAT GGC ATG CAC TGG
   --- --- --- --- --- --- --- --- --- --- --- --- --- --- --- --- --- ---
    R   L   S   C   V   A   S   G   F   T   S   R   S   Y   G   M   H   W
                                                        ←——— CDR1 ———→

117             126             135             144             153             162
   GTC CGC CAG GCT CCA GGC AAG GGC CTG GAG TGG GTG GCT TTT ATA TGG TTT GAT
   --- --- --- --- --- --- --- --- --- --- --- --- --- --- --- --- --- ---
    V   R   Q   A   P   G   K   G   L   E   W   V   A   F   I   W   F   D
                                                            ←——— CDR2

171             180             189             198             207             216
   GGA AGT AAT AAA GGA TAT GTA GAC TCC GTG AAG GGC CGA TTC ACC ATC TCC CGA
   --- --- --- --- --- --- --- --- --- --- --- --- --- --- --- --- --- ---
    G   S   N   K   G   Y   V   D   S   V   K   G   R   F   T   I   S   R
   ————————————————— CDR2 ————————→

225             234             243             252             261             270
   GAC AAT TCC AAG AAC ACG CTC TAT CTG CAA ATG AAG AGC CTG AGA GCC GAG GAC
   --- --- --- --- --- --- --- --- --- --- --- --- --- --- --- --- --- ---
    D   N   S   K   N   T   L   Y   L   Q   M   K   S   L   R   A   E   D 279             288             297             306             315             324
   ACG GCT GTA TAT TAT TGT GCG AGA GAG AAG GCG CTT CGG GGA ATC AGT AGA TAC
   --- --- --- --- --- --- --- --- --- --- --- --- --- --- --- --- --- ---
    T   A   V   Y   Y   C   A   R   E   K   A   L   R   G   I   S   R   Y
                                     ←————————————————— CDR3

333             342             351             360             369
   AAC TAT TAC CTG GAC GTC TGG GGC AAG GGG ACC ACG GTC ACC GTC TCC TCA   3'
   --- --- --- --- --- --- --- --- --- --- --- --- --- --- --- --- ---
    N   Y   Y   L   D   V   W   G   K   G   T   T   V   T   V   S   S
   ————— CDR3 ————→
```

Fig. 13b

LD2-20-VL sequence

```
          9                  18                  27                  36                  45                  54
5' GTG ATG ACC CAG TCT CCA TCC TCC CTG TCT GCA TCT GTA GGA GAC AGA GTC ACC
   --- --- --- --- --- --- --- --- --- --- --- --- --- --- --- --- --- ---
    V   M   T   Q   S   P   S   S   L   S   A   S   V   G   D   R   V   T 63                  72                  81                  90                  99                 108
   ATC ACT TGC CGG GCA AGT CAG AGC ATT AGC AGC TAT TTA AAT TGG TAT CAG CAG
   --- --- --- --- --- --- --- --- --- --- --- --- --- --- --- --- --- ---
    I   T   C   R   A   S   Q   S   I   S   S   Y   L   N   W   Y   Q   Q
                    ←─────────────── CDR1 ───────────────→

117                 126                 135                 144                 153                 162
   AAA CCA GGG AAA GCC CCT AAG CTC CTG ATC TAT GCT GCA TCC AGT TTG CAA AGT
   --- --- --- --- --- --- --- --- --- --- --- --- --- --- --- --- --- ---
    K   P   G   K   A   P   K   L   L   I   Y   A   A   S   S   L   Q   S
                                                    ←─────────── CDR2 ───────────→

171                 180                 189                 198                 207                 216
   GGG GTC CCA TCA AGG TTC AGT GGC AGT GGA TCT GGG ACA GAT TTC ACT CTC ACC
   --- --- --- --- --- --- --- --- --- --- --- --- --- --- --- --- --- ---
    G   V   P   S   R   F   S   G   S   G   S   G   T   D   F   T   L   T 225                 234                 243                 252                 261                 270
   ATC AGC AGT CTG CAA CCT GAA GAT TTT GCA ACT TAC TAC TGT CAA CAG AGT TAC
   --- --- --- --- --- --- --- --- --- --- --- --- --- --- --- --- --- ---
    I   S   S   L   Q   P   E   D   F   A   T   Y   Y   C   Q   Q   S   Y
                                                                        ←──

279                 288                 297                 306                 315
   AGT ACC CGA TTC ACT TTC GGC CCT GGG ACC AAA GTG GAT ATC AAA  3'
   --- --- --- --- --- --- --- --- --- --- --- --- --- --- ---
    S   T   R   F   T   F   G   P   G   T   K   V   D   I   K
   ──────── CDR3 ────────→
```

Fig. 14a

LD1-6-17-VH sequence

```
                9                18               27               36               45               54
5' CAG GTG AAA CTG CTC GAG TCT GGG GGA GGC GTG GTC CAG CCT GGG AGG TCC CTG
   --- --- --- --- --- --- --- --- --- --- --- --- --- --- --- --- --- ---
    Q   V   K   L   L   E   S   G   G   G   V   V   Q   P   G   R   S   L 63               72               81               90               99              108
   AGA CTT TCC TGT GCA GCG TCT GGA TTT ACC TTC AGT AGC TAT GGC ATG CAC TGG
   --- --- --- --- --- --- --- --- --- --- --- --- --- --- --- --- --- ---
    R   L   S   C   A   A   S   G   F   T   F   S   S   Y   G   M   H   W
                                                          ←——— CDR1 ———→

117              126              135              144              153              162
   GTC CGC CAG GCT CCA GGC AAG GGG CTG GAG TGG GTG GCA GAT ATA TGG TTT GAT
   --- --- --- --- --- --- --- --- --- --- --- --- --- --- --- --- --- ---
    V   R   Q   A   P   G   K   G   L   E   W   V   A   D   I   W   F   D
                                                      ←——— CDR1 ———

171              180              189              198              207              216
   GGA GGT AAT AAA CAT TAT GCA GAC TTC GTG AAG GGC CGA TTC ACC ATC TCC AGA
   --- --- --- --- --- --- --- --- --- --- --- --- --- --- --- --- --- ---
    G   G   N   K   H   Y   A   D   F   V   K   G   R   F   T   I   S   R
   ————————————————— CDR2 ———————————————→

225              234              243              252              261              270
   GAC AAT TCC AAG AAC ACG GTG TAT CTA CAA ATG AAC AGC CTG AGA GTC GAG GAC
   --- --- --- --- --- --- --- --- --- --- --- --- --- --- --- --- --- ---
    D   N   S   K   N   T   V   Y   L   Q   M   N   S   L   R   V   E   D 279              288              297              306              315              324
   ACG GCT GTG TAT TAC TGT GCG AGG GAT TAC TAT AGC GTT ACT AAG AAA CTC AGA
   --- --- --- --- --- --- --- --- --- --- --- --- --- --- --- --- --- ---
    T   A   V   Y   Y   C   A   R   D   Y   Y   S   V   T   K   K   L   R
                                    ←——————— CDR3 ———————

333              342              351              360              369              378
   CTC CAC TAC TAC TAC TAC ATG GAC GTC TGG GGC AAA GGG ACC ACG GTC ACC GTC
   --- --- --- --- --- --- --- --- --- --- --- --- --- --- --- --- --- ---
    L   H   Y   Y   Y   Y   M   D   V   W   G   K   G   T   T   V   T   V
   ——————— CDR3 ———————→

TCC TCA 3'
   --- ---
    S   S
```

Fig. 14b

LD1-6-17-VL sequence

```
          9              18              27              36              45              54
5' GTG ATG ACC CAG TCT CCA TCC TCC CTG TCT GCA TCT GTA GGA GAC AGA GTC ACC
   --- --- --- --- --- --- --- --- --- --- --- --- --- --- --- --- --- ---
    V   M   T   Q   S   P   S   S   L   S   A   S   V   G   D   R   V   T 63              72              81              90              99             108
   ATC ACT TGC CGG GCA AGT CAG GGC ATT AGA AAT GAT TTA ACC TGG TAT CAG CAA
   --- --- --- --- --- --- --- --- --- --- --- --- --- --- --- --- --- ---
    I   T   C   R   A   S   Q   G   I   R   N   D   L   T   W   Y   Q   Q
                       ←─────────────── CDR1 ───────────────→

117             126             135             144             153             162
   AAA CCA GGG AAA GCC CCT AAG CTC CTG ATC TAT GCT GCA TCC AAT TTA CAA AGT
   --- --- --- --- --- --- --- --- --- --- --- --- --- --- --- --- --- ---
    K   P   G   K   A   P   K   L   L   I   Y   A   A   S   N   L   Q   S
                                                   ←─────────── CDR2 ───────→

171             180             189             198             207             216
   GGG GTC CCA TCA AGG TTC AGC GGC AGT GGA TCT GGC ACA GAT TTC ACT CTC ACC
   --- --- --- --- --- --- --- --- --- --- --- --- --- --- --- --- --- ---
    G   V   P   S   R   F   S   G   S   G   S   G   T   D   F   T   L   T 225             234             243             252             261             270
   ATC AGC AGC CTG CAG CCT GAA GAT TTT GCA ACT TAT TAC TGT CTA CAA GAT AAC
   --- --- --- --- --- --- --- --- --- --- --- --- --- --- --- --- --- ---
    I   S   S   L   Q   P   E   D   F   A   T   Y   Y   C   L   Q   D   N
                                                               ←──────────────

279             288             297             306             315
   AAT TTC CCG TAC ACT TTT GGC CAG GGG ACC AAG CTG GAG ATC AAA  3'
   --- --- --- --- --- --- --- --- --- --- --- --- --- ---
    N   F   P   Y   T   F   G   Q   G   T   K   L   E   I   K
   ─────── CDR3 ───────→
```

Fig. 15a

LD1/2-6-3-VH sequence

```
              9            18           27           36           45           54
5' CAG GTG AAA CTG CTC GAG TCT GGG GGA GGC GTG GTC CAG CCG GGG GGG TCC CTG
   --- --- --- --- --- --- --- --- --- --- --- --- --- --- --- --- --- ---
    Q   V   K   L   L   E   S   G   G   G   V   V   Q   P   G   G   S   L 63           72           81           90           99          108
   AGA GTC GCC TGT GTA GCG TCT GGA TTC ACC TTC AGG AAT TTT GGC ATG CAC TGG
   --- --- --- --- --- --- --- --- --- --- --- --- --- --- --- --- --- ---
    R   V   A   C   V   A   S   G   F   T   F   R   N   F   G   M   H   W
                                                         ←————— CDR1 —————→
            117          126          135          144          153          162
   GTC CGC CAG GCT CCA GGC AAG GGG CTG GAG TGG GTG GCT TTT ATT TGG TTT GAT
   --- --- --- --- --- --- --- --- --- --- --- --- --- --- --- --- --- ---
    V   R   Q   A   P   G   K   G   L   E   W   V   A   F   I   W   F   D
                                                         ←————— CDR2 ——————
            171          180          189          198          207          216
   GCA AGT AAT AAA GGA TAT GGA GAC TCC GTT AAG GGC CGA TTC ACC GTC TCC AGA
   --- --- --- --- --- --- --- --- --- --- --- --- --- --- --- --- --- ---
    A   S   N   K   G   Y   G   D   S   V   K   G   R   F   T   V   S   R
   —————————————— CDR2 ——————————→
            225          234          243          252          261          270
   GAC AAT TCC AAG AAC ACG CTC TAT CTG CAA ATG AAC GGC CTG AGA GCC GAA GAC
   --- --- --- --- --- --- --- --- --- --- --- --- --- --- --- --- --- ---
    D   N   S   K   N   T   L   Y   L   Q   M   N   G   L   R   A   E   D 279          288          297          306          315          324
   ACG GCT GTA TAT TAT TGT GCG AGA GAG AAG GCG GTT CGG GGA ATT AGT AGA TAC
   --- --- --- --- --- --- --- --- --- --- --- --- --- --- --- --- --- ---
    T   A   V   Y   Y   C   A   R   E   K   A   V   R   G   I   S   R   Y
                                 ←————————————— CDR3 ——————————————————————
            333          342          351          360          369
   AAC TAC TAC ATG GAC GTC TGG GGC AAG GGG ACC ACG GTC ACC GTC TCC TCA 3'
   --- --- --- --- --- --- --- --- --- --- --- --- --- --- --- --- ---
    N   Y   Y   M   D   V   W   G   K   G   T   T   V   T   V   S   S
   ——————— CDR3 ——————————→
```

Fig. 15b

LD1/2-6-3-VL sequence

```
              9              18             27             36             45             54
5' GTG ATG ACC CAG TCT CCA TCC TCC CTG TCT GCA TCT GTA GGA GAC AGA GTC ACC
   --- --- --- --- --- --- --- --- --- --- --- --- --- --- --- --- --- ---
    V   M   T   Q   S   P   S   S   L   S   A   S   V   G   D   R   V   T 63             72             81             90             99            108
   ATC ACT TGC CGG GCA AGT CAG AGC ATT ATC AGA TAT TTA AAT TGG TAT CAG CAC
   --- --- --- --- --- --- --- --- --- --- --- --- --- --- --- --- --- ---
    I   T   C   R   A   S   Q   S   I   I   R   Y   L   N   W   Y   Q   H
                    ←─────────────── CDR1 ───────────────→
             117            126            135            144            153            162
   AAA CCA GGG AAA GCC CCT AAG CTC CTG ATC CAT ACT GCA TCC AGT TTG CAA AGT
   --- --- --- --- --- --- --- --- --- --- --- --- --- --- --- --- --- ---
    K   P   G   K   A   P   K   L   L   I   H   T   A   S   S   L   Q   S
                                                ←─────────── CDR2 ───────────→
             171            180            189            198            207            216
   GGG GTC CCG TCA AGG TTC AGT GGC AGT GTA TCT GGG ACA GAT TTC ACT CTC ACC
   --- --- --- --- --- --- --- --- --- --- --- --- --- --- --- --- --- ---
    G   V   P   S   R   F   S   G   S   V   S   G   T   D   F   T   L   T 225            234            243            252            261            270
   ATC AGC AGT CTG CAA CCT GAA GAT TTT GCA ACT TAC TAC TGT CAA CAG AGT TAC
   --- --- --- --- --- --- --- --- --- --- --- --- --- --- --- --- --- ---
    I   S   S   L   Q   P   E   D   F   A   T   Y   Y   C   Q   Q   S   Y
                                                                ←──────────
             279            288            297            306            315
   ACT ACC CCG TAC ACT TTT GGC CAG GGG ACC AAG CTG CAG ATC AAA  3'
   --- --- --- --- --- --- --- --- --- --- --- --- --- --- ---
    T   T   P   Y   T   F   G   Q   G   T   K   L   Q   I   K
    ─────── CDR3 ───────→
```

Fig. 16a

LD1/2-6-33-VH sequence

```
         9              18              27              36              45              54
5' CAG GTG AAA CTG CTC GAG TCT GGG GGA GGC GTG GTC CAG CCG GGG GGG TCC CTG
    Q   V   K   L   L   E   S   G   G   G   V   V   Q   P   G   G   S   L 63             72              81              90              99             108
   AGA GTC GCC TGT GTA GCG TCT GGA TTC ACC TTC AGG AAT TTT GGC ATG CAC TGG
    R   V   A   C   V   A   S   G   F   T   F   R   N   F   G   M   H   W
                                                         ←———— CDR1 ————→

117            126             135             144             153             162
   GTC CGC CAG GCT CCA GGC AAG GGG CTG GAG TGG GTG GCT TTT ATT TGG TTT GAT
    V   R   Q   A   P   G   K   G   L   E   W   V   A   F   I   W   F   D
                                                                 ←——— CDR2 ———

171            180             189             198             207             216
   GCA AGT AAT AAA GGA TAT GGA GAC TCC GTT AAG GGC CGA TTC ACC GTC TCC AGA
    A   S   N   K   G   Y   G   D   S   V   K   G   R   F   T   V   S   R
   ———————————— CDR2 ————————————→

225            234             243             252             261             270
   GAC AAT TCC AAG AAC ACG CTC TAT CTG CAA ATG AAC GGC CTG AGA GCC GAA GAC
    D   N   S   K   N   T   L   Y   L   Q   M   N   G   L   R   A   E   D 279            288             297             306             315             324
   ACG GCT GTA TAT TAT TGT GCG AGA GAG AAG GCG GTT CGG GGA ATT AGT AGA TAC
    T   A   V   Y   Y   C   A   R   E   K   A   V   R   G   I   S   R   Y
                                        ←———————————— CDR3 ————————————

333            342             351             360             369
   AAC TAC TAC ATG GAC GTC TGG GGC AAG GGG ACC ACG GTC ACC GTC TCC TCA 3'
    N   Y   Y   M   D   V   W   G   K   G   T   T   V   T   V   S   S
   ———————— CDR3 ————————→
```

Fig. 16b

LD1/2-6-33-VL sequence

```
              9               18              27              36              45              54
5' GTG ATG ACC CAG TCT CCA TCC TTC CTG TCT GCA TCT GTA GGA GAC AGA GTC ACC
   --- --- --- --- --- --- --- --- --- --- --- --- --- --- --- --- --- ---
    V   M   T   Q   S   P   S   F   L   S   A   S   V   G   D   R   V   T 63              72              81              90              99             108
   ATC ACT TGC CGG GCA AGT CAG AGC ATT ATC AGA TAT TTA AAT TGG TAT CAG CAC
   --- --- --- --- --- --- --- --- --- --- --- --- --- --- --- --- --- ---
    I   T   C   R   A   S   Q   S   I   I   R   Y   L   N   W   Y   Q   H
                   ←─────────────── CDR1 ───────────────→

117             126             135             144             153             162
   AAA CCA GGG AAA GCC CCT AAG CTC CTG ATC CAT GCT GCA TCC AGT TTG CAA AGT
   --- --- --- --- --- --- --- --- --- --- --- --- --- --- --- --- --- ---
    K   P   G   K   A   P   K   L   L   I   H   A   A   S   S   L   Q   S
                                                       ←─────── CDR2 ───────→

171             180             189             198             207             216
   GGG GTC CCG TCA AGG TTC AGT GGC AGT GTA TCT GGG ACA GAT TTC ACT CTC ACC
   --- --- --- --- --- --- --- --- --- --- --- --- --- --- --- --- --- ---
    G   V   P   S   R   F   S   G   S   V   S   G   T   D   F   T   L   T 225             234             243             252             261             270
   ATC AGC AGT CTG CAA CCT GAA GAT TTT GCA ACT TAC TAC TGT CAA CAG AGT TAC
   --- --- --- --- --- --- --- --- --- --- --- --- --- --- --- --- --- ---
    I   S   S   L   Q   P   E   D   F   A   T   Y   Y   C   Q   Q   S   Y
                                                              ←─────────────

279             288             297             306             315
   ACT ACC CCG TAC ACT TTT GGC CAG GGG ACC AAG CTG CAG ATC AAA  3'
   --- --- --- --- --- --- --- --- --- --- --- --- --- --- ---
    T   T   P   Y   T   F   G   Q   G   T   K   L   Q   I   K
   ─────── CDR3 ───────→
```

The pComb3 Expression System

POLYPEPTIDES CAPABLE OF FORMING ANTIGEN BINDING STRUCTURES WITH SPECIFICITY FOR THE RHESUS D ANTIGENS, THE DNA ENCODING THEM AND THE PROCESS FOR THEIR PREPARATION AND USE

This invention relates to polypeptides forming antigen binding structures with specificity for Rhesus D antigens and especially to Fab molecules with specificity for the Rhesus D antigen. The invention also relates to their application to provide pharmacological and diagnostic compositions. The above Fab fragments when genetically engineered to be part of complete antibodies are useful for the prophylaxis of hemolytic disease of the newborn (HDN). This invention provides the novel DNA and amino acid sequences of the above polypeptides.

Thus, the antibodies can be used for the protection of Rhesus negative women before or immediately after the birth of a Rhesus positive child to prevent HDN in subsequent pregnancies.

The invention also includes the application of the said Fab molecules either alone or in combination with Fc constant regions as complete antibodies for the purposes of treating other illnesses which might benefit from anti-Rhesus D immunoglobulin e.g. treatment of idiopathic thrombocytopenic purpura (ITP).

In addition anti-Rhesus D immunoglobulin can be used after mistransfusions of Rhesus positive blood to Rhesus negative recipients in order to prevent sensitization to the Rhesus D antigen. Further the invention relates to the application of these Fab fragments and antibodies as diagnostic reagents.

HDN is the general designation for hemolytic anemia of fetuses and newborn babies caused by antibodies of the mother. These antibodies are directed against antigens on the surface of the fetal erythrocytes. These antigens can belong to the Rhesus, ABO or other blood group systems.

The Rhesus blood group system includes 5 major antigens: D, C, c, E and e (Issitt, P. D., Med. Lab. Sci. 45:395, 1988). The D antigen is the most important of these antigens as it is highly immunogenic eliciting anti-Rhesus D antibodies during Rhesus incompatible pregnancies and following transfusion of Rhesus incompatible blood. The D antigen is found in approximately 85% of Caucasians in Europe and those individuals are said to be Rhesus positive. Individuals lacking the D antigen are called Rhesus negative. The expression of the D antigen can vary due to either low antigen density, hereafter known as weak D or $D^u$, or due to partial antigenicity, hereafter known as partial D antigens.

The Rhesus D antigen, a membrane protein of the erythrocyte, has recently been cloned and its primary structure described (Le Van Kim, C., et al., PNAS 89:10925, 1992). Modeling studies suggest that the Rhesus D antigen has 12 transmembrane domains with only very short connecting regions extending outside the cell membrane or protruding into the cytoplasm.

The partial D phenotypes were first identified in people who carried D antigen on their red cells but who had an alloanti-D in their sera (Rose, R. R. and Sanger, R., Blood groups in man, Blackwell Scientific, Oxford, U.K. 1975; Tippett, P. et al., Vox Sanguinis. 70:123, 1996). This can be explained by regarding the D antigen as a mosaic structure with at least 9 different epitopes (epD1 to epD9). Thus in some D variant people the red cells lack part of this mosaic and antibodies are made to the missing D epitopes. Rhesus positive individuals that make antibodies against partial D antigens have been classified into six main different categories ($D^{II}$ to $D^{VII}$) each having a different abnormality in the D antigen. More recently it has been shown that these D categories gave different patterns of reaction when tested against panels of human monoclonal anti-D antibodies (Tippett, P., et al., Vox Sanguinis. 70:123, 1996). The different reaction patterns identified the 9 epitopes and so define the different partial D categories. The number of epitopes present on the D antigen varies from one partial D category to another with the $D^{VI}$ category expressing the least, epD3, 4 and 9. The $D^{VI}$ category is clinically important as a $D^{VI}$ woman can be immunized strongly enough to cause hemolytic disease of the newborn.

The prophylactic efficacy of anti-RhD IgG for prevention of hemolytic disease of the newborn is well established and has been in routine use for many years. As a result this severe disease has become a rarity. Nevertheless the underlying cause of the disease, i.e. RhD incompatibility between a RhD negative mother carrying a RhD positive child still remains and thus requires a continual supply of therapeutic anti-RhD IgG.

In recent years the assurance of a continual supply of anti-RhD IgG has become an increasing problem. The pool of available hyperimmune serum from alloimmunized multiparous Rhesus negative women has drastically decreased due to the success of prophylactic anti-RhD. Thus the current methods of production require repeated immunization of an increasingly reluctant pool of donors for the production of high titer antiserum (Selinger, M., Br. J. Obstet. Gynaecol. 98:509, 1991). There are also associated risk factors and technical problems such as the use of Rhesus positive red blood cells for repeated immunization carrying the risk of transmission of viral diseases like hepatitis B, AIDS and other as yet unknown viruses (Hughes-Jones, N. C., Br. J. Haematol. 70:263, 1988). Therefore an alternative method for production of anti-RhD antibodies is required.

In the past few years various alternative sources of hyperimmune serum have been tried but all are associated with disadvantages. Epstein Barr Virus (EBV) transformation of lymphocytes creating B lymphoblastoid cell lines that secrete specific antibody including against the Rhesus D antigen (Crawford et al., Lancet. 386:Feb. 19th, 1983) are unstable and require extensive cloning. Also due to the low transformation efficiencies (1–3% of B cells) only a restricted range of antibody specificities can be obtained from the potential repertoire. Additionally it seems that mice do not respond to the Rhesus D antigen and thus no murine monoclonal antibodies are available which could be used for producing chimaeric or humanised antibodies. Until recently the only other alternative was production of human antibodies by the hybridoma technique which was also restricted by the lack of a suitable human myeloma cell fusion partner (Kozbor, D. and Roder, J. C., Immunol. Today. 4:72, 1983).

It is thus the object of the present invention to provide Fab fragments having a reactivity against the Rhesus D antigen as well as complete antibodies comprising the Fab fragments which are free from the above mentioned drawbacks.

In the last few years the technique of repertoire cloning and the construction of phage display libraries has opened up new possibilities to produce human antibodies of defined specificity (Williamson, R. A. et al., PNAS 90:4141, 1993). These methods were thus applied to the preparation of polypeptides capable of forming antigen binding structures with specificity for Rhesus D antigens, especially of Fab fragments having an activity against Rhesus D and partial D antigens.

The generation of human antibodies by repertoire cloning as described in recent years (Barbas III, C. F. and Lerner, R. A., Companion Methods Enzymol. 2:119, 1991) is based on isolating mRNA from peripheral B cells. This method offers the tools to isolate natural antibodies, autoantibodies or antibodies generated during the course of an immune response (Zebedee, S. L., et al., PNAS 89:3175, 1992; Vogel, M. et al., Eur. J. Immunol. 24:1200, 1994). This method relies on constructing a recombinant antibody library from a particular donor starting from the mRNA coding for immunoglobulin (1 g) molecules. As only the peripheral blood lymphocytes (PBL) can be isolated from a donor the chances of finding specific antibody producing B cells in the periphery are increased if an individual is boosted with the desired antigen shortly before harvesting the PBL (Persson, M. A. A., et al., PNAS 88:2432, 1991). The total RNA is then isolated and the mRNA of the Ig repertoire can be cloned using Ig specific primers in the polymerase chain reaction (PCR) followed by the co-expression of heavy and light chains of the Ig molecule on the surface of a filamentous phage particle thereby forming an "organism" that in analogy to a B cell can bind to an antigen. In the literature this method is also known as the combinatorial approach as it allows the independent combining of heavy and light chains to form a functional Fab antibody fragment attached to one of the tail proteins, called pIII, of a filamentous phage. Phages carrying the Fab molecules (hereafter known as Phab particles) are selected for the desired antigen specificity, by a process known as bio-panning. The antigen can be applied to a solid support, specific Phab bind to the antigen whilst non specific Phab are washed away and finally the specific Phab are eluted from the solid support. The specific Phab are then amplified in bacteria, allowed to re-bind to the antigen on the solid support and the whole process of bio-panning is repeated.

The successive rounds of panning and amplification of selected Phab in bacteria result in an enrichment of specific Phab that can be seen from a rise in titer of colony forming units (cfu) plated out after each round of panning. Our previous experience and published data indicate that specific phage can usually be detected after 4 to 6 panning rounds (Vogel, M. et al., Eur. J. Immunol. 24:1200, 1994). In the above cited related art there is, however, no hint that the indicated steps can be used for a successful preparation of Fab fragments of anti-Rh D antibodies.

In the appended FIGS. 1a to 16b; DNA sequences coding for variable regions (V regions) of anti Rh D Fab fragments and the corresponding polypeptide sequences are disclosed.

Figure 17:
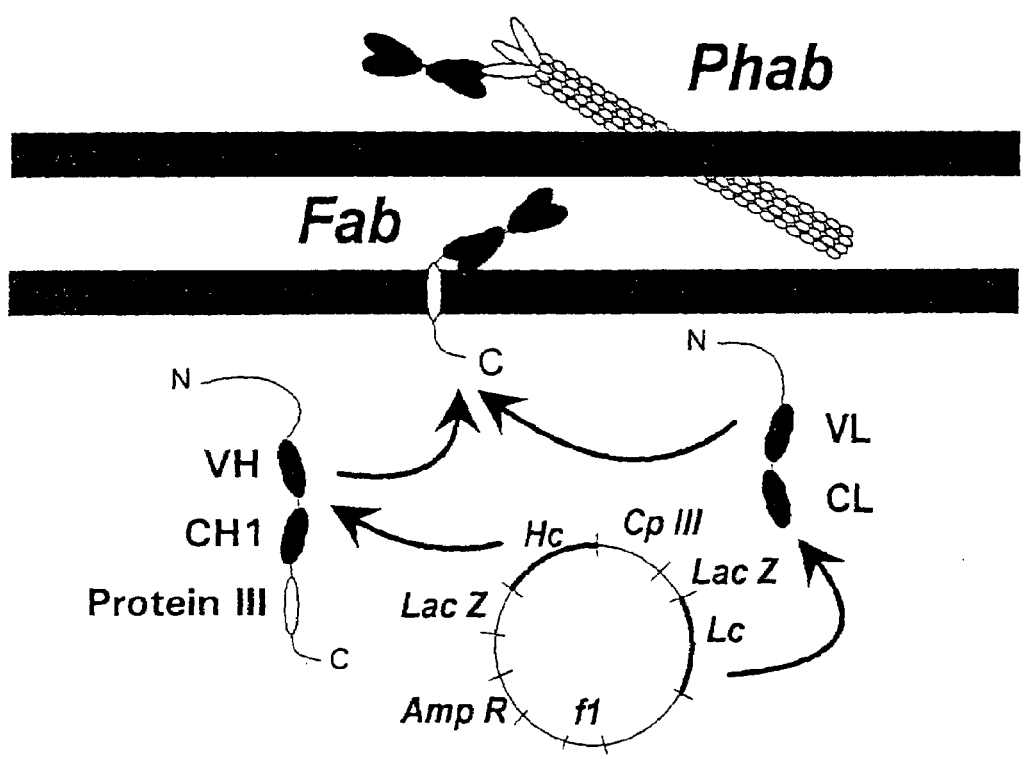
FIG. 17 shows the pComb3 expression system used according to the present invention.
Figures 18, 19:
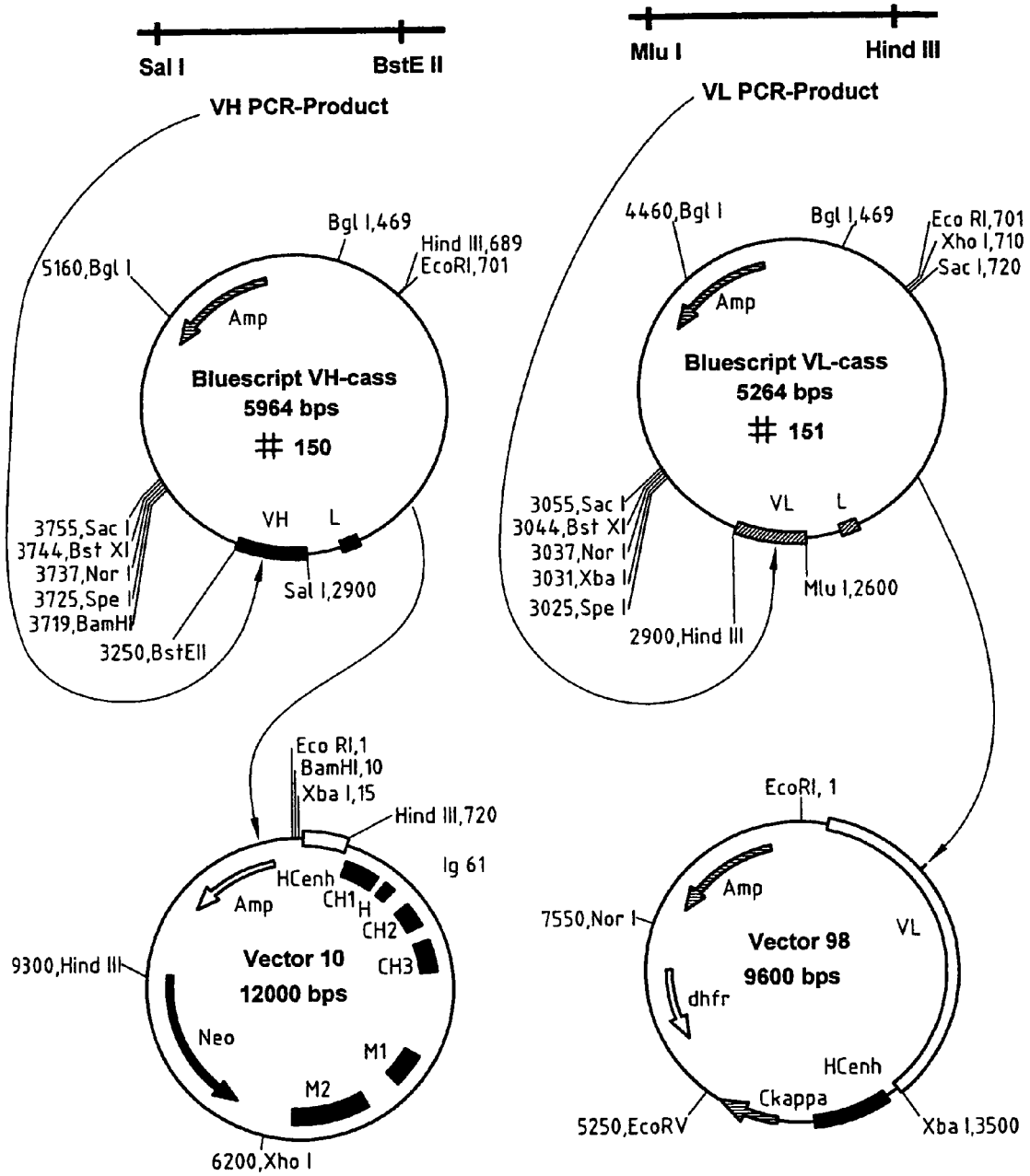
FIGS. 18 and 19 show the separate preparation of genes of the heavy and light chains of the complete antibody according to the description in example 6.

Subjects of the present invention are polypeptides capable of forming antigen binding structures with specificity for Rhesus D antigens according to the definition of claim 1. The table in claim 1 refers to the appended figures. The identification number for each sequence is given. The locations of the Rhesus D specific CDR1 (complementarity determining region 1), CDR2 and CDR3 regions are indicated in the figures and according to base pair number in the table of claim 1. Preferred polypeptides according to the invention are anti-Rhesus D antibodies which include the variable regions of the heavy and light chains according to the sequences given in FIGS. 1a–16b. The FIGS. 1a, 2a, . . . 16a are related to the variable regions of the heavy chain and the FIGS. 1b, 2b, . . . 16b are related to the variable regions of the light chain.

Further subjects of the present invention are the DNA sequences coding for antigen binding polypeptides according to the definition of claim 6. Prefered DNA sequences are those coding for variable regions of Fab fragments of anti-Rh D antibodies according to the FIGS. 1a–16b. The FIGS. 1a, 2a, . . . 16a are related to the heavy chain and the FIGS. 1b, 2b . . . . 16b are related to the light chain.

A further subject of the present invention is a process for preparing recombinant Fab polypeptides according to the definition in claim 11.

A further subject of the present invention is a process for the selection of recombinant polypeptides according to claim 12.

Further subjects of the present invention are anti-Rh D antibodies according to the definition of claim 14, preferably anti-Rh D immunoglobulin molecules comprising the heavy and light chain variable regions according to the FIGS. 1a to 16b combined with known heavy and light chain constant regions.

Further subjects of the present invention are pharmaceutical and diagnostic compositions comprising polypeptides, anti-Rh D antibodies or Fab fragments according to the invention.

The total re-amplified Phab population obtained after each panning can be tested for specificity using various methods such as ELISA and immunodot assays. It is also defined by the nature of the antigen e.g. anti-Rhesus D Phabs are detected by indirect haemagglutination using a rabbit anti-phage antibody or equivalent Coombs reagent as the cross linking antibody. Once a total Phab population has been identified as positive for the desired antigen, individual Phab clones are isolated and the DNA coding for the desired Fab molecules is sequenced. Individual Fab can then be produced by use of the pComb3 expression system which is illustrated in FIG. 16. In this system the gIII gene, coding for the tail protein pIII, is cut out from the phagemid vector pComb3. This allows production of soluble Fab in the bacterial periplasm. Such individual Fab fragments can then be tested for antigen specificity.

The phage display approach has also been used as a means of rescuing monoclonal antibodies from unstable hybridoma cell lines. This has been reported for anti-Rhesus D antibodies (Siegel, D. L. and Silberstein, L. E., Blood. 83:2334, 1994; Dziegiel, M. et al., J. Immunol. Methods. 182:7, 1995). A phage display library constructed from non-immunized donors has also been used to select Fv fragments (i.e. variable regions of heavy and light chains, $V_H$ and $V_L$) specific for human blood group antigens which included one Fv fragment reacting against the Rhesus D antigen (Marks, J. D. et al., Biotechnology. 11:1145, 1993).

Important considerations when constructing combinatorial libraries are the source of cells used for RNA extraction and the nature of the antigen used for panning. Therefore, this invention uses a hyperimmune donor who was boosted i.v. with Rhesus D$^+$ red blood cells (rbc). The PBL of the donor were harvested at +5 and +18 days after the i.v. boost and were used to construct 2 combinatorial libraries hereafter known as library D1 (LD1) and library D2 (LD2) respectively. Double immunofluorescence analysis of the harvested PBL, using the markers CD20 and CD38 for pan B cells and lymphoblastoid cells respectively, showed a higher than normal percentage of lymphoblastoid B cells, of plasma cell morphology. The high number of plasma cells found in the peripheral blood is most unusual as normally there are less than 1% in the periphery and probably indicates that the donor had a high percentage of circulating B cells with specificity for the Rhesus D antigen.

After construction of the library, the selection of Phabs specific for the Rhesus D antigen was achieved by biopanning on fresh whole rbc of phenotype R1R1 (CDe/CDe) i.e. the reference cells used for Rhesus D typing. This was necessary since the Rhesus D antigen, an integral membrane protein of 417 amino acids (Le Van Kim, C. et al, PNAS 89:10925, 1992), loses its immunogenicity during purification (Paradis, G. et al, J. Immunol. 137:240, 1986) and therefore a chemically purified D antigen cannot be bound to a solid phase for selection of immunoreactive Phabs as for other antigen specificities previously selected in this system (Vogel, M. et al., Eur. J. Immunol. 24:1200, 1994). Modelling studies have suggested that only very short connecting regions of the Rhesus D antigen extend outside the cell membrane or protrude into the cytoplasm (Chérif-Zahar, B. et al, PNAS 87:6243, 1990). Thus the parts of the RhD antigen visible to antibodies are relatively restricted and may be under conformational constraint. This aspect of the Rhesus D antigen becomes even more important when considering selection of Phabs with reactivity against the partial D phenotypes which essentially lack certain defined epitopes of the D membrane protein (Mouro, I. et al, Blood. 83:1129, 1994).

Furthermore, since whole rbc do not only express the D antigen, a series of negative absorptions had to be performed on Rhesus D negative rbc in order to absorb out those Phabs reacting with the other antigenic proteins found on the rbc.

This panning procedure performed on Phabs coming from both LD1 and LD2 librairies resulted in the isolation of 6 different Fab producing clones from library LD1, 8 different Fab producing clones from library LD2 and 2 Fab producing clones from the pooled libraries LD1 and LD2.

The nomenclature and the figures where the sequences are listed are given in table 1.

TABLE 1

| LIBRARY LD1 Clone No. | $V_H$-Sequence Figure | $V_L$-Sequence Figure | LIBRARY LD2 Clone No. | $V_H$-Sequence Figure | $V_L$-Sequence Figure |
|---|---|---|---|---|---|
| LD1-40 | 1a | 1b | LD2-1 | 6a | 6b |
| LD1-52 | 2a | 2b | LD2-4 | 7a | 7b |
| LD1-84 | 3a | 3b | LD2-5 | 8a | 8b |
| LD1-110 | 4a | 4b | LD2-10 | 9a | 9b |
| LD1-117 | 5a | 5b | LD2-11 | 10a | 10b |
|  |  |  | LD2-14 | 11a | 11b |
|  |  |  | LD2-17 | 12a | 12b |
|  |  |  | LD2-20 | 13a | 13b |

The above Fab clones show exclusive reactivity against the Rhesus D antigen, 3 of 5 $D^u$ rbc tested and agglutinating reactivity against the Partial D phenotypes as follows: Rh33, DIII, DIVa, DIVb, DVa, DVII.

However, using the above mentioned R1R1 rbc for panning of the Phabs, no clones were isolated which reacted against the Partial DVI phenotype. As the serum of the original hyperimmune donor tested at the time of construction of the recombinant library, was known to react against the DVI phenotype the recombinant library should also contain the anti-DVI specificity.

In order to select for the DVI reactivity the panning conditions were changed in that different cells were used. A special donor whose rbc had been typed and were known to express the Partial DVI phenotype was used as the source of cells for re-panning the LD1 and LD2 libraries. This second series of pannings was essentially performed in the same way as the first series except for the substitution of DVI rbc for R1R1 rbc and the addition of bromelase treatment to the DVI rbc. The DVI phenotype expresses the least number of Rhesus D epitopes and it is therefore difficult to make antibodies against it. It has been reported that only 15% of unselected polyclonal anti-D and 35% of selected anti-D made by Rhesus D negative subjects reacted with DVI+ cells (Mouro, I. et al, Blood. 83:1129, 1994). Bromelase treatment which removes N—acetylneuraminic acid (sialic acid) from the rbc membrane, was performed in order to render the Rhesus DVI epitopes more accessible during the panning with the pre-absorbed Phabs.

This second series of pannings on the LD1 library resulted in 1 Fab producing clone LD1-6-17. The nomenclature is given in table 2.

TABLE 2

| LIBRARY LD1 | $V_H$-Sequence figure | $V_L$-Sequence figure |
|---|---|---|
| Clone No: LD1-6-17 | 14a | 14b |

However this clone was reacting with Rhesus alleles C and E and showing a false positive reaction with DVI positive rbc. This was also due to the phenotype of the DVI donor (Cc DVI ee) who expressed the C allele which was not absorbed out by the Rhesus negative rbc (ccddee).

Thus a third series of pannings on a pool of the LD1 and LD2 libraries was performed using different rbc for the absorption phase. After 6 rounds of panning using both bromelase treated and non treated rbc for both the absorption steps and the elution from DVI positive rbc a total population of Phabs was obtained which reacted exclusively with rbc of phenotype R1R1 (CCDDee) and 2 different donors expressing the DVI variant.

This third series of pannings on the LD1 and LD2 librairies resulted in 2 Fab producing clones reacting with DVI+ rbc. The nomenclature is given in table 3.

TABLE 3

| LIBRARY LD1/LD2 | $V_H$-Sequence figure | $V_L$-Sequence figure |
|---|---|---|
| Clone No: LD1/2-6-3 | 15a | 15b |
| Clone No: LD1/2-6-33 | 16a | 16b |

Thus a total of 16 different anti-Rhesus D Fab clones have been isolated. The DNA from these clones has been isolated and sequenced using Fluorescent Cycle Sequencing on an ABI 373A Sequencing System. The nucleotide and corresponding amino acid sequences of the said Fab clones form the basis of this invention.

Sequence analysis has revealed that several clones were isolated bearing the same $V_H$ gene segment but different $V_L$ gene segments. This is the case for the two clones LD2-1 and LD2-10, for the two clones LD2-4 and LD2-11, and for the three clones LD2-14, LD1/2-6-3 and LD1/2-6-33, respectively.

The DNA sequences obtained and Fab fragments are useful for the preparation of complete antibodies having an activity against the Rhesus D antigen. Suitable expression systems for such antibodies are mouse myeloma cells or chinese hamster ovary cells.

The examples which follow explain the invention in detail, without any restriction of the scope of the invention.

Example 1 describes the construction of 2 combinatorial librairies; especially the aforementioned LD1 and LD2 libraries.

Example 2 describes a series of pannings using R1R1 rbc on the said LD1 and LD2 libraries in detail.

Example 3 describes a series of pannings using both bromelase and non bromelase treated rbc for absorption and bromelase treated DVI positive rbc using a pool of the said LD1 and LD2 libraries.

Example 4 describes an indirect haemagglutination assay using a rabbit anti-phage antibody, as an equivalent Coombs reagent, to monitor the enrichment and specificity of Rhesus D specific Phabs after panning.

Example 5 describes the preparation and purification of Fab antibody fragments for application as diagnostic reagents.

Example 6 describes the preparation of complete anti-Rhesus D immunoglobulins using the sequences of the present invention.

EXAMPLE 1

Construction of the Recombinant LD1 and LD2 Libraries a) Source of the Lymphocytes A male adult who was a member of the volunteer pool of hyperimmune Rhesus D donors was given an i.v. boost of 2 ml of packed rbc from a known male donor of blood group O RhD+. The PBL were harvested at +5 and +18 days after the boost and the mononuclear cells (MNC) isolated by Ficoll gradient centrifugation (Lymphoprep, Pharmacia, Milwaukee, Wis.). The results of donor lymphocyte analysis of day +5 are given in table 4. The +5 day MNC were used directly for RNA preparation using a phenol-chloroform guanidinium isothiocyanate procedure (Chomczynski, P. and Sacchi, N., Anal. Biochem. 162:156, 1987). The +18 day MNC were first cultured for 3 days in RPMI-1640 medium (Seromed, Basel) containing $10^3$ U/ml of IL-2 (Sandoz Research Center, Vienna, Austria) and 10 µg/ml of pokeweed mitogen (PWM; Sigma L9379, Buchs, Switzerland) before extracting RNA.

TABLE 4

Immunofluorescence analysis of donor lymphocytes +5 days after rbc i.v. boost

| Cell surface antigen | % Positive cells | Cell surface antigen | % Positive cells |
|---|---|---|---|
| CD20 | 15 | CD8 | 12 |
| CD38 | 20 | CD25 | 7.6 |
| CD20/38 | 15 | CD57 | 12.5 |

TABLE 4-continued

Immunofluorescence analysis of donor lymphocytes +5 days after rbc i.v. boost

| Cell surface antigen | % Positive cells | Cell surface antigen | % Positive cells |
|---|---|---|---|
| CD3 | 47 | CD14 | 6 |
| CD4 | 34 | HLA-DR | 18 | b) Construction of Library

Two separate libraries were constructed called LD1 and LD2 (as detailed above) corresponding to the cells harvested at +5 days and +18 days (finally +21 days including the +3 days PWM stimulation) after the i.v. boost respectively. Total RNA was then prepared from these cells using a phenol-chloroform guanidinium isothiocyanate method. From this RNA, 10 µg were used to make cDNA using an oligo(dt) primer (400 ng) and reverse transcribed with M-MuLV reverse transcriptase according to the conditions specified by the supplier (Boehringer Mannheim Germany). PCR amplification was performed as described in Vogel, M. et al., E. J. of Immunol. 24:1200, 1994. Briefly, 100 µl PCR reaction contained Perkin-Elmer buffer with 10 mM $MgCl_2$, 5 µl cDNA, 150 ng of each appropriate 5' and 31 primer, all four dNTP at 200 µM each and 2 U/ml Taq Polymerase (Perkin Elmer, NJ). The PCR amplification of the heavy and light chains of the Fab molecule was performed separately with a set of primers from Stratacyte (details given below). For the heavy chain six upstream primers were used that hybridize to each of the six families of the $V_H$ genes whereas one kappa and one lambda chain primer were used for the light chain. The downstream primers were designed to match the hinge region of the constant domains γ1 and γ3 for the heavy chain. For the light chain the downstream primers were matched to the 3', end of kappa and lambda constant domains. The heavy and light chain PCR products were pooled separately, gel purified and cut with Xho1/Spe1 and Sac1/Xba1 restriction enzymes (Boehringer Mannheim), respectively. After digestion the PCR products were extracted once with phenol:chloroform:isoamylalcohol and purified by gel excision. The insertion of the Xho1/Spe1 digested Fd fragment and subsequent ligation of the Sac1/Xba1 digested light chain into the pComb3 vector, the transformation into XL1-Blue cells, and the production of phages were performed as described by (Barbas III, C. F. and Lerner, R. A., Companion Methods Enzymol. 2:119, 1991).

After transformation of the XL1-Blue *E. coli* cells samples were withdrawn and titrated on plates to determine the library size. These results indicated expression libraries of $7.5 \times 10^6$ and $7.7 \times 10^6$ cfu (colony forming units) for LD1 and LD2 respectively.

c) PCR Primers

```
VHI     5'-CAC TCC CAG GTG CAG CTG CTC GAG TCT GG-3'     (SEQ ID NO. 65)

VHII    5'-GTG CTG TCC CAG GTC AAC TTA CTC GAG TCT GG-3'  (SEQ ID NO. 66)

VHIII   5'-GTC CAG GTG GAG GTG CAG CTG CTC GAG TCT GG-3'  (SEQ ID NO. 67)

VHIV    5'-GTC CTG TCC CAG GTG CAG CTG CTC GAG TCG GG-3'  (SEQ ID NO. 68)

VHV     5'-GTC TGT GCC GAG GTG CAG CTG CTC GAG TCT GG-3'  (SEQ ID NO. 69)

VHVI    5'-GTC CTG TCA CAG GTA CAG CTG CTC GAG TCA GG-3'  (SEQ ID NO. 70)
```

-continued c) PCR Primers

| | | |
|---|---|---|
| CHI(g1) | 5'-AGC ATC ACT AGT ACA AGA TTT GGG CTC-3' | (SEQ ID NO. 71) |
| VL(k) | 5'-GT GCG AGA TGT GAG CTC GTG ATG ACC CAG TCT CCA-3' | (SEQ ID NO. 72) |
| CL(k) | 5'-T CCT TCT AGA TTA CTA ACA CTC TCC CCT GTT GAA GCT CTT TGT GAC GGG CGA ACT C-3' | (SEQ ID NO. 73) |
| VL(l) | 5'C TGC ACA GGG TCC TGG GCC GAG CTC GTG GTG ACT CA-3' | (SEQ ID NO. 74) |
| CL(l) | 5'G CAT TCT AGA CTA TTA TGA ACA TTC TGT AGG GGC-3' | (SEQ ID NO. 75) | d) Vectors and Bacterial Strains

The pComb3 vector used for cloning of the Fd and the light chain was obtained from the Scripps Research Institute La Jolla, Calif.; (Barbas III, C. F. and Lerner, R. A., Companion Methods Enzymol. 2:119, 1991). The *Escherichia coli* strain XL1-Blue used for transformation of the pComb3 vector and the VCSM13 helper phage were purchased from Stratacyte (La Jolla, CA).

EXAMPLE 2

Selection of Rhesus D Phabs from LD1 and LD2 Libraries on R1R1 rbc a) Absorption and Bio-Panning A series of three negative absorptions on rbc group O Rh negative were performed for each panning round before positive selection on rbc group O Rh positive (R1R1). Fresh rbc were collected in ACD (acid citrate dextrose) anticoagulant and washed 3 times in 0.9% NaCl. The rbc were counted in Hayems solution and adjusted to $40 \times 10^6$/ml. Absorption: 1 ml of phage preparation in PBS/3% BSA was added to rbc group O Rh negative pellet ($16 \times 10^6$ rbc) in 12 ml tubes (Greiner 187261, Reinach, Switzerland) and incubated at RT for 30 min. with careful shaking. All tubes were pre-blocked in PBS/3% BSA for a minimum of 1 hr at RT. The rbc were pelleted by centrifuging for 5 min. 300×g at 4° C. The resulting phage supernatant was carefully harvested and the process repeated twice more. After the final absorption the phage supernatant was added to the rbc group O Rh positive pellet ($16 \times 10^6$ rbc) and again incubated at RT for 30 min. with gentle shaking. Then the rbc were washed at least 5 times in 10 ml ice cold PBS, centrifuged 5 min. 300×g at 4° C., followed by elution with 200 µl of 76 mM citric acid pH 2.8 for 6 min. at R.T. and neutralisation with 200 µl 1M Tris. The rbc were centrifuged 300×g, 5 min. at 4° C. and the resulting supernatant containing the eluted phages was carefully removed and stored with carrier protein (0.3% BSA) at 4° C. ready for re-amplification. The numbers of Rhesus D specific Phabs of each panning round are given in table 5.

TABLE 5

Selection of Rhesus D+ Phabs from the LDI and LD2 libraries on R1R1 rbc

| | No. of eluted Rhesus D specific phages | |
|---|---|---|
| Panning Round No.[a] | Library D1 cfu | Library D2 cfu |
| 1 | $8 \times 10^6$ | $4.6 \times 10^7$ |
| 2 | $6 \times 10^7$ | $1.4 \times 10^7$ |

TABLE 5-continued

Selection of Rhesus D+ Phabs from the LDI and LD2 libraries on R1R1 rbc

| | No. of eluted Rhesus D specific phages | |
|---|---|---|
| Panning Round No.[a] | Library D1 cfu | Library D2 cfu |
| 3 | $1 \times 10^8$ | $7.9 \times 10^7$ |
| 4 | $3 \times 10^8$ | $1.3 \times 10^8$ |
| 5 | $3 \times 10^8$ | $1 \times 10^8$ |
| 6 | nd | $2.8 \times 10^8$ |

[a] For each round $10^{12}$ Phabs were incubated in tubes with rbc Group O Rhesus negative (absorption phase) followed by elution from rbc Group O Rhesus positive (R1R1)
nd = not done
cfu = colony forming units

EXAMPLE 3

Selection of Rhesus D Phabs from the Pooled LD1 and LD2 Libraries on DVI+ rbc a) Absorption on rbc Group O Rh Negative, Phenotypes 1 (r'r, Ccddee) and 2 (ryry, CCddEE)

A series of four negative absorptions on rbc group O Rh negative was performed for each panning round before positive selection on rbc group O Rh DV1 positive. The negative absorptions were performed in the following order: Step 1) phenotype 1 treated with bromelase; step 2) phenotype 1 no bromelase; step 3) phenotype 2 treated with bromelase; step 4) phenotype 2 no bromelase. Frozen rbc were thawed into a mixture of sorbit and phosphate buffered saline, left standing in this solution for a minimum of 10 min. and then washed 5 to 6 times in phosphate buffered saline and finally stored in stabilising solution (DiaMed EC-Solution) ready for use. Before panning the rbc were washed 3 times in 0.9% NaCl. followed by counting in Hayems solution. Absorption: 1 ml of phage preparation in PBS/3% BSA was added to an rbc pellet ($2 \times 10^8$) as in step 1 in 12 ml tubes (Greiner 187261, Reinach, Switzerland) and incubated at RT for 30 min. with careful shaking. All tubes were pre-blocked in PBS/3% BSA for a minimum of 1 hr at RT. The rbc were pelleted by centrifuging for 5 min. 300×g at 4° C. The resulting phage supernatant was carefully harvested and the process repeated using rbc as detailed above in steps 2, 3, and 4.

b) Treatment of rbc Rhesus D Negative r'r and ryry and Rhesus DVI+ with Bromelase Bromelase 30 (Baxter, Düdingen, Switzerland) was used to treat rbc Rhesus DVI+ in the same proportions as used in a routine haemagglutination assay, i.e. 10 µl bromelase per $2 \times 10^6$ rbc. Thus bromelase was added to the required amount of rbc and incubated at 37° C. for 30 min. followed by washing 3 times in 0.9% NaCl, re-counting in Hayems solution and adjusting to the required concentration in PBS/3% BSA ready for Phab panning.

c) Bio-Panning on Bromelase Treated Rhesus DVI+ rbc

After the final absorption on rbc ryry non bromelase treated the phage supernatant was divided into 2 equal parts and added either to the enzyme or non enzyme treated rbc group O Rh DVI+ pellet ($40 \times 10^6$) respectively and again incubated at RT for 30 min. with gentle shaking. Then the 2 populations of rbc were washed at least 5 times in 10 ml ice cold PBS, centrifuged 5 min. 300×g at 4° C., followed by elution with 200 µl of 76 mM citric acid pH 2.8 for 6 min. at R.T. and neutralisation with 200 µl 1M Tris. The rbc were centrifuged 300×g, 5 min. at 4° C. and the resulting supernatants containing the eluted phages from either the bromelase or non bromelase treated DVI+rbc were carefully removed and stored with carrier protein (0.3% BSA) at 4° C. ready for re-amplification. In further rounds of panning the eluted phage from either the bromelase or non bromelase treated DVI+ rbc were kept separate and each followed the absorption protocol steps 1 to 4. The elution step was slightly different compared to panning round 1 as the phage populations were not again divided into 2 parts. Only those phage eluted from bromelase treated DVI+ rbc were also eluted again from bromelase treated DVI+ rbc and only those phage eluted from the non bromelase treated DVI+ rbc were also again eluted from non bromelase treated DVI+ rbc. The numbers of specific Phabs after each panning round are given in table 6.

TABLE 6

Selection of Rhesus D Phabs from pooled LD1 and LD2 libraries on Rhesus DVI+ red blood cells

| | No. of eluted Rhesus DVI+ specific phages | |
|---|---|---|
| Panning Round No.[a] | − Bromelase cfu | + Bromelase cfu |
| 1 | $1.9 \times 10^6$ | $4.4 \times 10^6$ |
| 2 | $1.6 \times 10^6$ | $4 \times 10^5$ |
| 3 | $2.4 \times 10^7$ | $4.1 \times 10^7$ |
| 4 | $3 \times 10^6$ | $5 \times 10^7$ |
| 5 | $1 \times 10^{78}$ | $1 \times 10^8$ |
| 6 | nd | $3 \times 10^8$ |

[a]For each round $10^{12}$ Phabs were incubated in tubes with 2 different phenotypes of rbc Group O Rhesus negative (absorption phase) followed by elution from rbc Group O Rhesus DVI+.

EXAMPLE 4

Monitoring of the Panning Rounds and Determination of the Specificity of the Enriched Phabs Using a Rabbit Anti-Phage Antibody Indirect Haemagglutination Assay Freshly collected rbc of different ABO and Rhesus blood groups were washed 3 times in 0.9% NaCl and adjusted to a 3–5% solution ($45-50 \times 10^7$/ml) in either 0.9% NaCl or PBS/3% BSA. For each test condition 50 µl rbc and 100 µl test (precipitated and amplified phage or control antibodies) were incubated together in glass blood grouping tubes (Baxter, Düdingen, Switzerland) for 30 min. at 37° C. The rbc were washed 3 times in 0.9% NaCl and then incubated with 2 drops of Coombs reagent (Baxter, Düdingen, Switzerland) for positive controls or with 100 µl of 1/1000 diluted rabbit anti-phage antibodies (made by immunising rabbits with phage VCSM13 preparation, followed by purification on an Affi-Gel Blue column and absorption on *E. coli* to remove *E. coli*-specific antibodies). The tubes were incubated for 20 min at 37° C., centrifuged 1 min at 125×g and rbc examined for agglutination by careful shaking and using a magnifier viewer.

When purified Fab were tested for agglutination, an affinity purified anti-Fab antibody (The Binding Site, Birmingham, U.K.) was used instead of the rabbit anti-phage antibody.

Table 7 shows the results of haemagglutination tests of Phab samples after different panning rounds on R1R1 rbc.

Table 8 shows the results of haemagglutination tests of Phab samples after different panning rounds on Rhesus DVI+ rbc.

Table 9 shows the reactivity pattern of individual Fab clones from libraries LD1 and LD2 with partial D variants.

TABLE 7

Monitoring of Phabs from LD1 and LD2 libraries by indirect haemagglutination after panning on R1R1 rbc

| Phab sample Panning round | Library LD1 | Library LD2 |
|---|---|---|
| | tested on rbc O Rh D+[a] | |
| No. 4 | | |
| undiluted | + | + |
| 1/4 | + | +/− |
| 1/20 | − | − |
| No. 5 | | |
| undiluted | ++ | + |
| 1/4 | ++ | + |
| 1/20 | − | − |
| No. 6 | | |
| undiluted | nd | +++ |
| 1/4 | nd | ++ |
| 1/20 | nd | nd |
| Helper phage[b] | | |
| undiluted, 1/4, 1/20 | − | − |

[a]Indirect haemagglutination was performed in glass tubes using 50 µl rbc ($40 \times 10^7$/ml) and 100 µl Phabs starting at $4 \times 10^{11}$/ml. After 30 min. at 37° C. the rbc were washed 3 times and further incubated for 20 min. at 37° C. with a 1/1000 dilution of rabbit anti-phage antibody.
[b]The M13 helper phage was used as a negative control and showed no non-specific agglutination due to the phage particle alone.
Agglutination was scored by visual assessment from +++ (strong agglutination) descending to − (no agglutination).
nd = not done

TABLE 8

Monitoring of Phabs from pooled LD1 and LD2 libraries by indirect haemagglutination after panning on Rhesus DVI+ rbc

| Phab sample | rbc phenotypes | | | | | |
|---|---|---|---|---|---|---|
| Panning round | CCDDee | ccddee | Ccddee | CCddEE | DVI (E.J.) | DVI (K.S.) |
| Non Bromelase treated rbc DVI+ | | | | | | |
| Round No. 3 | [a)]+++ | – | +/– | (+) | +/– | +/– |
| Round No. 5 | ++ | – | – | – | – | – |
| Bromelase treated rbc DVI+ | | | | | | |
| Round No. 4 | +++ | – | +/– | – | (+) | +/– |
| Round No. 5 | +++ | – | +/– | +/– | (+++) | ++ |
| Round No. 6 | ++++ | – | – | – | +++ | +++ |
| LD1-6-17 | | | reactive with C and E | | | |
| LD1/2-6-3 | ++++ | – | – | – | +/– | nd |
| LD1/2-6-33 | ++++ | – | – | – | + | nd |

[a)]Agglutination was scored by visual assessment from ++++ (strong agglutination) descending to – (no agglutination).
nd = not done
Note: Only those Phabs eluted from bromelase treated DVI+ rbc showed evidence of agglutination against 2 different DVI+ donors.

TABLE 9

Clonal Analysis of Reactivity of Fab anti-Rhesus D Clones from Libraries D1 and LD2 against Partial D Variants

| | | Partial D Variants | | | | | |
|---|---|---|---|---|---|---|---|
| [(a)]Fab Clone No | Rh33 | DIII | DIVa | DIVb | DVa | DVI | DVII |
| LD1 - 40 | – | [(b)]+++ | + | + | +/– | – | ++ |
| - 52 | – | +++ | – | – | +++ | – | +++ |
| - 84 | – | ++ | – | – | – | – | + |
| - 110 | (+) | +++ | ++ | + | + | – | ++ |
| - 117 | – | +++ | – | – | – | – | ++ |
| LD2 - 1 | +++ | nd | +++ | +++ | + | – | +++ |
| - 4 | – | +++ | – | + | – | – | + |
| - 5 | – | nd | +++ | +++ | – | – | +++ |
| - 10 | (–) | +++ | +++ | +++ | + | – | ++ |
| - 11 | – | +++ | – | – | – | – | ++ |
| - 14 | +++ | +++ | +++ | +++ | +++ | – | +++ |
| - 17 | – | +++ | +++ | + | +/– | – | +++ |
| - 20 | – | +++ | +++ | – | +/– | – | +++ |
| LD1/2 - 6-3 | ++ | +++ | +++ | ++ | +++ | + | ++ |
| LD1/2 - 6-33 | +/– | +++ | +++ | ++ | +++ | + | ++ |

[(a)]soluble Fab preparations were made of each clone followed by indirect haemagglutination.
[(b)]Agglutination was scored by visual assessment from +++ (all cells agglutinated in a clump) descending to – (no cells agglutinated).

EXAMPLE 5

Preparation and Purification of Fab Antibody Fragments for Application as Diagnostic Reagents After the bio-panning procedures detailed in Examples 2 and 3 a phage population which showed specific agglutination on Rhesus D+ rbc was selected and used to prepare phagemid DNA. More precisely the Phabs selected on R1R1 rbc were used after the 5th and 6th rounds of bio-panning for LD1 and LD2 libraries respectively and after the 5th bio-panning on DVI+ rbc for isolation of the LD1-6-17 clone. In order to produce soluble Fab, the 10 sequence gIII coding for the pIII tail protein of the phage particle must be deleted. Phagemid DNA was prepared using a Nucleotrap kit (Machery-Nagel) and the gIII sequence was removed by digesting the so isolated phagemid DNA with Nhe1/Spe1 as described (Burton, D. R., et al., PNAS, 1989). After transformation into XL1-Blue individual clones were selected (nomenclature given in table 1) and grown in LB (Luria Broth) containing 50 µg/ml carbenicillin at 370° C. to an OD of 0.6 at 600 nm. Cultures were induced with 2 mM isopropyl β-D-thiogalactopyranoside (IPTG) (Biofinex, Praroman, Switzerland) and grown overnight at 37° C. The whole culture was spun at 10,000×g for 30 min. at 4° C. to pellet the bacteria. The bacterial pellet was treated with a lysozyme/DNase solution to liberate the Fab fragments inside the cells. As some Fab were released into the culture supernatant this was also harvested separately. These Fab preparations were then pooled and precipitated with 60% ammonium sulphate (Merck, Darmstadt, Germany) to concentrate the Fab followed by extensive dialysis in phosphate buffered saline (PBS) and ultracentrifugation at 200,000×g to pellet any insoluble complexes. The Fab preparations were then purified on a ceramic hydroxyapatite column (HTP Econo cartridge, BioRad, Glattbrugg, Switzerland) using a gradient elution of PBS (Buffer A) and PBS+0.5M NaCl (Buffer B). The linear gradient was programmed to increase from 0–100% Buffer B in 40 min. The Fab was eluted as a single peak between 40–60% Buffer B. The positive fractions as identified by immunodot assay using an anti-Fab peroxidase conjugate (The Binding Site, Birmingham, U.K.) were pooled, concentrated using polyethylene glycol and extensively dialysed against PBS. The positive fractions from the hydroxyapatite column for each clone were used in a classical indirect haemagglutination assay in glass tubes using either the standard Coombs reagent (Baxter Diagnostics AG Dade, anti-human serum) or an anti-Fab (The Binding Site, Birmingham, U.K.) as the cross linking reagent. These Fab of defined specificity on the Partial D variants as shown on page 18 can be used to type rbc of unknown Partial D phenotype.

EXAMPLE 6

Construction of Complete Immunoglobulin Genes

The LD2-14 heavy chain V gene ($V_H$ gene) was amplified from the anti-Rhesus D-Fab-encoding plasmid LD2-14 with the polymerase chain reaction (PCR) using specific primers. The 5'-primer had the sequence: SEQ ID NO 78 5'-GGGTC-GACGCACAGGTGAAACTGCTCGAGTCTGG-3', whereas the 3'-primer was of the sequence: SEQ ID NO 79 5'-GCCGATGTGTAAGGTGACCGTGGTCCCCTTG-3'.

The PCR reaction was performed with Deep Vent DNA Polymerase and the buffer solution (2 mM $Mg^{++}$) from New England Biolabs at the conditions recommended by the manufacturer including 100 pmol of each primer and the four deoxynucleotides at a concentration of 250 μM each. The reaction was run for 30 cycles with the following temperature steps: 60 s at 94° C. (extended by 2 min. during the first cycle), 60 s at 57° C. and 60 s at 72° C. (extended by 10 min. during the last cycle). Post-amplification addition of 3' A-overhangs was accomplished by a subsequent incubation for 10 min at 72° C. in the presence of 1 unit Taq DNA Polymerase (Boehringer Mannheim, Germany). The PCR product was purified using the QIAquick PCR purification kit (Qiagen, Switzerland) and cloned into the vector pCRII using Invitrogen's TA cloning kit (San Diego, USA). Having digested the resulting plasmid TAVH14 with SalI and BstEII, the $V_H$ gene was isolated by preparative agarose gel electrophoresis using Qiagen's QIAquick gel extraction kit.

Vector # 150 (Sandoz Pharma, Basel) which contained an irrelevant but intact human genomic immunoglobulin $V_H$ gene was cut with SalI and BstEII, and the vector fragment was isolated by preparative agarose gel electrophoresis using Qiagen's QIAquick gel extraction kit. Ligation of vector and PCR product was performed at 25° C. for 2 hours in a total volume of 20 μl using the rapid DNA Ligation kit (Boehringer Mannheim, Germany). Following ligation, the reaction mix was diluted with 20 μl $H_2O$ and extracted with 10 volumes of n-butanol to remove salts. The DNA was then pelleted by centrifugation, vacuum dried and resuspended in 10 μl $H_2O$. 5 μl of this DNA solution were electroporated (0.1 cm cuvettes, 1.9 kV, 200 Ω, 25 μFD) with a GenePulser (BioRad, Gaithersburg) into 40 μl of electroporation competent E. coli XL1-blue MRF' (Stratagene, La Jolla), diluted with SOC medium, incubated at 37° C. for 1 hour and plated on LB plates containing ampicillin (50 μg/ml). Plasmid-minipreps (Qiagen, Basel) of the resulting colonies were checked with restriction digests for the presence of the appropriate insert.

With this procedure, the irrelevant resident $V_H$ gene in vector #150 was replaced by the amplified anti-Rhesus D $V_H$ sequence of LD2-14 and yielded plasmid cassVH14. The structure of the resulting immunoglobulin $V_H$ gene construct was confirmed by sequencing, cut out by digestion with EcoRI and BamHI and gel purified as described above. Expression vector # 10 (Sandoz Pharma, Basel) containing the human genomic immunoglobulin Cγ1 gene segment was also digested with EcoRI and BamHI, isolated by preparative agarose gel electrophoresis, ligated with the EcoRI/BamHI-$V_H$ gene segment previously obtained from plasmid cassVH14 and electroporated into E. coli XL1-blue MRF' as outlined above. This resulted in a complete anti-Rhesus D heavy chain immunoglobulin gene in the expression vector 14IgG1 (Figure and).

The LD2-14 light chain V gene ($V_L$ gene) was amplified from the same anti-Rhesus D-Fab plasmid LD2-14 by PCR using specific primers. The 5'-primer had the sequence: 5'-TACGCGTTGTGACATCGTGATGAC-CCAGTCTCCAT-3' SEQ. ID. NO. 76 whereas the 3'-primer was of the sequence: 5'-AGTCGCT-CAGTTCGTTTGATTTCAAGCTTGGTCC-3' SEQ. ID. NO. 77.

PCR reaction, product purification and subsequent cloning steps were analogous to the steps described for the $V_H$ gene, except that the appropriate light chain vectors were used. Briefly, the $V_L$ PCR product was cloned into pCRII vector yielding plasmid TAVL14, excised therefrom with MluI and HindIII and isolated by gel extraction. The $V_L$ gene was subsequently cloned into the MluI and HindIII sites of vector # 151 (Sandoz Pharma, Basel) thus replacing the irrelevant resident $V_L$ gene by the amplified anti-Rhesus D $V_L$ sequence of LD2-14. Having confirmed the sequence of the resulting plasmid cassVL-14, the EcoRI/XbaI fragment containing the $V_L$ gene was then subcloned into the restriction sites EcoRI and XbaI of vector# 98 (Sandoz Pharma, Basel, Switzerland) which contains the human genomic immunoglobulin Cκ gene segment. This procedure replaced the irrelevant resident $V_L$ gene in plasmid # 98 and yielded the expression vector 14kappa which contains the complete anti-Rhesus D light chain immunoglobulin gene.

The mouse myeloma cell line SP2/0-Ag 14 (ATCC CRL 1581) was cotransfected by electroporation with the expression vectors 14IgG1 and 14kappa previously linearized at the unique EcoRI and NotI cleavage site, respectively. The electroporation was performed as follows: exponentially growing cells were washed twice and suspended in phosphate buffered sucrose (272 mM sucrose, 1 mM $MgCl_2$, 7 mM $NaH_2PO_4$, pH 7.4) at a density of $2 \times 10^7$ cells/ml. 0.8 ml of cells were added to a 0.4 cm cuvette, mixed with 15 μg of linearized plasmids 14IgG1 and 14kappa, held on ice for 15 min., electroporated with 290 Volts, 200 Ω, 25 μFD, put back on ice for 15 min., transferred to a T75 cell culture flask with 20 ml of cold RPMI 1640 medium (10% heat inactivated fetal bovine serum, 50 μM beta-mercaptoethanol), left for 2 h at room temperature and then incubated for 60 h at 37° C. After this period, the cells were transferred to 50 ml of medium containing 1 mg/ml G418 for selection. Stable transfectants were then selected in the presence of increasing concentrations of methotrexate to amplify the integrated DNA and thus increasing the expression of the corresponding antibody rD2-14.

Expression of rD2-14 in the culture's supernatant (SrD2-14) was monitored by an enzyme linked immuno-sorbent assay (ELISA) specific for human γ1 and kappa chains. Quantification of the Rhesus D specific immunoglobulins in the anti-D assay according to Ph. Eur. revealed between 1.1 and 11.4 μg/ml of agglutinating antibody in such supernatants. They tested agglutination negative for Rhesus negative rbc and revealed the same agglutination potential against partial D variants as the Fab LD2-14 expressed in E. coli. The data are shown in table 10.

TABLE 10

Comparative analysis of reactivity of Fab anti-Rhesus D clone LD2-14 and antibody rD2-14 against partial D variants

| | Partial D Variants | | | | | | | |
|---|---|---|---|---|---|---|---|---|
| | R1R1 | rr | Rh33 | DIII | DIVa | DIVb | DVa | DVI | DVII |
| LD2-14 | +++ | − | +++ | +++ | +++ | +++ | +++ | − | +++ |
| SrD2-14 | +++ | − | +++ | +++ | +++ | +++ | +++ | − | +++ |
| TCB | − | − | | | | | | | |

Agglutination was scored by visual assessment from +++ (all cells agglutinated in a clump) descending to − (no cells agglutinated).
LD2-14: Fab fragment prepared as described in Example 5;
SrD2-14: cell culture supernatant containing antibody rD2-14;
TCB: cell culture supernatant of untransfected cells.

---

The invention claimed is:

1. A purified polypeptide capable of forming antigen binding structures with specificity for Rhesus D antigens comprising
   (a) $V_H$ region having SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 30, SEQ ID NO: 34, SEQ ID NO: 38, SEQ ID NO: 42, SEQ ID NO: 46, SEQ ID NO: 50, SEQ ID NO: 54, SEQ ID NO: 58 or SEQ ID NO: 62, and
   (b) a $V_L$, region having SEQ ID NO: 4, SEQ ID NO: 8, SEQ ID NO: 12, SEQ ID NO: 16, SEQ ID NO: 20, SEQ ID NO: 24, SEQ ID NO: 28, SEQ ID NO: 32, SEQ ID NO: 36, SEQ ID NO: 40, SEQ ID NO: 44, SEQ ID NO: 48, SEQ ID NO: 52, SEQ ID NO: 56, SEQ ID NO: 60, or SEQ ID NO: 64.

2. The polypeptide of claim 1, wherein the $V_L$ region has SEQ ID NO: 60.

3. The polypeptide of claim 1, wherein the polypeptide is an antigen binding Fab fragment.

4. The polypeptide of claim 1, wherein the polypeptide is an immunoglobulin specific for a Rhesus D antigen.

5. The polypeptide of claim 4, wherein the immunoglobulin comprises at least one defined isotype selected from the group consisting of IgG1, IgG2, IgG3, and IgG4.

6. A composition comprising at least one polypeptide of claim 4 and a pharmaceutically acceptable carrier.

7. A diagnostic composition for Rhesus D typing comprising at least one polypeptide of claim 4.

8. A recombinant polynucleotide which encodes the polypeptide of claim 1.

9. A pharmaceutical composition comprising at least one polypeptide of claim 1 and a pharmaceutically acceptable carrier.

10. A diagnostic composition for Rhesus D typing comprising at least one polypeptide of claim 1.

11. The polypeptide of claim 1, wherein the $V_H$ region has SEQ ID NO: 58.

12. The polypeptide of claim 1, wherein the $V_H$ region has SEQ ID NO: 58 and the $V_L$ region has SEQ ID NO: 60.

* * * * *

UNITED STATES PATENT AND TRADEMARK OFFICE
CERTIFICATE OF CORRECTION

| | |
|---|---|
| PATENT NO. | : 7,038,020 B1 |
| APPLICATION NO. | : 09/147443 |
| DATED | : May 2, 2006 |
| INVENTOR(S) | : Andreas Morell et al. |

It is certified that error appears in the above-identified patent and that said Letters Patent is hereby corrected as shown below:

IN THE SPECIFICATION:

Col. 3, line 48, please insert --as follows-- after "disclosed"

Col. 3, after line 48, please insert the following paragraphs

--FIG. 1a is an LD1-40-VH sequence (SEQ ID NOS 1-2);--

--FIG. 1b is an LD1-40-VL sequence (SEQ ID NOS 3-4);--

--FIG. 2a is an LD1-52-VH sequence (SEQ ID NOS 5-6);--

--FIG. 2b is an LD1-52-VL sequence (SEQ ID NOS 7-8);--

--FIG. 3a is an LD1-84-VH sequence (SEQ ID NOS 9-10);--

--FIG. 3b is an LD1-84-VL sequence (SEQ ID NOS 11-12);--

--FIG. 4a is an LD1-110-VH sequence (SEQ ID NOS 13-14);--

--FIG. 4b is an LD1-110-VL sequence (SEQ ID NOS 15-16);--

--FIG. 5a is an LD1-117-VH sequence (SEQ ID NOS 17-18);--

--FIG. 5b is an LD1-117-VL sequence (SEQ ID NOS 19-20);--

--FIG. 6a is an LD2-1-VH sequence (SEQ ID NOS 21-22);--

--FIG. 6b is an LD2-1-VL sequence (SEQ ID NOS 23-24);--

--FIG. 7a is an LD2-4-VH sequence (SEQ ID NOS 25-26);--

--FIG. 7b is an LD2-4-VL sequence (SEQ ID NOS 27-28);--

--FIG. 8a is an LD2-5-VH sequence (SEQ ID NOS 29-30);--

--FIG. 8b is an LD2-5-VL sequence (SEQ ID NOS 31-32);--

UNITED STATES PATENT AND TRADEMARK OFFICE
CERTIFICATE OF CORRECTION

| | | |
|---|---|---|
| PATENT NO. | : 7,038,020 B1 | Page 2 of 8 |
| APPLICATION NO. | : 09/147443 | |
| DATED | : May 2, 2006 | |
| INVENTOR(S) | : Andreas Morell et al. | |

It is certified that error appears in the above-identified patent and that said Letters Patent is hereby corrected as shown below:

--FIG. 9a is an LD2-10-VH sequence (SEQ ID NOS 33-34);--

--FIG. 9b is an LD2-10-VL sequence (SEQ ID NOS 35-36);--

--FIG. 10a is an LD2-11-VH sequence (SEQ ID NOS 37-38);--

--FIG. 10b is an LD2-11-VL sequence (SEQ ID NOS 39-40);--

--FIG. 11a is an LD2-14-VH sequence (SEQ ID NOS 41-42);--

--FIG. 11b is an LD2-14-VL sequence (SEQ ID NOS 43-44);--

--FIG. 12a is an LD2-17-VH sequence (SEQ ID NOS 45-46);--

--FIG. 12b is an LD2-17-VL sequence (SEQ ID NOS 47-48);--

--FIG. 13a is an LD2-20-VH sequence (SEQ ID NOS 49-50);--

--FIG. 13b is an LD2-20-VL sequence (SEQ ID NOS 51-52);--

--FIG. 14a is an LD1-6-17-VH sequence (SEQ ID NOS 53-54);--

--FIG. 14b is an LD1-6-17-VL sequence (SEQ ID NOS 55-56);--

--FIG. 15a is an LD1/2-6-3-VH sequence (SEQ ID NOS 57-58);--

--FIG. 15b is an LD1/2-6-3-VL sequence (SEQ ID NOS 59-60);--

--FIG. 16a is an LD1/2-6-33-VH sequence (SEQ ID NOS 61-62); and --

--FIG. 16b is an LD1/2-6-33-VL sequence (SEQ ID NOS 63-64).--

Col. 3, line 49, delete "the" and insert --a--

Col. 3, lines 49-50, delete "used according to the present invention"

Col. 3, line 56, insert --following-- after "the", insert --:-- after "definition" and delete "of claim 1"

UNITED STATES PATENT AND TRADEMARK OFFICE
CERTIFICATE OF CORRECTION

PATENT NO.        : 7,038,020 B1  
APPLICATION NO.   : 09/147443  
DATED             : May 2, 2006  
INVENTOR(S)       : Andreas Morell et al.

Page 3 of 8

It is certified that error appears in the above-identified patent and that said Letters Patent is hereby corrected as shown below:

Col. 3, after line 56, insert the following paragraph:

--Polypeptides capable of forming antigen binding structures with specificity for Rhesus D antigens which include Rhesus D-specific CDR 1, CDR 2 and CDR 3 regions of pairs of amino acid sequences $V_H$ and $V_L$ with the same or different identification numbers according to the figures given in the table below:

| Identi-fication No. | $V_H$ | | | | $V_L$ | | | |
|---|---|---|---|---|---|---|---|---|
| | Figure | CDR 1 base pair No. | CDR 2 base pair No. | CDR 3 base pair No. | Figure | CDR 1 base pair No. | CDR 2 base pair No. | CDR 3 base pair No. |
| LD1-40 | Fig. 1a | 91-105 | 148-198 | 295-342 | Fig. 1b | 64-96 | 142-162 | 259-288 |
| LD1-52 | Fig. 2a | 91-105 | 148-198 | 295-342 | Fig. 2b | 64-96 | 142-162 | 259-288 |
| LD1-84 | Fig. 3a | 91-105 | 148-198 | 295-342 | Fig. 3b | 64-96 | 142-162 | 259-285 |
| LD1-110 | Fig. 4a | 91-105 | 148-198 | 295-342 | Fig. 4b | 64-96 | 142-162 | 259-285 |
| LD1-117 | Fig. 5a | 91-105 | 148-198 | 295-345 | Fig. 5b | 64-96 | 142-162 | 259-288 |
| LD2-1 | Fig. 6a | 91-105 | 148-198 | 295-342 | Fig. 6b | 61-99 | 145-165 | 262-294 |
| LD2-4 | Fig. 7a | 91-105 | 148-198 | 295-342 | Fig. 7b | 64-96 | 142-162 | 259-282 |
| LD2-5 | Fig. 8a | 91-105 | 148-198 | 295-342 | Fig. 8b | 64-96 | 142-162 | 259-288 |
| LD2-10 | Fig. 9a | 91-105 | 148-198 | 298-345 | Fig. 9b | 61-102 | 148-168 | 265-294 |
| LD2-11 | Fig. 10a | 91-105 | 148-198 | 295-342 | Fig. 10b | 64-96 | 142-162 | 259-285 |
| LD2-14 | Fig. 11a | 91-105 | 148-198 | 295-342 | Fig. 11b | 64-96 | 142-162 | 259-285 |
| LD2-17 | Fig. 12a | 91-105 | 148-198 | 295-342 | Fig. 12b | 64-96 | 142-162 | 259-285 |
| LD2-20 | Fig. 13a | 91-105 | 148-198 | 295-342 | Fig. 13b | 64-96 | 142-162 | 259-285 |
| LD1-6-17 | Fig. 14a | 91-105 | 148-198 | 295-351 | Fig. 14b | 64-96 | 142-162 | 259-285 |
| LD1/2-6-3 | Fig. 15a | 91-105 | 148-198 | 295-342 | Fig. 15b | 64-96 | 142-162 | 259-285 |
| LD1/2-6-33 | Fig. 16a | 91-105 | 148-198 | 295-342 | Fig. 16b | 64-96 | 142-162 | 259-285 |

--

Col. 3, line 57, delete "The table in claim 1 refers to the appended figures."

Col. 3, line 62, insert --above-- after "table" and delete "of claim 1"

Col. 4, line 6, insert --following-- after "the", insert --;-- after "definition" and delete "of claim 6."

Col. 4, line 6, delete "Prefered" and insert --Preferred--

UNITED STATES PATENT AND TRADEMARK OFFICE
CERTIFICATE OF CORRECTION

PATENT NO. : 7,038,020 B1  Page 4 of 8
APPLICATION NO. : 09/147443
DATED : May 2, 2006
INVENTOR(S) : Andreas Morell et al.

It is certified that error appears in the above-identified patent and that said Letters Patent is hereby corrected as shown below:

Col. 4, line 6, before "Preferred" insert --DNA sequences coding for polypeptides capable of forming antigen binding structures with specificity for Rhesus D antigens which include regions with the Rhesus D-specific CDR 1, CDR 2 and CDR 3 segments of pairs of DNA sequences $V_H$ and $V_L$ with the same or different identification numbers according to the figures given in the table below and functional equivalents thereof:

| Identi-fication No. | $V_H$ | | | | $V_L$ | | | |
|---|---|---|---|---|---|---|---|---|
| | Figure | CDR 1 base pair No. | CDR 2 base pair No. | CDR 3 base pair No. | Figure | CDR 1 base pair No. | CDR 2 base pair No. | CDR 3 base pair No. |
| LD1-40 | Fig. 1a | 91-105 | 148-198 | 295-342 | Fig. 1b | 64-96 | 142-162 | 259-288 |
| LD1-52 | Fig. 2a | 91-105 | 148-198 | 295-342 | Fig. 2b | 64-96 | 142-162 | 259-288 |
| LD1-84 | Fig. 3a | 91-105 | 148-198 | 295-342 | Fig. 3b | 64-96 | 142-162 | 259-285 |
| LD1-110 | Fig. 4a | 91-105 | 148-198 | 295-342 | Fig. 4b | 64-96 | 142-162 | 259-285 |
| LD1-117 | Fig. 5a | 91-105 | 148-198 | 295-345 | Fig. 5b | 64-96 | 142-162 | 259-288 |
| LD2-1 | Fig. 6a | 91-105 | 148-198 | 295-342 | Fig. 6b | 61-99 | 145-165 | 262-294 |
| LD2-4 | Fig. 7a | 91-105 | 148-198 | 295-342 | Fig. 7b | 64-96 | 142-162 | 259-282 |
| LD2-5 | Fig. 8a | 91-105 | 148-198 | 295-342 | Fig. 8b | 64-96 | 142-162 | 259-288 |
| LD2-10 | Fig. 9a | 91-105 | 148-198 | 298-345 | Fig. 9b | 61-102 | 148-168 | 265-294 |
| LD2-11 | Fig. 10a | 91-105 | 148-198 | 295-342 | Fig. 10b | 64-96 | 142-162 | 259-285 |
| LD2-14 | Fig. 11a | 91-105 | 148-198 | 295-342 | Fig. 11b | 64-96 | 142-162 | 259-285 |
| LD2-17 | Fig. 12a | 91-105 | 148-198 | 295-342 | Fig. 12b | 64-96 | 142-162 | 259-285 |
| LD2-20 | Fig. 13a | 91-105 | 148-198 | 295-342 | Fig. 13b | 64-96 | 142-162 | 259-285 |
| LD1-5-17 | Fig. 14a | 91-105 | 148-198 | 295-351 | Fig. 14b | 64-96 | 142-162 | 259-285 |
| LD1/2-8-3 | Fig. 15a | 91-105 | 148-198 | 295-342 | Fig. 15b | 64-96 | 142-162 | 259-285 |
| LD1/2-8-33 | Fig. 16a | 91-105 | 148-198 | 295-342 | Fig. 16b | 64-96 | 142-162 | 259-285 |

--

Col. 4, line 13, insert --following-- before "definition, insert --:-- after "definition" and delete "in the claim 11"

UNITED STATES PATENT AND TRADEMARK OFFICE
CERTIFICATE OF CORRECTION

| | |
|---|---|
| PATENT NO. | : 7,038,020 B1 |
| APPLICATION NO. | : 09/147443 |
| DATED | : May 2, 2006 |
| INVENTOR(S) | : Andreas Morell et al. |

It is certified that error appears in the above-identified patent and that said Letters Patent is hereby corrected as shown below:

Col. 4, after line 13, insert the following paragraph:

--A process for preparing recombinant polypeptides capable of forming antigen binding structures, e.g. Fab fragments, with specificity for Rhesus D antigens, which process comprises the following steps in sequential order:

a) boosting an individual capable for forming anti-Rhesus D antibodies with Rhesus D positive red blood cells, b) isolating mononuclear cells from the individual, c) isolating total RNA from the mononuclear cells, d) preparing a cDNA by using an oligo(dT)primer, reverse transcribing the mRNA with M-MuLV reverse transcriptase, and amplifying the cDNA repertoire by a polymerase chain reaction using immunoglobulin gene family specific primers, e) creating a phage display library by inserting the DNA coding for the heavy and light chain of the Fab polypeptide into a phagemid vector, wherein the DNA for the heavy chain is inserted in frame to the gene coding for the phage protein pIII which allows the expression of a Fab pIII fusion protein on the surface of the phage, f) transforming bacterial cells with the obtained recombinant plasmids, cultivating the transformed bacterial cells, and co-expressing the heavy and the light chains of a Fab on filamentous phage particles, g) amplifying the Fab-carrying phage in bacteria,

UNITED STATES PATENT AND TRADEMARK OFFICE
CERTIFICATE OF CORRECTION

| | | |
|---|---|---|
| PATENT NO. | : 7,038,020 B1 | Page 6 of 8 |
| APPLICATION NO. | : 09/147443 | |
| DATED | : May 2, 2006 | |
| INVENTOR(S) | : Andreas Morell et al. | |

It is certified that error appears in the above-identified patent and that said Letters Patent is hereby corrected as shown below:

h)     selecting individual phage clones by several rounds of panning on Rhesus positive red blood cells, i)     isolating the plasmid DNA from the selected clones and cutting out the gIII gene, j)     transforming bacterial cells with the obtained plasmid, cultivating the transformed bacterial cells expressing the Fab, and isolating the Fab fragments.--

Col. 4, line 16, delete "claim 12" and insert --the following:--

Col. 4 after line 16 insert the following:

--A process for selecting recombinant polypeptides capable of forming antigen binding structures with specificity for Rhesus D antigens, and in particular showing reactivity with the partial Rhesus DVI Variant and without any evidence of reactivity with red blood cells of Rhesus negative phenotypes, in particular without reactivity against the Rhesus alleles C, c, E, and e, which process comprises the following steps in sequential order:

a)     performing several negative absorptions on the following red blood cells: phenotype 1 (r'r, Ccddee) treated with bromelase, phenotype 1 not treated with bromelase, phenotype 2 (ryry, CCddEE) treated with bromelase and phenotype 2 not treated with bromelase, b)     performing a positive absorption on DVI+ red blood cells with or without bromelase treatment,

UNITED STATES PATENT AND TRADEMARK OFFICE
CERTIFICATE OF CORRECTION

PATENT NO. : 7,038,020 B1
APPLICATION NO. : 09/147443
DATED : May 2, 2006
INVENTOR(S) : Andreas Morell et al.

It is certified that error appears in the above-identified patent and that said Letters Patent is hereby corrected as shown below:

c)    determining the titer of phage binding to DVI+ red blood cells, d)    repeating steps a), b) and c) until the titer of phage binding to DVI+ red blood cells has reached a satisfactory level.--

Col. 4, line 18, insert --following-- after "the", insert --:-- after "definition" and delete "of claim 14,"

Col. 4, line 18, before "preferably" insert the following:

--Anti-Rhesus D antibodies having heavy and light chain variable regions comprising the Rhesus D-specific CDR 1, CDR 2 and CDR 3 sequences of pairs of amino acid sequences $V_H$ and $V_L$ having the same or different identification numbers according to the table below:

| Identi-fication No. | $V_H$ | | | | $V_L$ | | | |
|---|---|---|---|---|---|---|---|---|
| | Figure | CDR 1 base pair No. | CDR 2 base pair No. | CDR 3 base pair No. | Figure | CDR 1 base pair No. | CDR 2 base pair No. | CDR 3 base pair No. |
| LD1-40 | Fig. 1a | 91-105 | 148-198 | 295-342 | Fig. 1b | 64-96 | 142-162 | 259-288 |
| LD1-52 | Fig. 2a | 91-105 | 148-198 | 295-342 | Fig. 2b | 64-96 | 142-162 | 259-288 |
| LD1-84 | Fig. 3a | 91-105 | 148-198 | 295-342 | Fig. 3b | 64-96 | 142-162 | 259-285 |
| LD1-110 | Fig. 4a | 91-105 | 148-198 | 295-342 | Fig. 4b | 64-96 | 142-162 | 259-285 |
| LD1-117 | Fig. 5a | 91-105 | 148-198 | 295-345 | Fig. 5b | 64-96 | 142-162 | 259-288 |
| LD2-1 | Fig. 6a | 91-105 | 148-198 | 295-342 | Fig. 6b | 61-99 | 145-165 | 262-294 |
| LD2-4 | Fig. 7a | 91-105 | 148-198 | 295-342 | Fig. 7b | 64-96 | 142-162 | 259-282 |
| LD2-5 | Fig. 8a | 91-105 | 148-198 | 295-342 | Fig. 8b | 64-96 | 142-162 | 259-288 |
| LD2-10 | Fig. 9a | 91-105 | 148-198 | 298-345 | Fig. 9b | 61-102 | 148-168 | 265-294 |
| LD2-11 | Fig. 10a | 91-105 | 148-198 | 295-342 | Fig. 10b | 64-96 | 142-162 | 259-285 |
| LD2-14 | Fig. 11a | 91-105 | 148-198 | 295-342 | Fig. 11b | 64-96 | 142-162 | 259-285 |
| LD2-17 | Fig. 12a | 91-105 | 148-198 | 295-342 | Fig. 12b | 64-96 | 142-162 | 259-285 |
| LD2-20 | Fig. 13a | 91-105 | 148-198 | 295-342 | Fig. 13b | 64-96 | 142-162 | 259-285 |
| LD1-6-17 | Fig. 14a | 91-105 | 148-198 | 295-351 | Fig. 14b | 64-96 | 142-162 | 259-285 |
| LD1/2-6-3 | Fig. 15a | 91-105 | 148-198 | 295-342 | Fig. 15b | 64-96 | 142-162 | 259-285 |
| LD1/2-6-33 | Fig. 16a | 91-105 | 148-198 | 295-342 | Fig. 16b | 64-96 | 142-162 | 259-285 |

--

UNITED STATES PATENT AND TRADEMARK OFFICE
CERTIFICATE OF CORRECTION

PATENT NO. : 7,038,020 B1
APPLICATION NO. : 09/147443
DATED : May 2, 2006
INVENTOR(S) : Andreas Morell et al.

It is certified that error appears in the above-identified patent and that said Letters Patent is hereby corrected as shown below:

Col. 4, line 18, delete "preferably" and insert --. Preferably the antibodies are--

Col. 16, line 3, insert --18-- after "Figure" and delete "and"

Signed and Sealed this

Twenty-ninth Day of January, 2008

JON W. DUDAS
*Director of the United States Patent and Trademark Office*

SEQUENCE LISTING

<160> NUMBER OF SEQ ID NOS: 79

<210> SEQ ID NO 1
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 1

```
cag gtg aaa ctg ctc gag tct ggg gga ggc gtg gtc cag cct ggg agg     48
Gln Val Lys Leu Leu Glu Ser Gly Gly Gly Val Val Gln Pro Gly Arg
 1               5                  10                  15 tcc ctg aga ctc tcc tgt ata gcg tct gga ttc acc ctc agg aat tat     96
Ser Leu Arg Leu Ser Cys Ile Ala Ser Gly Phe Thr Leu Arg Asn Tyr
                20                  25                  30 gcc atg cac tgg gtc cgc cag gct cca ggc aag ggg ctg gag tgg gtg    144
Ala Met His Trp Val Arg Gln Ala Pro Gly Lys Gly Leu Glu Trp Val
        35                  40                  45 gca ggt ata tgg ttt gat gga agt aac aaa aac tat gca gac tcc gtg    192
Ala Gly Ile Trp Phe Asp Gly Ser Asn Lys Asn Tyr Ala Asp Ser Val
    50                  55                  60 aag ggc cga ttc acc atc tcc aga gac aat tcc aag aac acg ctg tat    240
Lys Gly Arg Phe Thr Ile Ser Arg Asp Asn Ser Lys Asn Thr Leu Tyr
 65                 70                  75                  80 ctg caa ctg aac agc ctg aga gac gag gac acg gct gtg tat tat tgt    288
Leu Gln Leu Asn Ser Leu Arg Asp Glu Asp Thr Ala Val Tyr Tyr Cys
                85                  90                  95 gcg aga gag cga gca gca cgt ggt att tct agg ttc tat tac tac atg    336
Ala Arg Glu Arg Ala Ala Arg Gly Ile Ser Arg Phe Tyr Tyr Tyr Met
               100                 105                 110 gac gtc tgg ggc aaa ggg acc acg gtc acc gtc tcc cca                375
Asp Val Trp Gly Lys Gly Thr Thr Val Thr Val Ser Pro
           115                 120                 125
```

<210> SEQ ID NO 2
<211> LENGTH: 125
<212> TYPE: PRT
<213> ORGANISM: Homo sapiens

<400> SEQUENCE: 2

```
Gln Val Lys Leu Leu Glu Ser Gly Gly Val Val Gln Pro Gly Arg
  1               5                  10                  15

Ser Leu Arg Leu Ser Cys Ile Ala Ser Gly Phe Thr Leu Arg Asn Tyr
             20                  25                  30

Ala Met His Trp Val Arg Gln Ala Pro Gly Lys Gly Leu Glu Trp Val
         35                  40                  45

Ala Gly Ile Trp Phe Asp Gly Ser Asn Lys Asn Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Leu Asn Ser Leu Arg Asp Glu Asp Thr Ala Val Tyr Tyr Cys
                 85                  90                  95

Ala Arg Glu Arg Ala Ala Arg Gly Ile Ser Arg Phe Tyr Tyr Tyr Met
             100                 105                 110

Asp Val Trp Gly Lys Gly Thr Thr Val Thr Val Ser Pro
         115                 120                 125

<210> SEQ ID NO 3
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 3 gtg atg acc cag tct cca tcc tcc ctg tct gca tct gta ggc gac aga     48
Val Met Thr Gln Ser Pro Ser Ser Leu Ser Ala Ser Val Gly Asp Arg
  1               5                  10                  15 gtc acc atc act tgc cgg gca agt cag agc att agg agc cat ttg aat     96
Val Thr Ile Thr Cys Arg Ala Ser Gln Ser Ile Arg Ser His Leu Asn
             20                  25                  30 tgg tat cag cag aaa cca ggg aaa gcc cct aag ttg ctg atc tat ggt    144
Trp Tyr Gln Gln Lys Pro Gly Lys Ala Pro Lys Leu Leu Ile Tyr Gly
         35                  40                  45 gcg tcc act ttg caa agt ggc gtc cca tca agg ttc agt ggc agt ggc    192
Ala Ser Thr Leu Gln Ser Gly Val Pro Ser Arg Phe Ser Gly Ser Gly
     50                  55                  60 tct ggg gca gtt ttc act ctc acc atc gcc agt cta caa cct gaa gat    240
Ser Gly Ala Val Phe Thr Leu Thr Ile Ala Ser Leu Gln Pro Glu Asp
 65                  70                  75                  80 ttt gca act tac tac tgt caa gag agt tac agt aat cct cta atc acc    288
Phe Ala Thr Tyr Tyr Cys Gln Glu Ser Tyr Ser Asn Pro Leu Ile Thr
                 85                  90                  95 ttc ggc caa ggg aca cga ctg gag act aaa                            318
Phe Gly Gln Gly Thr Arg Leu Glu Thr Lys
             100                 105

<210> SEQ ID NO 4
<211> LENGTH: 106
<212> TYPE: PRT
<213> ORGANISM: Homo sapiens

<400> SEQUENCE: 4

Val Met Thr Gln Ser Pro Ser Ser Leu Ser Ala Ser Val Gly Asp Arg
  1               5                  10                  15

Val Thr Ile Thr Cys Arg Ala Ser Gln Ser Ile Arg Ser His Leu Asn
             20                  25                  30

Trp Tyr Gln Gln Lys Pro Gly Lys Ala Pro Lys Leu Leu Ile Tyr Gly
         35                  40                  45
```

```
Ala Ser Thr Leu Gln Ser Gly Val Pro Ser Arg Phe Ser Gly Ser Gly
         50                  55                  60

Ser Gly Ala Val Phe Thr Leu Thr Ile Ala Ser Leu Gln Pro Glu Asp
 65                  70                  75                  80

Phe Ala Thr Tyr Tyr Cys Gln Glu Ser Tyr Ser Asn Pro Leu Ile Thr
                 85                  90                  95

Phe Gly Gln Gly Thr Arg Leu Glu Thr Lys
            100                 105

<210> SEQ ID NO 5
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 5 cag gtg aaa ctg ctc gag tct ggg gga ggc gtg gtc cag ccg ggg ggg    48
Gln Val Lys Leu Leu Glu Ser Gly Gly Gly Val Val Gln Pro Gly Gly
 1               5                  10                  15 tcc ctg aga ctc tcc tgt gaa gcg tct gga ttc gcc ctc aga agt tct    96
Ser Leu Arg Leu Ser Cys Glu Ala Ser Gly Phe Ala Leu Arg Ser Ser
             20                  25                  30 ggc atg cac tgg gtc cgc cag gct cct ggc aag ggg ctg gag tgg gtg   144
Gly Met His Trp Val Arg Gln Ala Pro Gly Lys Gly Leu Glu Trp Val
         35                  40                  45 gca ctt ata tgg ttt gat gga agt atc aga tcg tat gca gaa tcc gtg   192
Ala Leu Ile Trp Phe Asp Gly Ser Ile Arg Ser Tyr Ala Glu Ser Val
     50                  55                  60 aag ggc cga ttc acc atc tcc aga gac act tcc aag aac acc cta tat   240
Lys Gly Arg Phe Thr Ile Ser Arg Asp Thr Ser Lys Asn Thr Leu Tyr
 65                  70                  75                  80 ctc caa atg cgc agt ctg agt gcc gac gac acg gct gtg tat tac tgt   288
Leu Gln Met Arg Ser Leu Ser Ala Asp Asp Thr Ala Val Tyr Tyr Cys
                 85                  90                  95 gcg aga gac aag gcg gtt cgg gga att agc agg tac aac tat tac atg   336
Ala Arg Asp Lys Ala Val Arg Gly Ile Ser Arg Tyr Asn Tyr Tyr Met
            100                 105                 110 gac gtc tgg ggc aaa ggg acc acg gtc acc gtc tcc tca                375
Asp Val Trp Gly Lys Gly Thr Thr Val Thr Val Ser Ser
        115                 120                 125

<210> SEQ ID NO 6
<211> LENGTH: 125
<212> TYPE: PRT
<213> ORGANISM: Homo sapiens

<400> SEQUENCE: 6

Gln Val Lys Leu Leu Glu Ser Gly Gly Gly Val Val Gln Pro Gly Gly
 1               5                  10                  15

Ser Leu Arg Leu Ser Cys Glu Ala Ser Gly Phe Ala Leu Arg Ser Ser
             20                  25                  30

Gly Met His Trp Val Arg Gln Ala Pro Gly Lys Gly Leu Glu Trp Val
         35                  40                  45

Ala Leu Ile Trp Phe Asp Gly Ser Ile Arg Ser Tyr Ala Glu Ser Val
     50                  55                  60

Lys Gly Arg Phe Thr Ile Ser Arg Asp Thr Ser Lys Asn Thr Leu Tyr
 65                  70                  75                  80
```

```
Leu Gln Met Arg Ser Leu Ser Ala Asp Asp Thr Ala Val Tyr Tyr Cys
             85                  90                  95

Ala Arg Asp Lys Ala Val Arg Gly Ile Ser Arg Tyr Asn Tyr Tyr Met
            100                 105                 110

Asp Val Trp Gly Lys Gly Thr Thr Val Thr Val Ser Ser
        115                 120                 125
```

<210> SEQ ID NO 7
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 7

```
gtg atg acc cag tct cca tcc tcc ctg tct gca tct gta gga gac aga       48
Val Met Thr Gln Ser Pro Ser Ser Leu Ser Ala Ser Val Gly Asp Arg
  1               5                  10                  15 gtc acc atc act tgc cgg gca agt cag aac att atc cgc tat tta aat       96
Val Thr Ile Thr Cys Arg Ala Ser Gln Asn Ile Ile Arg Tyr Leu Asn
             20                  25                  30 tgg tat cag cag aag cca ggg aaa gcc cct agg ctc ctg atc tat ggt      144
Trp Tyr Gln Gln Lys Pro Gly Lys Ala Pro Arg Leu Leu Ile Tyr Gly
         35                  40                  45 gcg tcc act ttg caa agt ggg gtc cca tca agg ttc agt ggc agt gga      192
Ala Ser Thr Leu Gln Ser Gly Val Pro Ser Arg Phe Ser Gly Ser Gly
     50                  55                  60 tct ggg aca gat ttc act ctc acc atc agt agt ctg caa cct gaa gat      240
Ser Gly Thr Asp Phe Thr Leu Thr Ile Ser Ser Leu Gln Pro Glu Asp
 65                  70                  75                  80 ttt gca act tac tac tgt caa cag agt tac cgt acc cct cca ttc act      288
Phe Ala Thr Tyr Tyr Cys Gln Gln Ser Tyr Arg Thr Pro Pro Phe Thr
                 85                  90                  95 ttc ggc cct ggg acc aaa gtg gag atc aaa                              318
Phe Gly Pro Gly Thr Lys Val Glu Ile Lys
            100                 105
```

<210> SEQ ID NO 8
<211> LENGTH: 106
<212> TYPE: PRT
<213> ORGANISM: Homo sapiens

<400> SEQUENCE: 8

```
Val Met Thr Gln Ser Pro Ser Ser Leu Ser Ala Ser Val Gly Asp Arg
  1               5                  10                  15

Val Thr Ile Thr Cys Arg Ala Ser Gln Asn Ile Ile Arg Tyr Leu Asn
             20                  25                  30

Trp Tyr Gln Gln Lys Pro Gly Lys Ala Pro Arg Leu Leu Ile Tyr Gly
         35                  40                  45

Ala Ser Thr Leu Gln Ser Gly Val Pro Ser Arg Phe Ser Gly Ser Gly
     50                  55                  60

Ser Gly Thr Asp Phe Thr Leu Thr Ile Ser Ser Leu Gln Pro Glu Asp
 65                  70                  75                  80

Phe Ala Thr Tyr Tyr Cys Gln Gln Ser Tyr Arg Thr Pro Pro Phe Thr
                 85                  90                  95

Phe Gly Pro Gly Thr Lys Val Glu Ile Lys
            100                 105
```

<210> SEQ ID NO 9

```
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 9 cag gtg aaa ctg ctc gag tct ggg gga ggc gtg gtc cag ccg ggg ggg      48
Gln Val Lys Leu Leu Glu Ser Gly Gly Gly Val Val Gln Pro Gly Gly
  1               5                  10                  15 tcc ctg aga ctc tcc tgt gaa gcg tct gga ttc acc ctc aga agt tct      96
Ser Leu Arg Leu Ser Cys Glu Ala Ser Gly Phe Thr Leu Arg Ser Ser
             20                  25                  30 ggc atg cac tgg gtc cgc cag gct cct ggc aag ggg ctg gag tgg gtg     144
Gly Met His Trp Val Arg Gln Ala Pro Gly Lys Gly Leu Glu Trp Val
         35                  40                  45 gca ctt ata tgg ttt gat gga agt atc aga tcg tat gca gaa tcc gtg     192
Ala Leu Ile Trp Phe Asp Gly Ser Ile Arg Ser Tyr Ala Glu Ser Val
     50                  55                  60 aag ggc cga ttc acc atc tcc aga gac act tcc aag aac acc cta tat     240
Lys Gly Arg Phe Thr Ile Ser Arg Asp Thr Ser Lys Asn Thr Leu Tyr
 65                  70                  75                  80 ctc caa atg cgc agt ctg agt gcc gac gac acg gct gtg tat tac tgt     288
Leu Gln Met Arg Ser Leu Ser Ala Asp Asp Thr Ala Val Tyr Tyr Cys
                 85                  90                  95 gcg aga gac aag gcg gtt cgg gga att agc agg tac aat tat tac atg     336
Ala Arg Asp Lys Ala Val Arg Gly Ile Ser Arg Tyr Asn Tyr Tyr Met
            100                 105                 110 gac gtc tgg ggc aaa ggg acc acg gtc acc gtc tcc tca                 375
Asp Val Trp Gly Lys Gly Thr Thr Val Thr Val Ser Ser
        115                 120                 125

<210> SEQ ID NO 10
<211> LENGTH: 125
<212> TYPE: PRT
<213> ORGANISM: Homo sapiens

<400> SEQUENCE: 10

Gln Val Lys Leu Leu Glu Ser Gly Gly Gly Val Val Gln Pro Gly Gly
  1               5                  10                  15

Ser Leu Arg Leu Ser Cys Glu Ala Ser Gly Phe Thr Leu Arg Ser Ser
             20                  25                  30

Gly Met His Trp Val Arg Gln Ala Pro Gly Lys Gly Leu Glu Trp Val
         35                  40                  45

Ala Leu Ile Trp Phe Asp Gly Ser Ile Arg Ser Tyr Ala Glu Ser Val
     50                  55                  60

Lys Gly Arg Phe Thr Ile Ser Arg Asp Thr Ser Lys Asn Thr Leu Tyr
 65                  70                  75                  80

Leu Gln Met Arg Ser Leu Ser Ala Asp Asp Thr Ala Val Tyr Tyr Cys
                 85                  90                  95

Ala Arg Asp Lys Ala Val Arg Gly Ile Ser Arg Tyr Asn Tyr Tyr Met
            100                 105                 110

Asp Val Trp Gly Lys Gly Thr Thr Val Thr Val Ser Ser
        115                 120                 125

<210> SEQ ID NO 11
<211> LENGTH: 315
<212> TYPE: DNA
<213> ORGANISM: Homo sapiens
<220> FEATURE:
```

```
<221> NAME/KEY: CDS
<222> LOCATION: (1)..(315)

<400> SEQUENCE: 11 gtg atg acc cag tct cca tcc tcc ctg tct gca tct ata gga gac aga    48
Val Met Thr Gln Ser Pro Ser Ser Leu Ser Ala Ser Ile Gly Asp Arg
 1               5                  10                  15 gtc acc atc acc tgc cgg gca agt cag agt atc atc agg tat ttg aat    96
Val Thr Ile Thr Cys Arg Ala Ser Gln Ser Ile Ile Arg Tyr Leu Asn
             20                  25                  30 tgg tat cag cac aaa cca gga aaa gcc cct aaa ctc ctc atc ttt gct   144
Trp Tyr Gln His Lys Pro Gly Lys Ala Pro Lys Leu Leu Ile Phe Ala
         35                  40                  45 gca tcg aat ttg caa act ggg gtc cca tcc agg ttc agt ggc agt gga   192
Ala Ser Asn Leu Gln Thr Gly Val Pro Ser Arg Phe Ser Gly Ser Gly
     50                  55                  60 tct ggg aca gat ttc act ctc acc atc agt gac ctg cag cct gag gat   240
Ser Gly Thr Asp Phe Thr Leu Thr Ile Ser Asp Leu Gln Pro Glu Asp
 65                  70                  75                  80 ttc gca act tac tac tgt caa cag agt tac agt agg ccg ttc act ttt   288
Phe Ala Thr Tyr Tyr Cys Gln Gln Ser Tyr Ser Arg Pro Phe Thr Phe
                 85                  90                  95 ggc cgg ggg acc agc ctg gac atc aaa                               315
Gly Arg Gly Thr Ser Leu Asp Ile Lys
                100                 105

<210> SEQ ID NO 12
<211> LENGTH: 105
<212> TYPE: PRT
<213> ORGANISM: Homo sapiens

<400> SEQUENCE: 12

Val Met Thr Gln Ser Pro Ser Ser Leu Ser Ala Ser Ile Gly Asp Arg
 1               5                  10                  15

Val Thr Ile Thr Cys Arg Ala Ser Gln Ser Ile Ile Arg Tyr Leu Asn
             20                  25                  30

Trp Tyr Gln His Lys Pro Gly Lys Ala Pro Lys Leu Leu Ile Phe Ala
         35                  40                  45

Ala Ser Asn Leu Gln Thr Gly Val Pro Ser Arg Phe Ser Gly Ser Gly
     50                  55                  60

Ser Gly Thr Asp Phe Thr Leu Thr Ile Ser Asp Leu Gln Pro Glu Asp
 65                  70                  75                  80

Phe Ala Thr Tyr Tyr Cys Gln Gln Ser Tyr Ser Arg Pro Phe Thr Phe
                 85                  90                  95

Gly Arg Gly Thr Ser Leu Asp Ile Lys
                100                 105

<210> SEQ ID NO 13
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 13 cag gtg aaa ctg ctc gag tct ggg gga ggc gtg gtc cag cct ggg agg    48
Gln Val Lys Leu Leu Glu Ser Gly Gly Gly Val Val Gln Pro Gly Arg
 1               5                  10                  15 tcc ctg aga ctc tcc tgt ata gcg tct gga ttc acc ctc agg aat tat    96
Ser Leu Arg Leu Ser Cys Ile Ala Ser Gly Phe Thr Leu Arg Asn Tyr
```

```
                  20                  25                  30
gcc atg cac tgg gtc cgc cag gct cca ggc aag ggg ctg gag tgg gtg       144
Ala Met His Trp Val Arg Gln Ala Pro Gly Lys Gly Leu Glu Trp Val
            35                  40                  45 gca ggt ata tgg ttt gat gga agc aac aaa aac tat gca gac tcc gtg       192
Ala Gly Ile Trp Phe Asp Gly Ser Asn Lys Asn Tyr Ala Asp Ser Val
 50                  55                  60 aag ggc cga ttc acc atc tcc aga gac aac tcc aag aac act ctg ttt       240
Lys Gly Arg Phe Thr Ile Ser Arg Asp Asn Ser Lys Asn Thr Leu Phe
 65                  70                  75                  80 ctg cac atg aac agc ctg aga gcc gag gac acg gct aca tat tac tgt       288
Leu His Met Asn Ser Leu Arg Ala Glu Asp Thr Ala Thr Tyr Tyr Cys
                85                  90                  95 gcg aga gag agg gcg att cgg gga atc agt aga tac aat tac tac atg       336
Ala Arg Glu Arg Ala Ile Arg Gly Ile Ser Arg Tyr Asn Tyr Tyr Met
            100                 105                 110 gac gtc tgg ggc aag ggg acc acg gtc acc gtc tcc tca                   375
Asp Val Trp Gly Lys Gly Thr Thr Val Thr Val Ser Ser
            115                 120                 125

<210> SEQ ID NO 14
<211> LENGTH: 125
<212> TYPE: PRT
<213> ORGANISM: Homo sapiens

<400> SEQUENCE: 14

Gln Val Lys Leu Leu Glu Ser Gly Gly Gly Val Val Gln Pro Gly Arg
 1               5                  10                  15

Ser Leu Arg Leu Ser Cys Ile Ala Ser Gly Phe Thr Leu Arg Asn Tyr
            20                  25                  30

Ala Met His Trp Val Arg Gln Ala Pro Gly Lys Gly Leu Glu Trp Val
            35                  40                  45

Ala Gly Ile Trp Phe Asp Gly Ser Asn Lys Asn Tyr Ala Asp Ser Val
 50                  55                  60

Lys Gly Arg Phe Thr Ile Ser Arg Asp Asn Ser Lys Asn Thr Leu Phe
 65                  70                  75                  80

Leu His Met Asn Ser Leu Arg Ala Glu Asp Thr Ala Thr Tyr Tyr Cys
                85                  90                  95

Ala Arg Glu Arg Ala Ile Arg Gly Ile Ser Arg Tyr Asn Tyr Tyr Met
            100                 105                 110

Asp Val Trp Gly Lys Gly Thr Thr Val Thr Val Ser Ser
            115                 120                 125

<210> SEQ ID NO 15
<211> LENGTH: 315
<212> TYPE: DNA
<213> ORGANISM: Homo sapiens
<220> FEATURE:
<221> NAME/KEY: CDS
<222> LOCATION: (1)..(315)

<400> SEQUENCE: 15 gtg atg acc cag tct cca tcc tcc ctg tct gca tct gta gga gac aga        48
Val Met Thr Gln Ser Pro Ser Ser Leu Ser Ala Ser Val Gly Asp Arg
 1               5                  10                  15 gtc acc atc act tgc cgg gca agt cag agc att cga agc tct tta aat        96
Val Thr Ile Thr Cys Arg Ala Ser Gln Ser Ile Arg Ser Ser Leu Asn
            20                  25                  30 tgg tat cag cag aaa cca ggg aaa gcc cct aaa gtc ctg atc tat gct       144
Trp Tyr Gln Gln Lys Pro Gly Lys Ala Pro Lys Val Leu Ile Tyr Ala
```

```
                          35                  40                  45
gca tcc agt ttg caa agt ggg gtc cca tcc agg ttc agt ggc aga gga        192
Ala Ser Ser Leu Gln Ser Gly Val Pro Ser Arg Phe Ser Gly Arg Gly
     50                  55                  60 tct ggg aca gat ttc act ctc acc atc agc agt ctg cag cct gaa gat        240
Ser Gly Thr Asp Phe Thr Leu Thr Ile Ser Ser Leu Gln Pro Glu Asp
 65                  70                  75                  80 ttt gcg act tat tat tgt caa cag agt tcc agt tcc tcg tgg acg ttc        288
Phe Ala Thr Tyr Tyr Cys Gln Gln Ser Ser Ser Ser Ser Trp Thr Phe
                 85                  90                  95 ggc caa ggg acc aag gtg gaa atc aaa                                    315
Gly Gln Gly Thr Lys Val Glu Ile Lys
            100                 105

<210> SEQ ID NO 16
<211> LENGTH: 105
<212> TYPE: PRT
<213> ORGANISM: Homo sapiens

<400> SEQUENCE: 16

Val Met Thr Gln Ser Pro Ser Ser Leu Ser Ala Ser Val Gly Asp Arg
 1               5                  10                  15

Val Thr Ile Thr Cys Arg Ala Ser Gln Ser Ile Arg Ser Ser Leu Asn
             20                  25                  30

Trp Tyr Gln Gln Lys Pro Gly Lys Ala Pro Lys Val Leu Ile Tyr Ala
         35                  40                  45

Ala Ser Ser Leu Gln Ser Gly Val Pro Ser Arg Phe Ser Gly Arg Gly
     50                  55                  60

Ser Gly Thr Asp Phe Thr Leu Thr Ile Ser Ser Leu Gln Pro Glu Asp
 65                  70                  75                  80

Phe Ala Thr Tyr Tyr Cys Gln Gln Ser Ser Ser Ser Ser Trp Thr Phe
                 85                  90                  95

Gly Gln Gly Thr Lys Val Glu Ile Lys
            100                 105

<210> SEQ ID NO 17
<211> LENGTH: 378
<212> TYPE: DNA
<213> ORGANISM: Homo sapiens
<220> FEATURE:
<221> NAME/KEY: CDS
<222> LOCATION: (1)..(378)

<400> SEQUENCE: 17 cag gtg aaa ctg ctc gag tca gga gga ggc gtg gtc cag cct ggg aag         48
Gln Val Lys Leu Leu Glu Ser Gly Gly Gly Val Val Gln Pro Gly Lys
 1               5                  10                  15 tcc ctg aga ctt tcc tgt gca gcg tct gga ttc agt ttc aat agc cat         96
Ser Leu Arg Leu Ser Cys Ala Ala Ser Gly Phe Ser Phe Asn Ser His
             20                  25                  30 ggc atg cac tgg gtc cgc cag gct cca ggc aag ggg ctg gag tgg gtg        144
Gly Met His Trp Val Arg Gln Ala Pro Gly Lys Gly Leu Glu Trp Val
         35                  40                  45 gca ttt ata tgg ttt gat ggc agt aat aaa tac tat gca gac tcc gtg        192
Ala Phe Ile Trp Phe Asp Gly Ser Asn Lys Tyr Tyr Ala Asp Ser Val
     50                  55                  60 aag ggc cga ttc acc atc acc aga gac aac tcc aag aac acg ctg tat        240
Lys Gly Arg Phe Thr Ile Thr Arg Asp Asn Ser Lys Asn Thr Leu Tyr
 65                  70                  75                  80 ctg caa atg aac agc ctg aga gcc gag gac acg gct gtc tat tac tgt        288
```

```
Leu Gln Met Asn Ser Leu Arg Ala Glu Asp Thr Ala Val Tyr Tyr Cys
                85                  90                  95 gcg aga gag acc tca gta agg cta ggg tat agc cgc tac aat tac tac       336
Ala Arg Glu Thr Ser Val Arg Leu Gly Tyr Ser Arg Tyr Asn Tyr Tyr
            100                 105                 110 atg gac gtc tgg ggc aaa ggg acc acg gtc acc atc tcg tca               378
Met Asp Val Trp Gly Lys Gly Thr Thr Val Thr Ile Ser Ser
            115                 120                 125

<210> SEQ ID NO 18
<211> LENGTH: 126
<212> TYPE: PRT
<213> ORGANISM: Homo sapiens

<400> SEQUENCE: 18

Gln Val Lys Leu Leu Glu Ser Gly Gly Val Val Gln Pro Gly Lys
  1               5                  10                  15

Ser Leu Arg Leu Ser Cys Ala Ala Ser Gly Phe Ser Phe Asn Ser His
                 20                  25                  30

Gly Met His Trp Val Arg Gln Ala Pro Gly Lys Gly Leu Glu Trp Val
             35                  40                  45

Ala Phe Ile Trp Phe Asp Gly Ser Asn Lys Tyr Tyr Ala Asp Ser Val
         50                  55                  60

Lys Gly Arg Phe Thr Ile Thr Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Thr Ser Val Arg Leu Gly Tyr Ser Arg Tyr Asn Tyr Tyr
            100                 105                 110

Met Asp Val Trp Gly Lys Gly Thr Thr Val Thr Ile Ser Ser
            115                 120                 125

<210> SEQ ID NO 19
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 19 gtg atg acc cag tct cca tcc tcc ctg tct gca tct gta gga gac aga        48
Val Met Thr Gln Ser Pro Ser Ser Leu Ser Ala Ser Val Gly Asp Arg
  1               5                  10                  15 gtc acc atc act tgc cgg gca agt cag agc att agg agc cat ttg aat       96
Val Thr Ile Thr Cys Arg Ala Ser Gln Ser Ile Arg Ser His Leu Asn
                 20                  25                  30 tgg tat cag cag aaa cca ggg aaa gcc cct aag ctc ctg atc tat gct      144
Trp Tyr Gln Gln Lys Pro Gly Lys Ala Pro Lys Leu Leu Ile Tyr Ala
             35                  40                  45 gca tcc agt ttg caa ggt ggg gtc cca tca agg ttc agt ggc agt gga      192
Ala Ser Ser Leu Gln Gly Gly Val Pro Ser Arg Phe Ser Gly Ser Gly
         50                  55                  60 tct ggg aca gat ttc act ctc acc atc agc agt ctg caa cct gaa gat      240
Ser Gly Thr Asp Phe Thr Leu Thr Ile Ser Ser Leu Gln Pro Glu Asp
 65                  70                  75                  80 ttt gca act tat tac tgt caa cag agt tac agg gcc cct cag tgg acg      288
Phe Ala Thr Tyr Tyr Cys Gln Gln Ser Tyr Arg Ala Pro Gln Trp Thr
                 85                  90                  95 ttc ggc caa ggg acc aag gtg gaa atc aaa                              318
```

Phe Gly Gln Gly Thr Lys Val Glu Ile Lys
        100                 105

<210> SEQ ID NO 20
<211> LENGTH: 106
<212> TYPE: PRT
<213> ORGANISM: Homo sapiens

<400> SEQUENCE: 20

Val Met Thr Gln Ser Pro Ser Ser Leu Ser Ala Ser Val Gly Asp Arg
 1               5                  10                  15

Val Thr Ile Thr Cys Arg Ala Ser Gln Ser Ile Arg Ser His Leu Asn
            20                  25                  30

Trp Tyr Gln Gln Lys Pro Gly Lys Ala Pro Lys Leu Leu Ile Tyr Ala
        35                  40                  45

Ala Ser Ser Leu Gln Gly Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Ser Tyr Arg Ala Pro Gln Trp Thr
                85                  90                  95

Phe Gly Gln Gly Thr Lys Val Glu Ile Lys
        100                 105

<210> SEQ ID NO 21
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 21 cag gtg aaa ctg ctc gag tct ggg gga ggc gtg gtc cag ccg ggg ggg      48
Gln Val Lys Leu Leu Glu Ser Gly Gly Gly Val Val Gln Pro Gly Gly
 1               5                  10                  15 tcc ctg aga ctc tcc tgt gta gcg tct gga ttc acc ctc agg agt tat      96
Ser Leu Arg Leu Ser Cys Val Ala Ser Gly Phe Thr Leu Arg Ser Tyr
            20                  25                  30 ggc atg cac tgg gtc cgc cag gct cca ggc aag ggc ctg gag tgg gtg     144
Gly Met His Trp Val Arg Gln Ala Pro Gly Lys Gly Leu Glu Trp Val
        35                  40                  45 gct ttt ata tgg ttt gat gga agt aat aaa gga tat gta gac tcc gtg     192
Ala Phe Ile Trp Phe Asp Gly Ser Asn Lys Gly Tyr Val Asp Ser Val
    50                  55                  60 aag ggc cga ttc acc atc tcc cga gac aat tcc aag aac atg gtc tat     240
Lys Gly Arg Phe Thr Ile Ser Arg Asp Asn Ser Lys Asn Met Val Tyr
65                  70                  75                  80 ctg caa atg aac agc ctg aga gcc gat gac acg gct gta tat tgt         288
Leu Gln Met Asn Ser Leu Arg Ala Asp Asp Thr Ala Val Tyr Tyr Cys
                85                  90                  95 gcg aga gag aag gcg ctt cgg gga atc agc aga tac aat tat tac ctg     336
Ala Arg Glu Lys Ala Leu Arg Gly Ile Ser Arg Tyr Asn Tyr Tyr Leu
            100                 105                 110 gac gtc tgg ggc aag ggg acc acg gtc acc gtc tcc tca                 375
Asp Val Trp Gly Lys Gly Thr Thr Val Thr Val Ser Ser
        115                 120                 125

<210> SEQ ID NO 22
<211> LENGTH: 125
<212> TYPE: PRT

<213> ORGANISM: Homo sapiens

<400> SEQUENCE: 22

```
Gln Val Lys Leu Leu Glu Ser Gly Gly Gly Val Val Gln Pro Gly Gly
  1               5                  10                  15

Ser Leu Arg Leu Ser Cys Val Ala Ser Gly Phe Thr Leu Arg Ser Tyr
             20                  25                  30

Gly Met His Trp Val Arg Gln Ala Pro Gly Lys Gly Leu Glu Trp Val
         35                  40                  45

Ala Phe Ile Trp Phe Asp Gly Ser Asn Lys Gly Tyr Val Asp Ser Val
     50                  55                  60

Lys Gly Arg Phe Thr Ile Ser Arg Asp Asn Ser Lys Asn Met Val Tyr
 65                  70                  75                  80

Leu Gln Met Asn Ser Leu Arg Ala Asp Asp Thr Ala Val Tyr Tyr Cys
                 85                  90                  95

Ala Arg Glu Lys Ala Leu Arg Gly Ile Ser Arg Tyr Asn Tyr Tyr Leu
            100                 105                 110

Asp Val Trp Gly Lys Gly Thr Thr Val Thr Val Ser Ser
            115                 120                 125
```

<210> SEQ ID NO 23
<211> LENGTH: 333
<212> TYPE: DNA
<213> ORGANISM: Homo sapiens
<220> FEATURE:
<221> NAME/KEY: CDS
<222> LOCATION: (1)..(333)

<400> SEQUENCE: 23

```
gtg gtg act cag cca ccc tca gcg tct ggg acc ccc gga cag agg gtc    48
Val Val Thr Gln Pro Pro Ser Ala Ser Gly Thr Pro Gly Gln Arg Val
  1               5                  10                  15 acc atc tct tgt tct gga agc aac tcc atc ctt gga agt aag tat gta    96
Thr Ile Ser Cys Ser Gly Ser Asn Ser Ile Leu Gly Ser Lys Tyr Val
             20                  25                  30 tac tgg tac cag aaa ctc cca gga acg gcc ccc aaa ctc ctc atc tat   144
Tyr Trp Tyr Gln Lys Leu Pro Gly Thr Ala Pro Lys Leu Leu Ile Tyr
         35                  40                  45 aag aat gat cag cgg ccc tca ggg gtc tct gac cga ttc tct ggc tcc   192
Lys Asn Asp Gln Arg Pro Ser Gly Val Ser Asp Arg Phe Ser Gly Ser
     50                  55                  60 aag tct ggc acc tcg gcc tcc ctg gcc atc agt ggg ctc cgg tcc gag   240
Lys Ser Gly Thr Ser Ala Ser Leu Ala Ile Ser Gly Leu Arg Ser Glu
 65                  70                  75                  80 gat gag gct gac tat tac tgt gca cca tgg gat gcc aac ctg ggt ggc   288
Asp Glu Ala Asp Tyr Tyr Cys Ala Pro Trp Asp Ala Asn Leu Gly Gly
                 85                  90                  95 ccg gtg ttc ggc gga ggg acc aag ctg acc gtc cta agt cag ccc        333
Pro Val Phe Gly Gly Gly Thr Lys Leu Thr Val Leu Ser Gln Pro
            100                 105                 110
```

<210> SEQ ID NO 24
<211> LENGTH: 111
<212> TYPE: PRT
<213> ORGANISM: Homo sapiens

<400> SEQUENCE: 24

```
Val Val Thr Gln Pro Pro Ser Ala Ser Gly Thr Pro Gly Gln Arg Val
  1               5                  10                  15

Thr Ile Ser Cys Ser Gly Ser Asn Ser Ile Leu Gly Ser Lys Tyr Val
```

```
                    20                  25                  30
Tyr Trp Tyr Gln Lys Leu Pro Gly Thr Ala Pro Lys Leu Leu Ile Tyr
            35                  40                  45

Lys Asn Asp Gln Arg Pro Ser Gly Val Ser Asp Arg Phe Ser Gly Ser
        50                  55                  60

Lys Ser Gly Thr Ser Ala Ser Leu Ala Ile Ser Gly Leu Arg Ser Glu
 65                 70                  75                  80

Asp Glu Ala Asp Tyr Tyr Cys Ala Pro Trp Asp Ala Asn Leu Gly Gly
                85                  90                  95

Pro Val Phe Gly Gly Gly Thr Lys Leu Thr Val Leu Ser Gln Pro
            100                 105                 110
```

<210> SEQ ID NO 25
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 25

```
cag gtg aaa ctg ctc gag tcg ggg gga ggc gtg gtc cag ccg ggg ggg        48
Gln Val Lys Leu Leu Glu Ser Gly Gly Gly Val Val Gln Pro Gly Gly
  1               5                  10                  15 tcc ctg aga ctc tcc tgt gaa gcg tct gga ttc acc ctc aga agt tct        96
Ser Leu Arg Leu Ser Cys Glu Ala Ser Gly Phe Thr Leu Arg Ser Ser
                 20                  25                  30 ggc atg cac tgg gtc cgc cag gct cct ggc aag ggg ctg gag tgg gtg       144
Gly Met His Trp Val Arg Gln Ala Pro Gly Lys Gly Leu Glu Trp Val
             35                  40                  45 gca ctt ata tgg ttt gat gga agt atc aga tcg tat gca gaa tcc gtg       192
Ala Leu Ile Trp Phe Asp Gly Ser Ile Arg Ser Tyr Ala Glu Ser Val
         50                  55                  60 aag ggc cga ttc acc atc tcc aga gac act tcc aag aac acc cta tat       240
Lys Gly Arg Phe Thr Ile Ser Arg Asp Thr Ser Lys Asn Thr Leu Tyr
 65                 70                  75                  80 ctc caa atg cgc agt ctg agt gcc gac gac acg gct gtg tat tac tgt       288
Leu Gln Met Arg Ser Leu Ser Ala Asp Asp Thr Ala Val Tyr Tyr Cys
                 85                  90                  95 gcg aga gac aag gcg gtt cgg gga att agc agg tac aac tat tac atg       336
Ala Arg Asp Lys Ala Val Arg Gly Ile Ser Arg Tyr Asn Tyr Tyr Met
            100                 105                 110 gac gtc tgg ggc aaa ggg acc acg gtc acc gtc tcc tca                   375
Asp Val Trp Gly Lys Gly Thr Thr Val Thr Val Ser Ser
        115                 120                 125
```

<210> SEQ ID NO 26
<211> LENGTH: 125
<212> TYPE: PRT
<213> ORGANISM: Homo sapiens

<400> SEQUENCE: 26

```
Gln Val Lys Leu Leu Glu Ser Gly Gly Gly Val Val Gln Pro Gly Gly
  1               5                  10                  15

Ser Leu Arg Leu Ser Cys Glu Ala Ser Gly Phe Thr Leu Arg Ser Ser
                 20                  25                  30

Gly Met His Trp Val Arg Gln Ala Pro Gly Lys Gly Leu Glu Trp Val
             35                  40                  45

Ala Leu Ile Trp Phe Asp Gly Ser Ile Arg Ser Tyr Ala Glu Ser Val
         50                  55                  60
```

-continued

```
Lys Gly Arg Phe Thr Ile Ser Arg Asp Thr Ser Lys Asn Thr Leu Tyr
 65                  70                  75                  80

Leu Gln Met Arg Ser Leu Ser Ala Asp Thr Ala Val Tyr Tyr Cys
             85                  90                  95

Ala Arg Asp Lys Ala Val Arg Gly Ile Ser Arg Tyr Asn Tyr Tyr Met
            100                 105                 110

Asp Val Trp Gly Lys Gly Thr Thr Val Thr Val Ser Ser
        115                 120                 125

<210> SEQ ID NO 27
<211> LENGTH: 312
<212> TYPE: DNA
<213> ORGANISM: Homo sapiens
<220> FEATURE:
<221> NAME/KEY: CDS
<222> LOCATION: (1)..(312)

<400> SEQUENCE: 27 gtg atg acc cag tct cca tcc tcc ctg tct gca tct gta gga gac aga      48
Val Met Thr Gln Ser Pro Ser Ser Leu Ser Ala Ser Val Gly Asp Arg
  1               5                  10                  15 gtc acc atc act tgc cgg aca agt cag acc att agc aga aat tta aat      96
Val Thr Ile Thr Cys Arg Thr Ser Gln Thr Ile Ser Arg Asn Leu Asn
             20                  25                  30 tgg tat cag cag aaa cca ggg aaa gcc cct aag ctc ctg atc tat gct     144
Trp Tyr Gln Gln Lys Pro Gly Lys Ala Pro Lys Leu Leu Ile Tyr Ala
         35                  40                  45 aca tcc agt ttg caa agt ggg gtc cca tca agg ttc agt ggc agt gga     192
Thr Ser Ser Leu Gln Ser Gly Val Pro Ser Arg Phe Ser Gly Ser Gly
     50                  55                  60 tct ggg aca gat ttc act ctc acc atc aat agt cta caa cct gaa gat     240
Ser Gly Thr Asp Phe Thr Leu Thr Ile Asn Ser Leu Gln Pro Glu Asp
 65                  70                  75                  80 ttt gca act tac tac tgt caa cag agt tac act acc cct tcg ttc ggc     288
Phe Ala Thr Tyr Tyr Cys Gln Gln Ser Tyr Thr Thr Pro Ser Phe Gly
                 85                  90                  95 caa ggg acc aag gtg gaa atc aaa                                     312
Gln Gly Thr Lys Val Glu Ile Lys
            100

<210> SEQ ID NO 28
<211> LENGTH: 104
<212> TYPE: PRT
<213> ORGANISM: Homo sapiens

<400> SEQUENCE: 28

Val Met Thr Gln Ser Pro Ser Ser Leu Ser Ala Ser Val Gly Asp Arg
  1               5                  10                  15

Val Thr Ile Thr Cys Arg Thr Ser Gln Thr Ile Ser Arg Asn Leu Asn
             20                  25                  30

Trp Tyr Gln Gln Lys Pro Gly Lys Ala Pro Lys Leu Leu Ile Tyr Ala
         35                  40                  45

Thr Ser Ser Leu Gln Ser Gly Val Pro Ser Arg Phe Ser Gly Ser Gly
     50                  55                  60

Ser Gly Thr Asp Phe Thr Leu Thr Ile Asn Ser Leu Gln Pro Glu Asp
 65                  70                  75                  80

Phe Ala Thr Tyr Tyr Cys Gln Gln Ser Tyr Thr Thr Pro Ser Phe Gly
                 85                  90                  95

Gln Gly Thr Lys Val Glu Ile Lys
            100
```

<210> SEQ ID NO 29
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 29

```
cag gtg aaa ctg ctc gag tct ggg gga ggc ttg gtc cag ccg ggg ggg      48
Gln Val Lys Leu Leu Glu Ser Gly Gly Gly Leu Val Gln Pro Gly Gly
  1               5                  10                  15 tcc ctg aga ctc tcc tgt gta gcg tct gga ttc acc ttc agg agt tat      96
Ser Leu Arg Leu Ser Cys Val Ala Ser Gly Phe Thr Phe Arg Ser Tyr
             20                  25                  30 ggc atg cac tgg gtc cgc cag gct cca ggc aag ggc ctg gag tgg gtg     144
Gly Met His Trp Val Arg Gln Ala Pro Gly Lys Gly Leu Glu Trp Val
         35                  40                  45 gct ttt ata tgg ttt gat gga agt aat aaa gga tat gta gac tcc gtg     192
Ala Phe Ile Trp Phe Asp Gly Ser Asn Lys Gly Tyr Val Asp Ser Val
     50                  55                  60 aag ggc cga ttc acc atc tcc cga gac aat tcc aag aac atg ctc tat     240
Lys Gly Arg Phe Thr Ile Ser Arg Asp Asn Ser Lys Asn Met Leu Tyr
 65                  70                  75                  80 ctg caa atg aat agc ctg aga gcc gag gac acg gct gta tat tat tgt     288
Leu Gln Met Asn Ser Leu Arg Ala Glu Asp Thr Ala Val Tyr Tyr Cys
                 85                  90                  95 gcg aga gag aag gcg ctt cgg gga atc agt aga tac aat tat tac ctg     336
Ala Arg Glu Lys Ala Leu Arg Gly Ile Ser Arg Tyr Asn Tyr Tyr Leu
            100                 105                 110 gac gtc tgg ggc aag ggg gcc acg gtc acc gtc tcc tca                 375
Asp Val Trp Gly Lys Gly Ala Thr Val Thr Val Ser Ser
        115                 120                 125
```

<210> SEQ ID NO 30
<211> LENGTH: 125
<212> TYPE: PRT
<213> ORGANISM: Homo sapiens

<400> SEQUENCE: 30

```
Gln Val Lys Leu Leu Glu Ser Gly Gly Gly Leu Val Gln Pro Gly Gly
  1               5                  10                  15

Ser Leu Arg Leu Ser Cys Val Ala Ser Gly Phe Thr Phe Arg Ser Tyr
             20                  25                  30

Gly Met His Trp Val Arg Gln Ala Pro Gly Lys Gly Leu Glu Trp Val
         35                  40                  45

Ala Phe Ile Trp Phe Asp Gly Ser Asn Lys Gly Tyr Val Asp Ser Val
     50                  55                  60

Lys Gly Arg Phe Thr Ile Ser Arg Asp Asn Ser Lys Asn Met Leu Tyr
 65                  70                  75                  80

Leu Gln Met Asn Ser Leu Arg Ala Glu Asp Thr Ala Val Tyr Tyr Cys
                 85                  90                  95

Ala Arg Glu Lys Ala Leu Arg Gly Ile Ser Arg Tyr Asn Tyr Tyr Leu
            100                 105                 110

Asp Val Trp Gly Lys Gly Ala Thr Val Thr Val Ser Ser
        115                 120                 125
```

<210> SEQ ID NO 31

```
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 31 gtg atg acc cag tct cca tcc tcc ctg tct gca tct ata ggc gac aga      48
Val Met Thr Gln Ser Pro Ser Ser Leu Ser Ala Ser Ile Gly Asp Arg
 1               5                  10                  15 gtc acc atc act tgc cgg gca agt cag agc gtt acc agg tct tta aat      96
Val Thr Ile Thr Cys Arg Ala Ser Gln Ser Val Thr Arg Ser Leu Asn
             20                  25                  30 tgg tat cag cag aaa cca ggg aaa gcc cct agg ctc cta atc ttt gct     144
Trp Tyr Gln Gln Lys Pro Gly Lys Ala Pro Arg Leu Leu Ile Phe Ala
         35                  40                  45 gcg tcc act ttg caa agt ggg gtc cca tca agg ttc agt ggc agt gga     192
Ala Ser Thr Leu Gln Ser Gly Val Pro Ser Arg Phe Ser Gly Ser Gly
     50                  55                  60 tct ggg aca gat ttc acc ctc acc atc agc agt ctg caa cct gag gat     240
Ser Gly Thr Asp Phe Thr Leu Thr Ile Ser Ser Leu Gln Pro Glu Asp
 65                  70                  75                  80 ttt gga act tac tac tgt caa cag aat tac agg acc cct cag tgg acg     288
Phe Gly Thr Tyr Tyr Cys Gln Gln Asn Tyr Arg Thr Pro Gln Trp Thr
                 85                  90                  95 ttc ggc caa ggg acc aag gta gaa atc aaa                             318
Phe Gly Gln Gly Thr Lys Val Glu Ile Lys
            100                 105

<210> SEQ ID NO 32
<211> LENGTH: 106
<212> TYPE: PRT
<213> ORGANISM: Homo sapiens

<400> SEQUENCE: 32

Val Met Thr Gln Ser Pro Ser Ser Leu Ser Ala Ser Ile Gly Asp Arg
 1               5                  10                  15

Val Thr Ile Thr Cys Arg Ala Ser Gln Ser Val Thr Arg Ser Leu Asn
             20                  25                  30

Trp Tyr Gln Gln Lys Pro Gly Lys Ala Pro Arg Leu Leu Ile Phe Ala
         35                  40                  45

Ala Ser Thr Leu Gln Ser Gly Val Pro Ser Arg Phe Ser Gly Ser Gly
     50                  55                  60

Ser Gly Thr Asp Phe Thr Leu Thr Ile Ser Ser Leu Gln Pro Glu Asp
 65                  70                  75                  80

Phe Gly Thr Tyr Tyr Cys Gln Gln Asn Tyr Arg Thr Pro Gln Trp Thr
                 85                  90                  95

Phe Gly Gln Gly Thr Lys Val Glu Ile Lys
            100                 105

<210> SEQ ID NO 33
<211> LENGTH: 378
<212> TYPE: DNA
<213> ORGANISM: Homo sapiens
<220> FEATURE:
<221> NAME/KEY: CDS
<222> LOCATION: (1)..(378)

<400> SEQUENCE: 33 cag gtg aaa ctg ctc gag tct ggg gga ggc gtg gtc cag ccg ggg ggg      48
Gln Val Lys Leu Leu Glu Ser Gly Gly Gly Val Val Gln Pro Gly Gly
```

-continued

```
                1               5              10               15
tcc ctg aga ctc tcc tgt gta gcg tct gga ttc acc ctc agg agt tat         96
Ser Leu Arg Leu Ser Cys Val Ala Ser Gly Phe Thr Leu Arg Ser Tyr
            20                  25                  30 ggc atg cac tgg gtc cgc cag gct cca ggc aag ggc ctg gag tgg gtg        144
Gly Met His Trp Val Arg Gln Ala Pro Gly Lys Gly Leu Glu Trp Val
        35                  40                  45 gct ttt ata tgg ttt gat gga agt aat aaa gga tat gta gac tcc gtg        192
Ala Phe Ile Trp Phe Asp Gly Ser Asn Lys Gly Tyr Val Asp Ser Val
    50                  55                  60 aag ggc cga ttc acc atc tcc cga gac aat tcc aag aac atg gtc tat        240
Lys Gly Arg Phe Thr Ile Ser Arg Asp Asn Ser Lys Asn Met Val Tyr
65                  70                  75                  80 ctg caa atg aac agc ctg aga gcc gat gac acg gct gta tat tat tat        288
Leu Gln Met Asn Ser Leu Arg Ala Asp Asp Thr Ala Val Tyr Tyr Tyr
                85                  90                  95 tgt gcg aga gag aag gcg ctt cgg gga atc agc aga tac aac tat tac        336
Cys Ala Arg Glu Lys Ala Leu Arg Gly Ile Ser Arg Tyr Asn Tyr Tyr
            100                 105                 110 ctg gac gtc tgg ggc aag ggg acc acg gtc acc gtc tcc tca                378
Leu Asp Val Trp Gly Lys Gly Thr Thr Val Thr Val Ser Ser
        115                 120                 125

<210> SEQ ID NO 34
<211> LENGTH: 126
<212> TYPE: PRT
<213> ORGANISM: Homo sapiens

<400> SEQUENCE: 34

Gln Val Lys Leu Leu Glu Ser Gly Gly Gly Val Val Gln Pro Gly Gly
1               5                  10                  15

Ser Leu Arg Leu Ser Cys Val Ala Ser Gly Phe Thr Leu Arg Ser Tyr
            20                  25                  30

Gly Met His Trp Val Arg Gln Ala Pro Gly Lys Gly Leu Glu Trp Val
        35                  40                  45

Ala Phe Ile Trp Phe Asp Gly Ser Asn Lys Gly Tyr Val Asp Ser Val
    50                  55                  60

Lys Gly Arg Phe Thr Ile Ser Arg Asp Asn Ser Lys Asn Met Val Tyr
65                  70                  75                  80

Leu Gln Met Asn Ser Leu Arg Ala Asp Asp Thr Ala Val Tyr Tyr Tyr
                85                  90                  95

Cys Ala Arg Glu Lys Ala Leu Arg Gly Ile Ser Arg Tyr Asn Tyr Tyr
            100                 105                 110

Leu Asp Val Trp Gly Lys Gly Thr Thr Val Thr Val Ser Ser
        115                 120                 125

<210> SEQ ID NO 35
<211> LENGTH: 333
<212> TYPE: DNA
<213> ORGANISM: Homo sapiens
<220> FEATURE:
<221> NAME/KEY: CDS
<222> LOCATION: (1)..(333)

<400> SEQUENCE: 35 gtg gtg act cag gag ccc tca ctg act gtg tcc cca gga ggg aca gtc         48
Val Val Thr Gln Glu Pro Ser Leu Thr Val Ser Pro Gly Gly Thr Val
1               5                  10                  15 act ctc acc tgt gct tcc agc act ggg gca gtc acc agg ggt tac tat         96
Thr Leu Thr Cys Ala Ser Ser Thr Gly Ala Val Thr Arg Gly Tyr Tyr
```

```
                  20                  25                  30
cca aac tgg ttc cag cag aag cct gga caa gca ccc agg gca ctg att      144
Pro Asn Trp Phe Gln Gln Lys Pro Gly Gln Ala Pro Arg Ala Leu Ile
         35                  40                  45 tat agt aca aac aaa aaa cac tcc tgg acc cct gcc cgg ttc tca ggc      192
Tyr Ser Thr Asn Lys Lys His Ser Trp Thr Pro Ala Arg Phe Ser Gly
 50                  55                  60 tcc ctc ctt ggg ggc aaa gct gcc ctg aca ctg tca ggt gtg cag cct      240
Ser Leu Leu Gly Gly Lys Ala Ala Leu Thr Leu Ser Gly Val Gln Pro
 65                  70                  75                  80 gaa gac gag gct gaa tat tac tgc ctg ctc tac tat ggt ggt gct caa      288
Glu Asp Glu Ala Glu Tyr Tyr Cys Leu Leu Tyr Tyr Gly Gly Ala Gln
                 85                  90                  95 ctc gta ttc ggc gga ggg acc aag ctg acc gtc cta cgt cag ccc          333
Leu Val Phe Gly Gly Gly Thr Lys Leu Thr Val Leu Arg Gln Pro
            100                 105                 110
```

<210> SEQ ID NO 36
<211> LENGTH: 111
<212> TYPE: PRT
<213> ORGANISM: Homo sapiens

<400> SEQUENCE: 36

```
Val Val Thr Gln Glu Pro Ser Leu Thr Val Ser Pro Gly Gly Thr Val
 1               5                  10                  15

Thr Leu Thr Cys Ala Ser Ser Thr Gly Ala Val Thr Arg Gly Tyr Tyr
             20                  25                  30

Pro Asn Trp Phe Gln Gln Lys Pro Gly Gln Ala Pro Arg Ala Leu Ile
         35                  40                  45

Tyr Ser Thr Asn Lys Lys His Ser Trp Thr Pro Ala Arg Phe Ser Gly
 50                  55                  60

Ser Leu Leu Gly Gly Lys Ala Ala Leu Thr Leu Ser Gly Val Gln Pro
 65                  70                  75                  80

Glu Asp Glu Ala Glu Tyr Tyr Cys Leu Leu Tyr Tyr Gly Gly Ala Gln
                 85                  90                  95

Leu Val Phe Gly Gly Gly Thr Lys Leu Thr Val Leu Arg Gln Pro
            100                 105                 110
```

<210> SEQ ID NO 37
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 37

```
cag gtg aaa ctg ctc gag tcg ggg gga ggc gtg gtc cag ccg ggg ggg      48
Gln Val Lys Leu Leu Glu Ser Gly Gly Gly Val Val Gln Pro Gly Gly
 1               5                  10                  15 tcc ctg aga ctc tcc tgt gaa gcg tct gga ttc acc ctc aga agt tct      96
Ser Leu Arg Leu Ser Cys Glu Ala Ser Gly Phe Thr Leu Arg Ser Ser
             20                  25                  30 ggc atg cac tgg gtc cgc cag gct cct ggc aag ggg ctg gag tgg gtg     144
Gly Met His Trp Val Arg Gln Ala Pro Gly Lys Gly Leu Glu Trp Val
         35                  40                  45 gca ctt ata tgg ttt gat gga agt atc aga tcg tat gca gaa tcc gtg     192
Ala Leu Ile Trp Phe Asp Gly Ser Ile Arg Ser Tyr Ala Glu Ser Val
 50                  55                  60 aag ggc cga ttc acc atc tcc aga gac act tcc aag aac acc cta tat     240
```

```
ctc caa atg cgc agt ctg agt gcc gac gac acg gct gtg tat tac tgt    288
Leu Gln Met Arg Ser Leu Ser Ala Asp Asp Thr Ala Val Tyr Tyr Cys
                85                  90                  95 gcg aga gac aag gcg gtt cgg gga att agc agg tac aac tat tac atg    336
Ala Arg Asp Lys Ala Val Arg Gly Ile Ser Arg Tyr Asn Tyr Tyr Met
            100                 105                 110 gac gtc tgg ggc aaa ggg acc acg gtc acc gtc tcc tca                375
Asp Val Trp Gly Lys Gly Thr Thr Val Thr Val Ser Ser
        115                 120                 125

<210> SEQ ID NO 38
<211> LENGTH: 125
<212> TYPE: PRT
<213> ORGANISM: Homo sapiens

<400> SEQUENCE: 38

Gln Val Lys Leu Leu Glu Ser Gly Gly Val Val Gln Pro Gly Gly
 1               5                  10                  15

Ser Leu Arg Leu Ser Cys Glu Ala Ser Gly Phe Thr Leu Arg Ser Ser
            20                  25                  30

Gly Met His Trp Val Arg Gln Ala Pro Gly Lys Gly Leu Glu Trp Val
        35                  40                  45

Ala Leu Ile Trp Phe Asp Gly Ser Ile Arg Ser Tyr Ala Glu Ser Val
    50                  55                  60

Lys Gly Arg Phe Thr Ile Ser Arg Asp Thr Ser Lys Asn Thr Leu Tyr
65                  70                  75                  80

Leu Gln Met Arg Ser Leu Ser Ala Asp Asp Thr Ala Val Tyr Tyr Cys
                85                  90                  95

Ala Arg Asp Lys Ala Val Arg Gly Ile Ser Arg Tyr Asn Tyr Tyr Met
            100                 105                 110

Asp Val Trp Gly Lys Gly Thr Thr Val Thr Val Ser Ser
        115                 120                 125

<210> SEQ ID NO 39
<211> LENGTH: 315
<212> TYPE: DNA
<213> ORGANISM: Homo sapiens
<220> FEATURE:
<221> NAME/KEY: CDS
<222> LOCATION: (1)..(315)

<400> SEQUENCE: 39 gtg ttg acc cag tct cca tcc tcc ctg tct gca tct ata cga gac aga     48
Val Leu Thr Gln Ser Pro Ser Ser Leu Ser Ala Ser Ile Arg Asp Arg
 1               5                  10                  15 gtc acc atc act tgc cgg gca agt cag aac att ggc agt tat tta aat     96
Val Thr Ile Thr Cys Arg Ala Ser Gln Asn Ile Gly Ser Tyr Leu Asn
            20                  25                  30 tgg tat cag cac aaa cca ggg aca gcc cct aaa ctc ctg atc tat gct    144
Trp Tyr Gln His Lys Pro Gly Thr Ala Pro Lys Leu Leu Ile Tyr Ala
        35                  40                  45 gta tcc gct ttg caa agt ggg gtc cca tcg agg ttc agt ggc agt aga    192
Val Ser Ala Leu Gln Ser Gly Val Pro Ser Arg Phe Ser Gly Ser Arg
    50                  55                  60 tct ggg aca gat ttc act ctc acc atc agc agt ctg caa cct gaa gat    240
Ser Gly Thr Asp Phe Thr Leu Thr Ile Ser Ser Leu Gln Pro Glu Asp
65                  70                  75                  80 ttt gca act tac tac tgt caa cag agt tac agt ccc ccg tac act ttc    288
Phe Ala Thr Tyr Tyr Cys Gln Gln Ser Tyr Ser Pro Pro Tyr Thr Phe
```

```
                Phe Ala Thr Tyr Tyr Cys Gln Gln Ser Tyr Ser Pro Pro Tyr Thr Phe
                                85                  90                  95 ggc cag ggg acc aac ctg cag atc aaa                                              315
Gly Gln Gly Thr Asn Leu Gln Ile Lys
            100                 105
```

<210> SEQ ID NO 40
<211> LENGTH: 105
<212> TYPE: PRT
<213> ORGANISM: Homo sapiens

<400> SEQUENCE: 40

```
Val Leu Thr Gln Ser Pro Ser Ser Leu Ser Ala Ser Ile Arg Asp Arg
 1               5                  10                  15

Val Thr Ile Thr Cys Arg Ala Ser Gln Asn Ile Gly Ser Tyr Leu Asn
                20                  25                  30

Trp Tyr Gln His Lys Pro Gly Thr Ala Pro Lys Leu Leu Ile Tyr Ala
            35                  40                  45

Val Ser Ala Leu Gln Ser Gly Val Pro Ser Arg Phe Ser Gly Ser Arg
        50                  55                  60

Ser Gly Thr Asp Phe Thr Leu Thr Ile Ser Ser Leu Gln Pro Glu Asp
 65                  70                  75                  80

Phe Ala Thr Tyr Tyr Cys Gln Gln Ser Tyr Ser Pro Pro Tyr Thr Phe
                85                  90                  95

Gly Gln Gly Thr Asn Leu Gln Ile Lys
            100                 105
```

<210> SEQ ID NO 41
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 41

```
cag gtg aaa ctg ctc gag tct ggg gga ggc gtg gtc cag ccg ggg ggg             48
Gln Val Lys Leu Leu Glu Ser Gly Gly Gly Val Val Gln Pro Gly Gly
 1               5                  10                  15 tcc ctg aga gtc gcc tgt gta gcg tct gga ttc acc ttc agg aat ttt            96
Ser Leu Arg Val Ala Cys Val Ala Ser Gly Phe Thr Phe Arg Asn Phe
                20                  25                  30 ggc atg cac tgg gtc cgc cag gct cca ggc aag ggg ctg gag tgg gtg           144
Gly Met His Trp Val Arg Gln Ala Pro Gly Lys Gly Leu Glu Trp Val
            35                  40                  45 gct ttt att tgg ttt gat gca agt aat aaa gga tat gga gac tcc gtt           192
Ala Phe Ile Trp Phe Asp Ala Ser Asn Lys Gly Tyr Gly Asp Ser Val
        50                  55                  60 aag ggc cga ttc acc gtc tcc aga gac aat tcc aag aac acg ctc tat           240
Lys Gly Arg Phe Thr Val Ser Arg Asp Asn Ser Lys Asn Thr Leu Tyr
 65                  70                  75                  80 ctg caa atg aac ggc ctg aga gcc gaa gac acg gct gta tat tat tgt           288
Leu Gln Met Asn Gly Leu Arg Ala Glu Asp Thr Ala Val Tyr Tyr Cys
                85                  90                  95 gcg aga gag aag gcg gtt cgg gga att agt aga tac aac tac tac atg           336
Ala Arg Glu Lys Ala Val Arg Gly Ile Ser Arg Tyr Asn Tyr Tyr Met
            100                 105                 110 gac gtc tgg ggc aag ggg acc acg gtc acc gtc tcc tca                       375
Asp Val Trp Gly Lys Gly Thr Thr Val Thr Val Ser Ser
        115                 120                 125
```

<210> SEQ ID NO 42
<211> LENGTH: 125
<212> TYPE: PRT
<213> ORGANISM: Homo sapiens

<400> SEQUENCE: 42

```
Gln Val Lys Leu Leu Glu Ser Gly Gly Gly Val Val Gln Pro Gly Gly
 1               5                  10                  15

Ser Leu Arg Val Ala Cys Val Ala Ser Gly Phe Thr Phe Arg Asn Phe
                20                  25                  30

Gly Met His Trp Val Arg Gln Ala Pro Gly Lys Gly Leu Glu Trp Val
            35                  40                  45

Ala Phe Ile Trp Phe Asp Ala Ser Asn Lys Gly Tyr Gly Asp Ser Val
        50                  55                  60

Lys Gly Arg Phe Thr Val Ser Arg Asp Asn Ser Lys Asn Thr Leu Tyr
 65                  70                  75                  80

Leu Gln Met Asn Gly Leu Arg Ala Glu Asp Thr Ala Val Tyr Tyr Cys
                85                  90                  95

Ala Arg Glu Lys Ala Val Arg Gly Ile Ser Arg Tyr Asn Tyr Tyr Met
            100                 105                 110

Asp Val Trp Gly Lys Gly Thr Thr Val Thr Val Ser Ser
        115                 120                 125
```

<210> SEQ ID NO 43
<211> LENGTH: 315
<212> TYPE: DNA
<213> ORGANISM: Homo sapiens
<220> FEATURE:
<221> NAME/KEY: CDS
<222> LOCATION: (1)..(315)

<400> SEQUENCE: 43

```
gtg atg acc cag tct cca tcc tcc ctg tct gca tct gtg gga gac aga      48
Val Met Thr Gln Ser Pro Ser Ser Leu Ser Ala Ser Val Gly Asp Arg
 1               5                  10                  15 gtc acc atc act tgc cgg gca agt cag agc att atc aac aat tta aat      96
Val Thr Ile Thr Cys Arg Ala Ser Gln Ser Ile Ile Asn Asn Leu Asn
                20                  25                  30 tgg tat cag cag aaa cca ggc aaa gcc cct gaa ctc ctg atc tat gct     144
Trp Tyr Gln Gln Lys Pro Gly Lys Ala Pro Glu Leu Leu Ile Tyr Ala
            35                  40                  45 gca tcc agt ttg caa agt ggg gtc cct tca agg ttc cgt ggc agt gga     192
Ala Ser Ser Leu Gln Ser Gly Val Pro Ser Arg Phe Arg Gly Ser Gly
        50                  55                  60 tct ggg aga gat ttc act ctc acc gtc acc agt ctg caa cct gaa gat     240
Ser Gly Arg Asp Phe Thr Leu Thr Val Thr Ser Leu Gln Pro Glu Asp
 65                  70                  75                  80 ttt gca act tac tac tgt caa cag agt tac agt acc ctg tgg acg ttc     288
Phe Ala Thr Tyr Tyr Cys Gln Gln Ser Tyr Ser Thr Leu Trp Thr Phe
                85                  90                  95 ggc caa ggg acc aag gtg gaa atc aaa                                 315
Gly Gln Gly Thr Lys Val Glu Ile Lys
            100                 105
```

<210> SEQ ID NO 44
<211> LENGTH: 105
<212> TYPE: PRT
<213> ORGANISM: Homo sapiens

<400> SEQUENCE: 44

```
Val Met Thr Gln Ser Pro Ser Ser Leu Ser Ala Ser Val Gly Asp Arg
 1               5                  10                  15

Val Thr Ile Thr Cys Arg Ala Ser Gln Ser Ile Ile Asn Asn Leu Asn
             20                  25                  30

Trp Tyr Gln Gln Lys Pro Gly Lys Ala Pro Glu Leu Leu Ile Tyr Ala
         35                  40                  45

Ala Ser Ser Leu Gln Ser Gly Val Pro Ser Arg Phe Arg Gly Ser Gly
     50                  55                  60

Ser Gly Arg Asp Phe Thr Leu Thr Val Thr Ser Leu Gln Pro Glu Asp
 65                  70                  75                  80

Phe Ala Thr Tyr Tyr Cys Gln Gln Ser Tyr Ser Thr Leu Trp Thr Phe
                 85                  90                  95

Gly Gln Gly Thr Lys Val Glu Ile Lys
            100                 105

<210> SEQ ID NO 45
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 45 cag gtg aaa ctg ctc gag tct ggg gga ggc gtg gtc cag ccg ggg ggg        48
Gln Val Lys Leu Leu Glu Ser Gly Gly Gly Val Val Gln Pro Gly Gly
 1               5                  10                  15 tcc ctg aga ctc tcc tgt gta gcg tct gga ttc acc ttc agg agt tat        96
Ser Leu Arg Leu Ser Cys Val Ala Ser Gly Phe Thr Phe Arg Ser Tyr
             20                  25                  30 ggc atg cac tgg gtc cgc cag gct cca ggc aag ggc ctg gag tgg gtg       144
Gly Met His Trp Val Arg Gln Ala Pro Gly Lys Gly Leu Glu Trp Val
         35                  40                  45 gct ttt ata tgg ttt gat gga agt aat aaa gga tat gta gac tcc gtg       192
Ala Phe Ile Trp Phe Asp Gly Ser Asn Lys Gly Tyr Val Asp Ser Val
     50                  55                  60 aag ggc cga ttc acc atc tcc cga gac aat tcc aag aac acg ctc tat       240
Lys Gly Arg Phe Thr Ile Ser Arg Asp Asn Ser Lys Asn Thr Leu Tyr
 65                  70                  75                  80 ctg caa atg aag agc ctg aga gcc gag gac acg gct gta tat tat tgt       288
Leu Gln Met Lys Ser Leu Arg Ala Glu Asp Thr Ala Val Tyr Tyr Cys
                 85                  90                  95 gcg aga gag aag gcg ctt cgg gga atc agt aga tac aac tat tac ctg       336
Ala Arg Glu Lys Ala Leu Arg Gly Ile Ser Arg Tyr Asn Tyr Tyr Leu
            100                 105                 110 gac gtc tgg ggc aag ggg acc acg gtc acc gtc tcc tca                   375
Asp Val Trp Gly Lys Gly Thr Thr Val Thr Val Ser Ser
        115                 120                 125

<210> SEQ ID NO 46
<211> LENGTH: 125
<212> TYPE: PRT
<213> ORGANISM: Homo sapiens

<400> SEQUENCE: 46

Gln Val Lys Leu Leu Glu Ser Gly Gly Gly Val Val Gln Pro Gly Gly
 1               5                  10                  15

Ser Leu Arg Leu Ser Cys Val Ala Ser Gly Phe Thr Phe Arg Ser Tyr
             20                  25                  30

Gly Met His Trp Val Arg Gln Ala Pro Gly Lys Gly Leu Glu Trp Val
```

```
            35                  40                  45
Ala Phe Ile Trp Phe Asp Gly Ser Asn Lys Gly Tyr Val Asp Ser Val
 50                  55                  60

Lys Gly Arg Phe Thr Ile Ser Arg Asp Asn Ser Lys Asn Thr Leu Tyr
 65                  70                  75                  80

Leu Gln Met Lys Ser Leu Arg Ala Glu Asp Thr Ala Val Tyr Tyr Cys
                 85                  90                  95

Ala Arg Glu Lys Ala Leu Arg Gly Ile Ser Arg Tyr Asn Tyr Tyr Leu
            100                 105                 110

Asp Val Trp Gly Lys Gly Thr Thr Val Thr Val Ser Ser
        115                 120                 125

<210> SEQ ID NO 47
<211> LENGTH: 315
<212> TYPE: DNA
<213> ORGANISM: Homo sapiens
<220> FEATURE:
<221> NAME/KEY: CDS
<222> LOCATION: (1)..(315)

<400> SEQUENCE: 47 gtg atg acc cag tct cca ttc tcc ctg tct gca tct gta gga gac aga       48
Val Met Thr Gln Ser Pro Phe Ser Leu Ser Ala Ser Val Gly Asp Arg
  1               5                  10                  15 gtc acc atc act tgc cgg gca agt cag aac att agg agt ttt tta agt       96
Val Thr Ile Thr Cys Arg Ala Ser Gln Asn Ile Arg Ser Phe Leu Ser
             20                  25                  30 tgg tat cag cag aaa cca ggg aca gcc cct aag ctc ctg atc tat gct      144
Trp Tyr Gln Gln Lys Pro Gly Thr Ala Pro Lys Leu Leu Ile Tyr Ala
         35                  40                  45 gca tcc agg ttg caa agt ggg gtc cca tca agg ttc agt ggc agt ggg      192
Ala Ser Arg Leu Gln Ser Gly Val Pro Ser Arg Phe Ser Gly Ser Gly
     50                  55                  60 tct ggg aca gat ttc act ctc acc atc agc act ctg caa cct gaa gat      240
Ser Gly Thr Asp Phe Thr Leu Thr Ile Ser Thr Leu Gln Pro Glu Asp
 65                  70                  75                  80 ttt gcg act tac tac tgt caa cag agt tac agt gcc cct tgg acg ttc      288
Phe Ala Thr Tyr Tyr Cys Gln Gln Ser Tyr Ser Ala Pro Trp Thr Phe
                 85                  90                  95 ggc caa ggg acc aag ctg gaa atc aaa                                  315
Gly Gln Gly Thr Lys Leu Glu Ile Lys
            100                 105

<210> SEQ ID NO 48
<211> LENGTH: 105
<212> TYPE: PRT
<213> ORGANISM: Homo sapiens

<400> SEQUENCE: 48

Val Met Thr Gln Ser Pro Phe Ser Leu Ser Ala Ser Val Gly Asp Arg
  1               5                  10                  15

Val Thr Ile Thr Cys Arg Ala Ser Gln Asn Ile Arg Ser Phe Leu Ser
             20                  25                  30

Trp Tyr Gln Gln Lys Pro Gly Thr Ala Pro Lys Leu Leu Ile Tyr Ala
         35                  40                  45

Ala Ser Arg Leu Gln Ser Gly Val Pro Ser Arg Phe Ser Gly Ser Gly
     50                  55                  60

Ser Gly Thr Asp Phe Thr Leu Thr Ile Ser Thr Leu Gln Pro Glu Asp
 65                  70                  75                  80
```

```
Phe Ala Thr Tyr Tyr Cys Gln Gln Ser Tyr Ser Ala Pro Trp Thr Phe
                 85                  90                  95

Gly Gln Gly Thr Lys Leu Glu Ile Lys
            100                 105

<210> SEQ ID NO 49
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 49 cag gtg aaa ctg ctc gag tct ggg gga ggc gtg gtc cag ccg ggg ggg        48
Gln Val Lys Leu Leu Glu Ser Gly Gly Gly Val Val Gln Pro Gly Gly
  1               5                  10                  15 tcc ctg aga ctc tcc tgt gta gcg tct gga ttc acc tcc agg agt tat        96
Ser Leu Arg Leu Ser Cys Val Ala Ser Gly Phe Thr Ser Arg Ser Tyr
             20                  25                  30 ggc atg cac tgg gtc cgc cag gct cca ggc aag ggc ctg gag tgg gtg       144
Gly Met His Trp Val Arg Gln Ala Pro Gly Lys Gly Leu Glu Trp Val
         35                  40                  45 gct ttt ata tgg ttt gat gga agt aat aaa gga tat gta gac tcc gtg       192
Ala Phe Ile Trp Phe Asp Gly Ser Asn Lys Gly Tyr Val Asp Ser Val
     50                  55                  60 aag ggc cga ttc acc atc tcc cga gac aat tcc aag aac acg ctc tat       240
Lys Gly Arg Phe Thr Ile Ser Arg Asp Asn Ser Lys Asn Thr Leu Tyr
 65                  70                  75                  80 ctg caa atg aag agc ctg aga gcc gag gac acg gct gta tat tat tgt       288
Leu Gln Met Lys Ser Leu Arg Ala Glu Asp Thr Ala Val Tyr Tyr Cys
                 85                  90                  95 gcg aga gag aag gcg ctt cgg gga atc agt aga tac aat tat tac ctg       336
Ala Arg Glu Lys Ala Leu Arg Gly Ile Ser Arg Tyr Asn Tyr Tyr Leu
            100                 105                 110 gac gtc tgg ggc aag ggg acc acg gtc acc gtc tcc tca                   375
Asp Val Trp Gly Lys Gly Thr Thr Val Thr Val Ser Ser
        115                 120                 125

<210> SEQ ID NO 50
<211> LENGTH: 125
<212> TYPE: PRT
<213> ORGANISM: Homo sapiens

<400> SEQUENCE: 50

Gln Val Lys Leu Leu Glu Ser Gly Gly Gly Val Val Gln Pro Gly Gly
  1               5                  10                  15

Ser Leu Arg Leu Ser Cys Val Ala Ser Gly Phe Thr Ser Arg Ser Tyr
             20                  25                  30

Gly Met His Trp Val Arg Gln Ala Pro Gly Lys Gly Leu Glu Trp Val
         35                  40                  45

Ala Phe Ile Trp Phe Asp Gly Ser Asn Lys Gly Tyr Val Asp Ser Val
     50                  55                  60

Lys Gly Arg Phe Thr Ile Ser Arg Asp Asn Ser Lys Asn Thr Leu Tyr
 65                  70                  75                  80

Leu Gln Met Lys Ser Leu Arg Ala Glu Asp Thr Ala Val Tyr Tyr Cys
                 85                  90                  95

Ala Arg Glu Lys Ala Leu Arg Gly Ile Ser Arg Tyr Asn Tyr Tyr Leu
            100                 105                 110

Asp Val Trp Gly Lys Gly Thr Thr Val Thr Val Ser Ser
```

<210> SEQ ID NO 51
<211> LENGTH: 315
<212> TYPE: DNA
<213> ORGANISM: Homo sapiens
<220> FEATURE:
<221> NAME/KEY: CDS
<222> LOCATION: (1)..(315)

<400> SEQUENCE: 51

| | | | | | | | | | | | | | | | | |
|---|---|---|---|---|---|---|---|---|---|---|---|---|---|---|---|---|
| gtg | atg | acc | cag | tct | cca | tcc | tcc | ctg | tct | gca | tct | gta | gga | gac | aga | 48 |
| Val | Met | Thr | Gln | Ser | Pro | Ser | Ser | Leu | Ser | Ala | Ser | Val | Gly | Asp | Arg | |
| 1 | | | | 5 | | | | | 10 | | | | | 15 | | |
| gtc | acc | atc | act | tgc | cgg | gca | agt | cag | agc | att | agc | agc | tat | tta | aat | 96 |
| Val | Thr | Ile | Thr | Cys | Arg | Ala | Ser | Gln | Ser | Ile | Ser | Ser | Tyr | Leu | Asn | |
| | | | 20 | | | | | 25 | | | | | 30 | | | |
| tgg | tat | cag | cag | aaa | cca | ggg | aaa | gcc | cct | aag | ctc | ctg | atc | tat | gct | 144 |
| Trp | Tyr | Gln | Gln | Lys | Pro | Gly | Lys | Ala | Pro | Lys | Leu | Leu | Ile | Tyr | Ala | |
| | | 35 | | | | | 40 | | | | | 45 | | | | |
| gca | tcc | agt | ttg | caa | agt | ggg | gtc | cca | tca | agg | ttc | agt | ggc | agt | gga | 192 |
| Ala | Ser | Ser | Leu | Gln | Ser | Gly | Val | Pro | Ser | Arg | Phe | Ser | Gly | Ser | Gly | |
| 50 | | | | | 55 | | | | | 60 | | | | | | |
| tct | ggg | aca | gat | ttc | act | ctc | acc | atc | agc | agt | ctg | caa | cct | gaa | gat | 240 |
| Ser | Gly | Thr | Asp | Phe | Thr | Leu | Thr | Ile | Ser | Ser | Leu | Gln | Pro | Glu | Asp | |
| 65 | | | | 70 | | | | | 75 | | | | | 80 | | |
| ttt | gca | act | tac | tac | tgt | caa | cag | agt | tac | agt | acc | cga | ttc | act | ttc | 288 |
| Phe | Ala | Thr | Tyr | Tyr | Cys | Gln | Gln | Ser | Tyr | Ser | Thr | Arg | Phe | Thr | Phe | |
| | | | | 85 | | | | | 90 | | | | | 95 | | |
| ggc | cct | ggg | acc | aaa | gtg | gat | atc | aaa | | | | | | | | 315 |
| Gly | Pro | Gly | Thr | Lys | Val | Asp | Ile | Lys | | | | | | | | |
| | | | 100 | | | | | 105 | | | | | | | | |

<210> SEQ ID NO 52
<211> LENGTH: 105
<212> TYPE: PRT
<213> ORGANISM: Homo sapiens

<400> SEQUENCE: 52

Val Met Thr Gln Ser Pro Ser Ser Leu Ser Ala Ser Val Gly Asp Arg
1               5                   10                  15

Val Thr Ile Thr Cys Arg Ala Ser Gln Ser Ile Ser Ser Tyr Leu Asn
            20                  25                  30

Trp Tyr Gln Gln Lys Pro Gly Lys Ala Pro Lys Leu Leu Ile Tyr Ala
        35                  40                  45

Ala Ser Ser Leu Gln Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Ser Tyr Ser Thr Arg Phe Thr Phe
                85                  90                  95

Gly Pro Gly Thr Lys Val Asp Ile Lys
            100                 105

<210> SEQ ID NO 53
<211> LENGTH: 384
<212> TYPE: DNA
<213> ORGANISM: Homo sapiens
<220> FEATURE:
<221> NAME/KEY: CDS
<222> LOCATION: (1)..(384)

<400> SEQUENCE: 53

| cag gtg aaa ctg ctc gag tct ggg gga ggc gtg gtc cag cct ggg agg | 48 |
| Gln Val Lys Leu Leu Glu Ser Gly Gly Gly Val Val Gln Pro Gly Arg | |
| 1               5                   10                  15 | |

| tcc ctg aga ctt tcc tgt gca gcg tct gga ttt acc ttc agt agc tat | 96 |
| Ser Leu Arg Leu Ser Cys Ala Ala Ser Gly Phe Thr Phe Ser Ser Tyr | |
|             20                  25                  30 | |

| ggc atg cac tgg gtc cgc cag gct cca ggc aag ggg ctg gag tgg gtg | 144 |
| Gly Met His Trp Val Arg Gln Ala Pro Gly Lys Gly Leu Glu Trp Val | |
|         35                  40                  45 | |

| gca gat ata tgg ttt gat gga ggt aat aaa cat tat gca gac ttc gtg | 192 |
| Ala Asp Ile Trp Phe Asp Gly Gly Asn Lys His Tyr Ala Asp Phe Val | |
|     50                  55                  60 | |

| aag ggc cga ttc acc atc tcc aga gac aat tcc aag aac acg gtg tat | 240 |
| Lys Gly Arg Phe Thr Ile Ser Arg Asp Asn Ser Lys Asn Thr Val Tyr | |
| 65                  70                  75                  80 | |

| cta caa atg aac agc ctg aga gtc gag gac acg gct gtg tat tac tgt | 288 |
| Leu Gln Met Asn Ser Leu Arg Val Glu Asp Thr Ala Val Tyr Tyr Cys | |
|                 85                  90                  95 | |

| gcg agg gat tac tat agc gtt act aag aaa ctc aga ctc cac tac tac | 336 |
| Ala Arg Asp Tyr Tyr Ser Val Thr Lys Lys Leu Arg Leu His Tyr Tyr | |
|             100                 105                 110 | |

| tac tac atg gac gtc tgg ggc aaa ggg acc acg gtc acc gtc tcc tca | 384 |
| Tyr Tyr Met Asp Val Trp Gly Lys Gly Thr Thr Val Thr Val Ser Ser | |
|         115                 120                 125 | |

<210> SEQ ID NO 54
<211> LENGTH: 128
<212> TYPE: PRT
<213> ORGANISM: Homo sapiens

<400> SEQUENCE: 54

Gln Val Lys Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Asp Ile Trp Phe Asp Gly Gly Asn Lys His Tyr Ala Asp Phe Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Val Glu Asp Thr Ala Val Tyr Tyr Cys
                85                  90                  95

Ala Arg Asp Tyr Tyr Ser Val Thr Lys Lys Leu Arg Leu His Tyr Tyr
            100                 105                 110

Tyr Tyr Met Asp Val Trp Gly Lys Gly Thr Thr Val Thr Val Ser Ser
        115                 120                 125

<210> SEQ ID NO 55
<211> LENGTH: 315
<212> TYPE: DNA
<213> ORGANISM: Homo sapiens
<220> FEATURE:
<221> NAME/KEY: CDS
<222> LOCATION: (1)..(315)

<400> SEQUENCE: 55

| gtg atg acc cag tct cca tcc tcc ctg tct gca tct gta gga gac aga | 48 |
| Val Met Thr Gln Ser Pro Ser Ser Leu Ser Ala Ser Val Gly Asp Arg | |

```
                   1               5                    10                        15
gtc acc atc act tgc cgg gca agt cag ggc att aga aat gat tta acc      96
Val Thr Ile Thr Cys Arg Ala Ser Gln Gly Ile Arg Asn Asp Leu Thr
                          20                  25                  30 tgg tat cag caa aaa cca ggg aaa gcc cct aag ctc ctg atc tat gct     144
Trp Tyr Gln Gln Lys Pro Gly Lys Ala Pro Lys Leu Leu Ile Tyr Ala
                 35                  40                  45 gca tcc aat tta caa agt ggg gtc cca tca agg ttc agc ggc agt gga    192
Ala Ser Asn Leu Gln Ser Gly Val Pro Ser Arg Phe Ser Gly Ser Gly
        50                  55                  60 tct ggc aca gat ttc act ctc acc atc agc agc ctg cag cct gaa gat    240
Ser Gly Thr Asp Phe Thr Leu Thr Ile Ser Ser Leu Gln Pro Glu Asp
65                  70                  75                  80 ttt gca act tat tac tgt cta caa gat aac aat ttc ccg tac act ttt    288
Phe Ala Thr Tyr Tyr Cys Leu Gln Asp Asn Asn Phe Pro Tyr Thr Phe
                 85                  90                  95 ggc cag ggg acc aag ctg gag atc aaa                                315
Gly Gln Gly Thr Lys Leu Glu Ile Lys
                100                 105

<210> SEQ ID NO 56
<211> LENGTH: 105
<212> TYPE: PRT
<213> ORGANISM: Homo sapiens

<400> SEQUENCE: 56

Val Met Thr Gln Ser Pro Ser Ser Leu Ser Ala Ser Val Gly Asp Arg
 1               5                   10                  15

Val Thr Ile Thr Cys Arg Ala Ser Gln Gly Ile Arg Asn Asp Leu Thr
                20                  25                  30

Trp Tyr Gln Gln Lys Pro Gly Lys Ala Pro Lys Leu Leu Ile Tyr Ala
             35                  40                  45

Ala Ser Asn Leu Gln Ser Gly Val Pro Ser Arg Phe Ser Gly Ser Gly
       50                  55                  60

Ser Gly Thr Asp Phe Thr Leu Thr Ile Ser Ser Leu Gln Pro Glu Asp
65                  70                  75                  80

Phe Ala Thr Tyr Tyr Cys Leu Gln Asp Asn Asn Phe Pro Tyr Thr Phe
                 85                 90                  95

Gly Gln Gly Thr Lys Leu Glu Ile Lys
                100                 105

<210> SEQ ID NO 57
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 57 cag gtg aaa ctg ctc gag tct ggg gga ggc gtg gtc cag ccg ggg ggg     48
Gln Val Lys Leu Leu Glu Ser Gly Gly Gly Val Val Gln Pro Gly Gly
 1               5                  10                  15 tcc ctg aga gtc gcc tgt gta gcg tct gga ttc acc ttc agg aat ttt     96
Ser Leu Arg Val Ala Cys Val Ala Ser Gly Phe Thr Phe Arg Asn Phe
                20                  25                  30 ggc atg cac tgg gtc cgc cag gct cca ggc aag ggg ctg gag tgg gtg    144
Gly Met His Trp Val Arg Gln Ala Pro Gly Lys Gly Leu Glu Trp Val
             35                  40                  45 gct ttt att tgg ttt gat gca agt aat aaa gga tat gga gac tcc gtt    192
```

| | | | | | | | | | | | | |
|---|---|---|---|---|---|---|---|---|---|---|---|---|
| Ala | Phe | Ile | Trp | Phe | Asp | Ala | Ser | Asn | Lys | Gly | Tyr | Gly | Asp | Ser | Val |
| | 50 | | | | | 55 | | | | | 60 | | | | |

```
aag ggc cga ttc acc gtc tcc aga gac aat tcc aag aac acg ctc tat      240
Lys Gly Arg Phe Thr Val Ser Arg Asp Asn Ser Lys Asn Thr Leu Tyr
 65              70                  75                  80 ctg caa atg aac ggc ctg aga gcc gaa gac acg gct gta tat tat tgt      288
Leu Gln Met Asn Gly Leu Arg Ala Glu Asp Thr Ala Val Tyr Tyr Cys
                 85                  90                  95 gcg aga gag aag gcg gtt cgg gga att agt aga tac aac tac tac atg      336
Ala Arg Glu Lys Ala Val Arg Gly Ile Ser Arg Tyr Asn Tyr Tyr Met
                100                 105                 110 gac gtc tgg ggc aag ggg acc acg gtc acc gtc tcc tca                  375
Asp Val Trp Gly Lys Gly Thr Thr Val Thr Val Ser Ser
            115                 120                 125

<210> SEQ ID NO 58
<211> LENGTH: 125
<212> TYPE: PRT
<213> ORGANISM: Homo sapiens

<400> SEQUENCE: 58

Gln Val Lys Leu Leu Glu Ser Gly Gly Val Val Gln Pro Gly Gly
 1               5                  10                  15

Ser Leu Arg Val Ala Cys Val Ala Ser Gly Phe Thr Phe Arg Asn Phe
                 20                  25                  30

Gly Met His Trp Val Arg Gln Ala Pro Gly Lys Gly Leu Glu Trp Val
                 35                  40                  45

Ala Phe Ile Trp Phe Asp Ala Ser Asn Lys Gly Tyr Gly Asp Ser Val
     50                  55                      60

Lys Gly Arg Phe Thr Val Ser Arg Asp Asn Ser Lys Asn Thr Leu Tyr
 65              70                  75                  80

Leu Gln Met Asn Gly Leu Arg Ala Glu Asp Thr Ala Val Tyr Tyr Cys
                 85                  90                  95

Ala Arg Glu Lys Ala Val Arg Gly Ile Ser Arg Tyr Asn Tyr Tyr Met
                100                 105                 110

Asp Val Trp Gly Lys Gly Thr Thr Val Thr Val Ser Ser
            115                 120                 125

<210> SEQ ID NO 59
<211> LENGTH: 315
<212> TYPE: DNA
<213> ORGANISM: Homo sapiens
<220> FEATURE:
<221> NAME/KEY: CDS
<222> LOCATION: (1)..(315)

<400> SEQUENCE: 59 gtg atg acc cag tct cca tcc tcc ctg tct gca tct gta gga gac aga       48
Val Met Thr Gln Ser Pro Ser Ser Leu Ser Ala Ser Val Gly Asp Arg
 1               5                  10                  15 gtc acc atc act tgc cgg gca agt cag agc att atc aga tat tta aat       96
Val Thr Ile Thr Cys Arg Ala Ser Gln Ser Ile Ile Arg Tyr Leu Asn
                 20                  25                  30 tgg tat cag cac aaa cca ggg aaa gcc cct aag ctc ctg atc cat act      144
Trp Tyr Gln His Lys Pro Gly Lys Ala Pro Lys Leu Leu Ile His Thr
                 35                  40                  45 gca tcc agt ttg caa agt ggg gtc ccg tca agg ttc agt ggc agt gta      192
Ala Ser Ser Leu Gln Ser Gly Val Pro Ser Arg Phe Ser Gly Ser Val
     50                  55                      60 tct ggg aca gat ttc act ctc acc atc agc agt ctg caa cct gaa gat      240
Ser Gly Thr Asp Phe Thr Leu Thr Ile Ser Ser Leu Gln Pro Glu Asp
```

```
Ser Gly Thr Asp Phe Thr Leu Thr Ile Ser Ser Leu Gln Pro Glu Asp
 65                  70                  75                  80 ttt gca act tac tac tgt caa cag agt tac act acc ccg tac act ttt      288
Phe Ala Thr Tyr Tyr Cys Gln Gln Ser Tyr Thr Thr Pro Tyr Thr Phe
                 85                  90                  95 ggc cag ggg acc aag ctg cag atc aaa                                  315
Gly Gln Gly Thr Lys Leu Gln Ile Lys
            100                 105

<210> SEQ ID NO 60
<211> LENGTH: 105
<212> TYPE: PRT
<213> ORGANISM: Homo sapiens

<400> SEQUENCE: 60

Val Met Thr Gln Ser Pro Ser Ser Leu Ser Ala Ser Val Gly Asp Arg
 1               5                  10                  15

Val Thr Ile Thr Cys Arg Ala Ser Gln Ser Ile Ile Arg Tyr Leu Asn
                 20                  25                  30

Trp Tyr Gln His Lys Pro Gly Lys Ala Pro Lys Leu Leu Ile His Thr
             35                  40                  45

Ala Ser Ser Leu Gln Ser Gly Val Pro Ser Arg Phe Ser Gly Ser Val
         50                  55                  60

Ser Gly Thr Asp Phe Thr Leu Thr Ile Ser Ser Leu Gln Pro Glu Asp
 65                  70                  75                  80

Phe Ala Thr Tyr Tyr Cys Gln Gln Ser Tyr Thr Thr Pro Tyr Thr Phe
                 85                  90                  95

Gly Gln Gly Thr Lys Leu Gln Ile Lys
            100                 105

<210> SEQ ID NO 61
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 61 cag gtg aaa ctg ctc gag tct ggg gga ggc gtg gtc cag ccg ggg ggg      48
Gln Val Lys Leu Leu Glu Ser Gly Gly Gly Val Val Gln Pro Gly Gly
 1               5                  10                  15 tcc ctg aga gtc gcc tgt gta gcg tct gga ttc acc ttc agg aat ttt      96
Ser Leu Arg Val Ala Cys Val Ala Ser Gly Phe Thr Phe Arg Asn Phe
                 20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
             35                  40                  45 gct ttt att tgg ttt gat gca agt aat aaa gga tat gga gac tcc gtt     192
Ala Phe Ile Trp Phe Asp Ala Ser Asn Lys Gly Tyr Gly Asp Ser Val
         50                  55                  60 aag ggc cga ttc acc gtc tcc aga gac aat tcc aag aac acg ctc tat     240
Lys Gly Arg Phe Thr Val Ser Arg Asp Asn Ser Lys Asn Thr Leu Tyr
 65                  70                  75                  80 ctg caa atg aac ggc ctg aga gcc gaa gac acg gct gta tat tat tgt     288
Leu Gln Met Asn Gly Leu Arg Ala Glu Asp Thr Ala Val Tyr Tyr Cys
                 85                  90                  95 gcg aga gag aag gcg gtt cgg gga att agt aga tac aac tac tac atg     336
Ala Arg Glu Lys Ala Val Arg Gly Ile Ser Arg Tyr Asn Tyr Tyr Met
            100                 105                 110
```

```
gac gtc tgg ggc aag ggg acc acg gtc acc gtc tcc tca        375
Asp Val Trp Gly Lys Gly Thr Thr Val Thr Val Ser Ser
        115                 120                 125
```

<210> SEQ ID NO 62
<211> LENGTH: 125
<212> TYPE: PRT
<213> ORGANISM: Homo sapiens

<400> SEQUENCE: 62

```
Gln Val Lys Leu Leu Glu Ser Gly Gly Gly Val Val Gln Pro Gly Gly
  1               5                  10                  15

Ser Leu Arg Val Ala Cys Val Ala Ser Gly Phe Thr Phe Arg Asn Phe
             20                  25                  30

Gly Met His Trp Val Arg Gln Ala Pro Gly Lys Gly Leu Glu Trp Val
         35                  40                  45

Ala Phe Ile Trp Phe Asp Ala Ser Asn Lys Gly Tyr Gly Asp Ser Val
     50                  55                  60

Lys Gly Arg Phe Thr Val Ser Arg Asp Asn Ser Lys Asn Thr Leu Tyr
 65                  70                  75                  80

Leu Gln Met Asn Gly Leu Arg Ala Glu Asp Thr Ala Val Tyr Tyr Cys
                 85                  90                  95

Ala Arg Glu Lys Ala Val Arg Gly Ile Ser Arg Tyr Asn Tyr Tyr Met
            100                 105                 110

Asp Val Trp Gly Lys Gly Thr Thr Val Thr Val Ser Ser
        115                 120                 125
```

<210> SEQ ID NO 63
<211> LENGTH: 315
<212> TYPE: DNA
<213> ORGANISM: Homo sapiens
<220> FEATURE:
<221> NAME/KEY: CDS
<222> LOCATION: (1)..(315)

<400> SEQUENCE: 63

```
gtg atg acc cag tct cca tcc ttc ctg tct gca tct gta gga gac aga        48
Val Met Thr Gln Ser Pro Ser Phe Leu Ser Ala Ser Val Gly Asp Arg
  1               5                  10                  15 gtc acc atc act tgc cgg gca agt cag agc att atc aga tat tta aat        96
Val Thr Ile Thr Cys Arg Ala Ser Gln Ser Ile Ile Arg Tyr Leu Asn
             20                  25                  30 tgg tat cag cac aaa cca ggg aaa gcc cct aag ctc ctg atc cat gct       144
Trp Tyr Gln His Lys Pro Gly Lys Ala Pro Lys Leu Leu Ile His Ala
         35                  40                  45 gca tcc agt ttg caa agt ggg gtc ccg tca agg ttc agt ggc agt gta       192
Ala Ser Ser Leu Gln Ser Gly Val Pro Ser Arg Phe Ser Gly Ser Val
     50                  55                  60 tct ggg aca gat ttc act ctc acc atc agc agt ctg caa cct gaa gat       240
Ser Gly Thr Asp Phe Thr Leu Thr Ile Ser Ser Leu Gln Pro Glu Asp
 65                  70                  75                  80 ttt gca act tac tac tgt caa cag agt tac act acc ccg tac act ttt       288
Phe Ala Thr Tyr Tyr Cys Gln Gln Ser Tyr Thr Thr Pro Tyr Thr Phe
                 85                  90                  95 ggc cag ggg acc aag ctg cag atc aaa                                   315
Gly Gln Gly Thr Lys Leu Gln Ile Lys
            100                 105
```

<210> SEQ ID NO 64
<211> LENGTH: 105
<212> TYPE: PRT

<213> ORGANISM: Homo sapiens

<400> SEQUENCE: 64

```
Val Met Thr Gln Ser Pro Ser Phe Leu Ser Ala Ser Val Gly Asp Arg
 1               5                  10                  15
Val Thr Ile Thr Cys Arg Ala Ser Gln Ser Ile Ile Arg Tyr Leu Asn
            20                  25                  30
Trp Tyr Gln His Lys Pro Gly Lys Ala Pro Lys Leu Leu Ile His Ala
        35                  40                  45
Ala Ser Ser Leu Gln Ser Gly Val Pro Ser Arg Phe Ser Gly Ser Val
    50                  55                  60
Ser Gly Thr Asp Phe Thr Leu Thr Ile Ser Ser Leu Gln Pro Glu Asp
65                  70                  75                  80
Phe Ala Thr Tyr Tyr Cys Gln Gln Ser Tyr Thr Thr Pro Tyr Thr Phe
                85                  90                  95
Gly Gln Gly Thr Lys Leu Gln Ile Lys
            100                 105
```

<210> SEQ ID NO 65
<211> LENGTH: 29
<212> TYPE: DNA
<213> ORGANISM: Homo sapiens

<400> SEQUENCE: 65
cactcccagg tgcagctgct cgagtctgg                            29

<210> SEQ ID NO 66
<211> LENGTH: 32
<212> TYPE: DNA
<213> ORGANISM: Homo sapiens

<400> SEQUENCE: 66
gtgctgtccc aggtcaactt actcgagtct gg                        32

<210> SEQ ID NO 67
<211> LENGTH: 32
<212> TYPE: DNA
<213> ORGANISM: Homo sapiens

<400> SEQUENCE: 67
gtccaggtgg aggtgcagct gctcgagtct gg                        32

<210> SEQ ID NO 68
<211> LENGTH: 32
<212> TYPE: DNA
<213> ORGANISM: Homo sapiens

<400> SEQUENCE: 68
gtcctgtccc aggtgcagct gctcgagtcg gg                        32

<210> SEQ ID NO 69
<211> LENGTH: 32
<212> TYPE: DNA
<213> ORGANISM: Homo sapiens

<400> SEQUENCE: 69
gtctgtgccg aggtgcagct gctcgagtct gg                        32

<210> SEQ ID NO 70
<211> LENGTH: 32
<212> TYPE: DNA

<210> SEQ ID NO 71
<211> LENGTH: 27
<212> TYPE: DNA
<213> ORGANISM: Homo sapiens

<400> SEQUENCE: 70
gtcctgtcac aggtacagct gctcgagtca gg        32

<210> SEQ ID NO 71
<211> LENGTH: 27
<212> TYPE: DNA
<213> ORGANISM: Homo sapiens

<400> SEQUENCE: 71
agcatcacta gtacaagatt tgggctc        27

<210> SEQ ID NO 72
<211> LENGTH: 35
<212> TYPE: DNA
<213> ORGANISM: Homo sapiens

<400> SEQUENCE: 72
gtgcgagatg tgagctcgtg atgacccagt ctcca        35

<210> SEQ ID NO 73
<211> LENGTH: 56
<212> TYPE: DNA
<213> ORGANISM: Homo sapiens

<400> SEQUENCE: 73
tccttctaga ttactaacac tctcccctgt tgaagctctt tgtgacgggc gaactc        56

<210> SEQ ID NO 74
<211> LENGTH: 36
<212> TYPE: DNA
<213> ORGANISM: Homo sapiens

<400> SEQUENCE: 74
ctgcacaggg tcctgggccg agctcgtggt gactca        36

<210> SEQ ID NO 75
<211> LENGTH: 34
<212> TYPE: DNA
<213> ORGANISM: Homo sapiens

<400> SEQUENCE: 75
gcattctaga ctattatgaa cattctgtag gggc        34

<210> SEQ ID NO 76
<211> LENGTH: 35
<212> TYPE: DNA
<213> ORGANISM: Homo sapiens

<400> SEQUENCE: 76
tacgcgttgt gacatcgtga tgacccagtc tccat        35

<210> SEQ ID NO 77
<211> LENGTH: 34
<212> TYPE: DNA
<213> ORGANISM: Homo sapiens

<400> SEQUENCE: 77
agtcgctcag ttcgtttgat ttcaagcttg gtcc        34

<210> SEQ ID NO 78
<211> LENGTH: 34

```
-continued

<212> TYPE: DNA
<213> ORGANISM: Artificial Sequence
<220> FEATURE:
<223> OTHER INFORMATION: Description of Artificial Sequence:  Primer

<400> SEQUENCE: 78
gggtcgacgc acaggtgaaa ctgctcgagt ctgg                                34

<210> SEQ ID NO 79
<211> LENGTH: 31
<212> TYPE: DNA
<213> ORGANISM: Artificial Sequence
<220> FEATURE:
<223> OTHER INFORMATION: Description of Artificial Sequence:  Primer

<400> SEQUENCE: 79
gccgatgtgt aaggtgaccg tggtcccctt g                                   31
```